US010363294B2

(12) United States Patent
Palena et al.

(10) Patent No.: US 10,363,294 B2
(45) Date of Patent: *Jul. 30, 2019

(54) YEAST-BRACHYURY IMMUNOTHERAPEUTIC COMPOSITIONS

(71) Applicants: GlobeImmune, Inc., Louisville, CO (US); The United States of America, as represented by the Secretary, Department of Health and Human Services, Washington, DC (US)

(72) Inventors: Claudia Palena, Potomac, MD (US); Zhimin Guo, Superior, CO (US); David Apelian, Boonton Township, NJ (US); Jeffrey Schlom, Potomac, MD (US)

(73) Assignees: GlobeImmune, Inc., Louisville, CO (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/454,176

(22) Filed: Mar. 9, 2017

(65) Prior Publication Data

US 2017/0246276 A1    Aug. 31, 2017

Related U.S. Application Data

(63) Continuation of application No. 14/926,372, filed on Oct. 29, 2015, now Pat. No. 9,623,097, which is a continuation of application No. 13/803,719, filed on Mar. 14, 2013, now Pat. No. 9,198,941, which is a continuation of application No. PCT/US2012/029636, filed on Mar. 19, 2012.

(60) Provisional application No. 61/453,656, filed on Mar. 17, 2011.

(51) Int. Cl.
| | | |
|---|---|---|
| *A61N 5/10* | (2006.01) | |
| *A61K 38/17* | (2006.01) | |
| *A61K 39/00* | (2006.01) | |
| *A61K 45/06* | (2006.01) | |
| *A61K 36/064* | (2006.01) | |
| *C07K 14/435* | (2006.01) | |

(52) U.S. Cl.
CPC ........ *A61K 39/0011* (2013.01); *A61K 36/064* (2013.01); *A61K 38/17* (2013.01); *A61K 45/06* (2013.01); *A61N 5/10* (2013.01); *C07K 14/435* (2013.01); *A61K 2039/51* (2013.01); *A61K 2039/545* (2013.01); *A61K 2039/55511* (2013.01); *A61K 2039/6006* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,775,622 | A | 10/1988 | Hitzeman et al. |
| 5,234,830 | A | 8/1993 | Oshima et al. |
| 5,310,654 | A | 5/1994 | Isberg et al. |
| 5,413,914 | A | 5/1995 | Franzusoff |
| 5,830,463 | A | 11/1998 | Duke et al. |
| 5,858,378 | A | 1/1999 | Bostwick |
| 5,919,651 | A | 7/1999 | Hitzeman et al. |
| 7,083,787 | B2 | 8/2006 | Duke et al. |
| 7,439,042 | B2 | 10/2008 | Duke et al. |
| 7,465,454 | B2 | 12/2008 | Franzusoff et al. |
| 9,198,941 | B2 | 12/2015 | Palena et al. |
| 9,623,097 | B2 | 4/2017 | Palena et al. |
| 2002/0044948 | A1 | 4/2002 | Samir et al. |
| 2003/0035810 | A1 | 2/2003 | Caplan |
| 2004/0156858 | A1* | 8/2004 | Franzusoff ......... A61K 39/0011 424/185.1 |
| 2007/0172503 | A1 | 7/2007 | Selitrennikoff et al. |
| 2007/0224208 | A1 | 9/2007 | Guo et al. |
| 2008/0003239 | A1 | 1/2008 | Duke et al. |
| 2010/0034840 | A1 | 2/2010 | Apelian et al. |
| 2010/0055121 | A1 | 3/2010 | Schlom et al. |
| 2010/0111912 | A1 | 5/2010 | Apelian et al. |
| 2010/0189749 | A1 | 7/2010 | Franzusoff et al. |
| 2011/0256098 | A1 | 10/2011 | Apelian et al. |
| 2012/0321664 | A1 | 12/2012 | Bellgrau et al. |

FOREIGN PATENT DOCUMENTS

| | | |
|---|---|---|
| EP | 0414404 | 2/1991 |
| FR | 2486400 | 1/1982 |
| WO | WO 2007/008780 | 1/2007 |
| WO | WO 2007/092792 | 8/2007 |
| WO | WO 2007/133835 | 11/2007 |
| WO | WO 2008/106551 | 9/2008 |
| WO | WO 2010/065626 | 6/2010 |
| WO | WO 2010/121180 | 10/2010 |

(Continued)

OTHER PUBLICATIONS

Reis E Sousa et al (Immunobiology, 2001, vol. 204, pp. 595-597) (Year: 2001).*
Extended Search Report for European Patent Application No. 17154014.9, dated Aug. 21, 2017, 10 pages.
Official Action (with English translation) for Israeli Patent Application No. 228421 dated Sep. 3, 2017, 5 pages.
Official Action (with English translation) for Japanese Patent Application No. 2016-249307 dated Sep. 12, 2017, 4 pages.
Official Action for Australian Patent Application No. 2017200715 dated Jan. 8, 2018, 3 pages.

(Continued)

*Primary Examiner* — Karen A. Canella
(74) *Attorney, Agent, or Firm* — Sheridan Ross P.C.

(57) ABSTRACT

Disclosed are yeast-based immunotherapeutic compositions comprising Brachyury antigens, and methods for the prevention and/or treatment of cancers characterized by the expression or overexpression of Brachyury.

32 Claims, 9 Drawing Sheets

Specification includes a Sequence Listing.

(56) References Cited

FOREIGN PATENT DOCUMENTS

| WO | WO 2011/115914 | 9/2011 |
| --- | --- | --- |
| WO | WO 2012/019127 | 2/2012 |
| WO | WO 2012/083302 | 6/2012 |
| WO | WO 2012/109404 | 8/2012 |
| WO | WO 2012/174220 | 12/2012 |
| WO | WO 2013/025972 | 2/2013 |

OTHER PUBLICATIONS

Official Action (English translation) for Chinese Patent Application No. 201280023412.6 dated Dec. 5, 2017, 3 pages.
Notice of Allowance (with English translation) for Japanese Patent Application No. 2016-249307 dated Feb. 13, 2018, 2 pages.
Official Action for Singapore Patent Application No. 10201601913R dated Dec. 6, 2017, 8 pages.
Bachman et al., "Recall proliferation potential of memory CD8+ T cells and antiviral protection," Journal of Immunology, 2005, vol. 175, pp. 4677-4685.
Bizzini et al. "Use of live Saccharomyces cerevisiae cells as a biological response modifier in experimental infections," FEMS Microbiology Immunology, 1990, vol. 64, pp. 155-168.
Brake et al. "alpha-Factor-directed synthesis and secretion of mature foreign proteins in Saccharomyces cerevisiae," Proceedings of the National Academy of Sciences USA, Aug. 1984, vol. 81, pp. 4642-4646.
Efferson et al., "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15," Anticancer research, 2005, vol. 25, pp. 715-724.
Eto et al., "Immunization with recombinant Escherichia coli expressing retinal S-antigen-induced experimental autoimmune uveitis (EAU) in Lewis rats", Cellular Immunology, vol. 147, No. 1 Mar. 1993, pp. 203-214.
Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.
Franzusoff, A. et al. "Yeasts Encoding Tumour Antigens in Cancer Immunotherapy," Expert Opinion on Biological Therapy, Apr. 2005, vol. 5, No. 4, pp. 565-575.
Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.
Holz et al., "A micro-scale process for high-throughput expression of cDNAs in the yeast Saccharomyces cerevisiae," Protein Expression and Purification, 2002, vol. 25, Iss. 3, pp. 372-378.
Kilic et al. "Brachyury expression predicts poor prognosis at early stages of colorectal cancer." European Journal of Cancer, May 2011, vol. 47, No. 7, pp. 1080-1085.
Klepfer et al. "Characterization of rabies glycoprotein expressed in yeast," Archives of Virology, 1993, vol. 128, pp. 269-286.
Lu, et al., "Mutation-Selective Tumor Remission with Ras-Targeted, Whole Yeast-Based Immunotherapy," Cancer Research, 2004, vol. 64, pp. 5084-5088.
Moore et al., "Novel yeast-based vaccine against HIV-SF2 gp160 promotes a cytotoxic 43-62 cell response." FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.
Mosolits et al., "Therapeutic vaccination in patients with gastrointestinal malignancies. A review of immunological and clinical results," Annals of Oncology, 2005, vol. 16, Iss. 6, pp. 847-862.
Palena et al. "The Human T-Box Mesodermal Transcription Factor Brachyury Is a Candidate Target for T-Cell-Mediated Cancer Immunotherapy," Clinical Cancer Research, Apr. 15, 2007, vol. 13, No. 8, pp. 2471-2478.

Sadanaga et al., "Dendritic Cell Vaccination with MAGE Peptide Is a Novel Therapeutic Approach for Gastrointestinal Carcinomas," Clinical Cancer Research, 2001, vol. 7, Iss. 8, pp. 2277-2284.
Schreuder et al. "Yeast expressing hepatitis B virus surface antigen determinants on its surface: implications fora possible oral vaccine," Vaccine, Apr. 1996, vol. 14, No. 5, pp. 383-388.
Sinai et al. "Enhancement of Resistance to Infectious Diseases by Oral Administration of Brewer's Yeast," Infection and Immunity, May 1974, vol. 9, No. 5, pp. 781-787.
Stubbs, et al., "Whole Recombinant Yeast Vaccine Activates Dendritic Cells and Elicits Protective Cell-Mediated Immunity," National Medicine, May 2001, vol. 7, No. 5, pp. 1-5.
Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.
Wheeler, "Preventive vaccines for cervical cancer," Salud p'ublica de M'exico, 1997, vol. 39, pp. 283-287.
Yoshiyuki et al., "Extremely simple, rapid and highly efficient transformation method for the yeast Saccharomyces cerevisiae using glutathione and early log phase cells," Journal of Bioscience and Bioengineering, 2002, vol. 94, Iss. 2, pp. 166-171. (Abstract only).
International Search Report and Written Opinion for International (PCT) Patent Application No. PCT/US2012/029636, dated May 29, 2012 14 pages.
International Preliminary Report on Patentability for International (PCT) Patent Application No. PCT/US2012/029636, dated Sep. 26, 2013 12 pages.
Official Action for Australian Patent Application No. 2012228937 dated Jul. 5, 2016, 3 pages.
Notice of Acceptance for Australian Patent Application No. 2012228937 dated Oct. 19, 2016, 1 page.
Official Action (English translation) for Chinese Patent Application No. 201280023412.6 dated Apr. 3, 2015, 8 pages.
Official Action (English translation) for Chinese Patent Application No. 201280023412.6 dated Nov. 30, 2015, 9 pages.
Official Action (English translation) for Chinese Patent Application No. 201280023412.6 dated Aug. 10, 2016, 7 pages.
Extended Search Report for European Patent Application No. 12757534.8, dated Nov. 20, 2014, 6 pages.
Notice of Intention to Grant for European Patent Application No. 12757534.8, dated Sep. 29, 2016, 7 pages.
Official Action (with English translation) for Japanese Patent Application No. 2013-558234 dated Dec. 22, 2015, 9 pages.
Notice of Allowance (with English translation) for Japanese Patent Application No. 2013-558234 dated Nov. 22, 2016, 2 pages.
Official Action for New Zealand Patent Application No. 616696, dated Jun. 16, 2014 2 pages.
Notice of Acceptance for New Zealand Patent Application No. 616696, dated Sep. 9, 2015, 1 page.
Official Action for New Zealand Patent Application No. 711188 dated Sep. 9, 2015, 2 pages.
Notice of Acceptance for New Zealand Patent Application No. 711188 dated Nov. 29, 2016, 1 page.
Official Action for New Zealand Patent Application No. 724797 dated Oct. 19, 2016, 2 pages.
Official Action (with English translation) for Russian Patent Application No. 2013146324 dated Mar. 23, 2016, 19 pages.
Official Action (with English translation) for Russian Patent Application No. 2013146324 dated Oct. 4, 2016, 9 pages.
Notice of Allowance (with English translation) for Russian Patent Application No. 2013146324 dated Jan. 13, 2017, 33 pages.
Official Action for U.S. Appl. No. 13/803,719, dated Jan. 13, 2015, 17 pages.
Notice of Allowance for U.S. Appl. No. 13/803,719, dated Jul. 30, 2015, 7 pages.
Official Action for U.S. Appl. No. 14/296,372 dated May 20, 2016, 12 pages.
Notice of Allowance for U.S. Appl. No. 14/296,372 dated Dec. 14, 2016, 12 pages.

(56) References Cited

OTHER PUBLICATIONS

Jambhekar et al., "Revisiting Chordoma With Brachyury, a "New Age" Marker: Analysis of a Validation Study on 51 Cases," Archives of Pathology & Laboratory Medicine, 2010, vol. 134, Iss. 8, pp. 1181-1187.
Official Action for Canadian Patent Application No. 2,835,475 dated Jan. 22, 2018, 3 pages.
Notice of Allowance (with English translation) for Chinese Patent Application No. 201280023412.6 dated Jul. 3, 2018, 5 pages.
Official Action for Indian Patent Application No. 8692/DELNP/2013 dated Aug. 2, 2018, 8 pages.
Official Action (with English translation) for Korean Patent Application No. 10-2013-7027169 dated Jun. 23, 2018, 10 pages.
Official Action (with English translation) for Russian Patent Application No. 2017116350 dated May 29, 2018, 11 pages.
Official Action for Canadian Patent Application No. 2,835,475 dated Oct. 11, 2018, 5 pages.
Official Action for European Patent Application No. 17154014.9, dated Dec. 3, 2018, 3 pages.
Official Action (with English translation) for Russian Patent Application No. 2017116350 dated Oct. 22, 2018, 11 pages.
Official Action for Singapore Patent Application No. 10201601913R dated Oct. 10, 2018, 8 pages.
Hayama et al., "Extremely simple, rapid and highly efficient transformation method for the yeast Saccharomyces cerevisiae using glutathione and early log phase cells," Journal of Bioscience and Bioengineering, 2002, vol. 94, Iss. 2, pp. 166-171. (Abstract only).
Official Action for Australian Patent Application No. 2018202972 dated Mar. 6, 2019, 2 pages.
Official Action (with English translation) for Japanese Patent Application No. 2018-046148 dated Apr. 9, 2019, 4 pages.
Official Action (with English translation) for Korean Patent Application No. 10-2013-7027169 dated Feb. 25, 2019, 6 pages.
Decision to Grant (with English translation) for Russian Patent Application No. 2017116350 dated Mar. 28, 2019, 11 pages.

\* cited by examiner

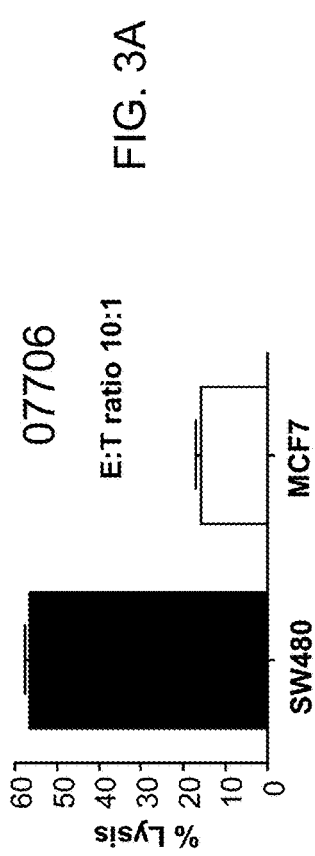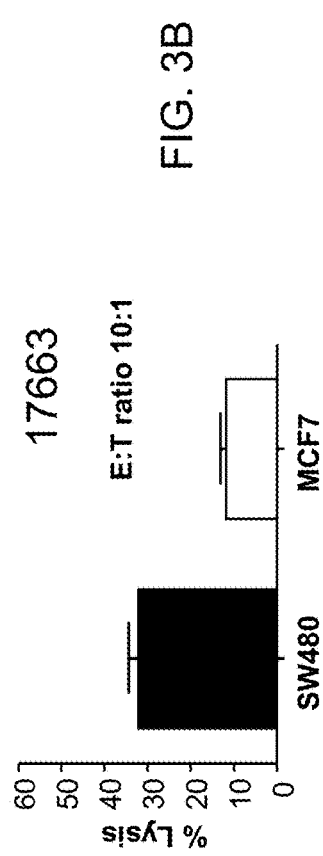

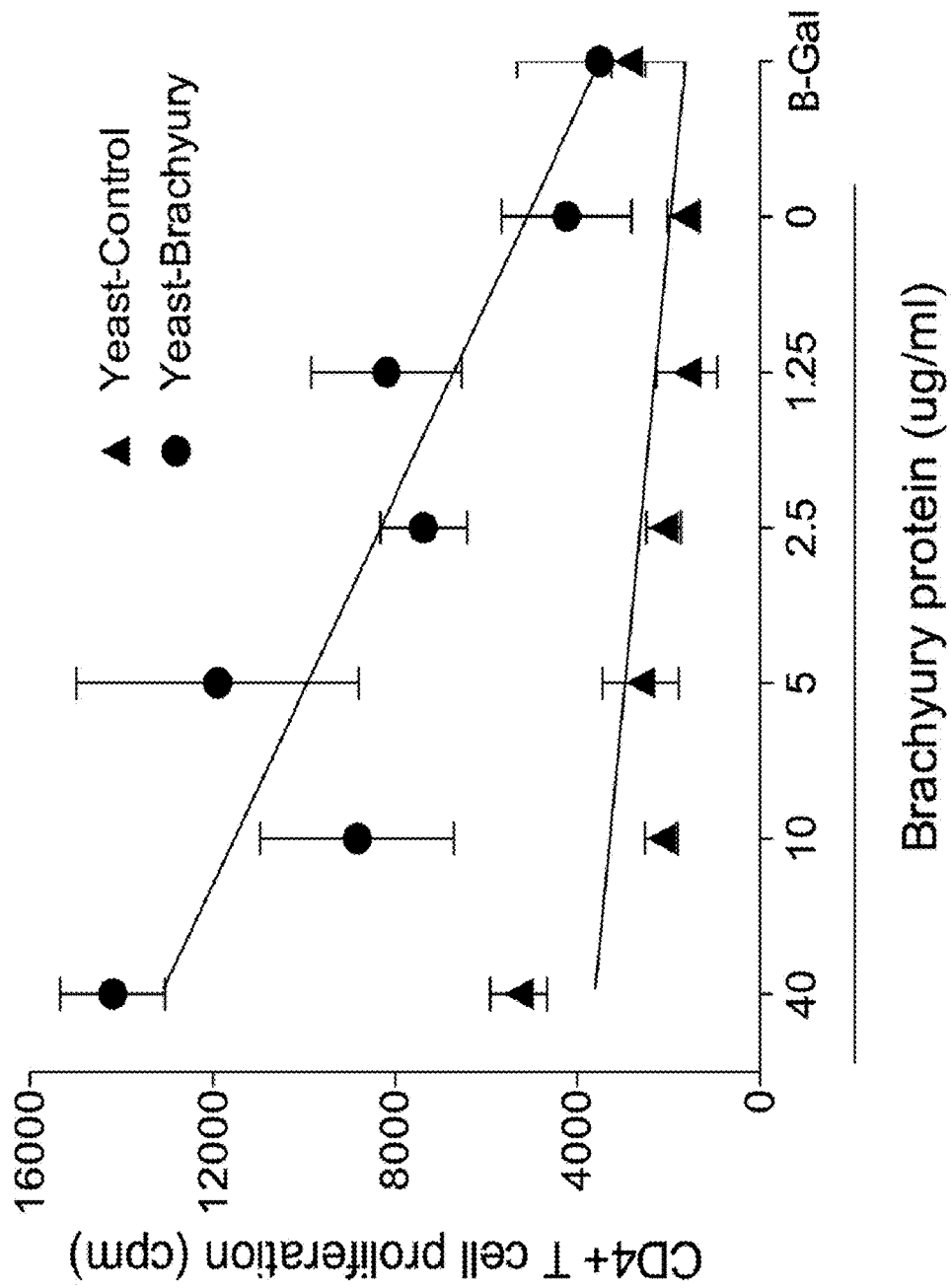

YEAST-BRACHYURY IMMUNOTHERAPEUTIC COMPOSITIONS

CROSS-REFERENCE TO RELATED APPLICATIONS

This application is a continuation application of U.S. application Ser. No. 14/926,372, filed Oct. 29, 2015, now U.S. Pat. No. 9,623,097, which is a continuation application of U.S. application Ser. No. 13/803,719, filed Mar. 14, 2013, now U.S. Pat. No. 9,198,941 which claims the benefit of priority under 35 U.S.C. § 120 and is a continuation of PCT Application No. PCT/US12/29636, filed Mar. 19, 2012, which claims the benefit of priority under 35 U.S.C. § 119(e) to U.S. Provisional Application Ser. No. 61/453,656, filed Mar. 17, 2011. The entire disclosure of each of U.S. application Ser. No. 14/926,372, U.S. application Ser. No. 13/803,719, PCT Application No. PCT/US12/29636 and U.S. Provisional Application Ser. No. 61/453,656 is incorporated herein by reference.

GOVERNMENT RIGHTS

This invention was created in the performance of a Cooperative Research and Development Agreement with the National Institutes of Health, an Agency of the Department of Health and Human Services. The Government of the United States has certain rights in this invention.

STATEMENT REGARDING JOINT RESEARCH AGREEMENT

This invention was made by or on behalf of parties to a Cooperative Research and Development Agreement, executed May 8, 2008. The parties to the Cooperative Research and Development Agreement are: GlobeImmune, Inc. and the U.S. Department of Health and Human Services, as represented by National Cancer Institute, an Institute, Center or Division of the National Institutes of Health.

REFERENCE TO A SEQUENCE LISTING

This application contains a Sequence Listing submitted electronically as a text file by EFS-Web. The text file, named "3923-34-PCT_ST25", has a size in bytes of 76 KB, and was recorded on 13 Mar. 2012. The information contained in the text file is incorporated herein by reference in its entirety pursuant to 37 CFR § 1.52(e)(5).

FIELD OF THE INVENTION

The present invention generally relates to yeast-based immunotherapeutic compositions and methods for the prevention and/or treatment of cancers characterized by the expression or overexpression of Brachyury.

BACKGROUND OF THE INVENTION

Brachyury, also known as "T", is a mesodermal transcription factor and member of the T-box complex of genes. The gene encoding Brachyury (denoted as either T gene or Brachyury gene in humans) was initially identified in 1927 by Nadine Dobrovolskaïa-Zavadskaïa through a mutation in mice that affected tail length and sacral vertebrae in heterozygous animals. The Brachyury gene was cloned in mice in 1990 by Hermann and colleagues (Herrmann et al., 1990, *Nature* 343:617-622) and in humans in 1996 by Edwards and colleagues (Edwards et al., 1996, *Genome Res.* 6:226-223), who also described the deduced amino acid sequence for human Brachyury.

As a member of the T-box family of transcription factors, Brachyury contains the highly conserved DNA-binding domain motif, called "T-box" or T-domain, which binds to a palindromic consensus sequence. Brachyury, like other T-box proteins, has been shown to play a role in early development, and is vital for the formation and differentiation of posterior mesoderm and axial development in vertebrates (see, e.g., Wilkinson et al., 1990, *Nature* 343(6259): 657-659); Beddington et al., 1992, *Development* (Suppl.): 157-165; Schulte-Merker et al., 1994, *Development* 120: 1009-1015; Kispert and Herrmann, 1994, *Dev. Biol.* 161: 179-193; Showell et al., 2004, *Dev Dyn* 229:201-218). More recently, Palena and colleagues have demonstrated that Brachyury is expressed in a variety of human tumor tissues and cancer cell lines and have shown that peptides of Brachyury can be used to generate Brachyury-specific T cell lines in normal donors and cancer patients (Palena et al., 2007, *Clin. Cancer Res.* 13(8):2471-2478). Studies by Fernando et al. have shown that Brachyury promotes the epithelial-mesenchymal transition (EMT) in human tumor cells, conferring on tumor cells a mesenchymal phenotype, as well as migratory and invasive abilities, while attenuating tumor cell cycle progression (Fernando et al., 2010, 1 *Clin. Invest.* 120(2):533-544). Accordingly, Brachyury is involved in metastatic progression of cancer.

Cancer is a leading cause of death worldwide, and the development of effective therapies for cancer continues to be one of the most active areas of research and clinical development. Although a variety of innovative approaches to treat and prevent cancers have been proposed, many cancers continue to have a high rate of mortality and may be difficult to treat or relatively unresponsive to conventional therapies. Cancers associated with Brachyury expression may be found in a variety of tissues, including breast, small intestine, stomach, kidney, bladder, uterus, ovary, testes, lung, colon and prostate, and includes metastatic and late-stage cancers. In addition, Brachyury is expressed in tumors of B cell origin, such as chronic lymphocytic leukemia (CLL), Epstein-Barr virus transformed B cells, Burkitt's and Hodgkin's lymphomas. Therefore, Brachyury appears to play a role in a large number of human cancers. While Brachyury has been proposed to be a target for cancer immunotherapy (see, e.g., Palena et al., supra, Fernando et al., supra, and WO 2008/106551), since this is a relatively new cancer target, there remains a need in the art for new immunotherapeutic products that effectively treat and/or prevent cancers associated with Brachyury expression or overexpression.

SUMMARY OF THE INVENTION

One embodiment of the invention relates to a method to reduce, arrest, reverse, delay or prevent the metastatic progression of cancer in an individual who has cancer. The method includes the step of administering to an individual who has a cancer that is undergoing metastatic progression, is at risk of undergoing metastatic progression, or is predicted to begin undergoing metastatic progression, an immunotherapeutic composition comprising: (a) a yeast vehicle; and (b) a cancer antigen comprising at least one Brachyury antigen. Another embodiment of the invention relates to the use of an immunotherapeutic composition comprising a yeast vehicle and a cancer antigen comprising at least one Brachyury antigen to reduce, arrest, reverse or prevent the metastatic progression of cancer in an individual who has cancer.

In one aspect, of these embodiments of the invention, Brachyury is not detected in the individual's cancer at the time the composition is first administered. In one aspect, Brachyury expression is detected in the individual's cancer at the time the composition is first administered. The individual may have stage I cancer, stage II cancer, stage III cancer, or stage IV cancer.

Another embodiment of the invention relates to a method to prevent or delay the onset of a Brachyury-expressing cancer. The method includes the step of administering to an individual an immunotherapeutic composition comprising: (a) a yeast vehicle; and (b) a cancer antigen comprising at least one Brachyury antigen. Another embodiment of the invention relates to the use of an immunotherapeutic composition comprising a yeast vehicle and a cancer antigen comprising at least one Brachyury antigen to prevent or delay the onset of a Brachyury-expressing cancer.

In one aspect of these embodiments, cancer has not been detected in the individual. In one aspect, the individual is at high risk for developing cancer (e.g., via a genetic predisposition). In one aspect, the individual has a pre-cancerous lesion.

In one aspect of these embodiments, the individual has cancer, but Brachyury-expressing cancer cells have not been detected in the cancer. In one aspect, the cancer is not yet metastatic. In one aspect, the cancer has a high risk of metastasizing. In one aspect, the subject has stage I cancer. In one aspect, the subject has stage II cancer.

Another embodiment of the invention relates to a method to reduce or prevent chemotherapy-resistance or radiation-resistance of tumor cells in a patient with cancer. The method includes the steps of administering to an individual who has cancer and is receiving chemotherapy and/or radiation therapy an immunotherapeutic composition comprising: (a) a yeast vehicle; and (b) a cancer antigen comprising at least one Brachyury antigen. Another embodiment of the invention relates to the use of an immunotherapeutic composition comprising a yeast vehicle and a cancer antigen comprising at least one Brachyury antigen to reduce or prevent chemotherapy-resistance or radiation-resistance of tumor cells in a patient with cancer. In one aspect of this embodiment of the invention, Brachyury is not detected in the individual's cancer at the time the composition is first administered. In one aspect, Brachyury expression is detected in the individual's cancer at the time the composition is first administered.

Yet another embodiment of the invention relates to a method to treat cancer. The method includes the steps of: (a) administering to an individual who has cancer in which Brachyury expression has not been detected, a first immunotherapeutic composition comprising a yeast vehicle and a first cancer antigen that does not comprise a Brachyury antigen; and (b) administering to the individual, prior to, concurrently with, sequentially with, or subsequent to, administration of the first immunotherapeutic composition a second immunotherapeutic composition comprising a yeast vehicle and a second cancer antigen comprising a Brachyury antigen. In one aspect, the method further comprises, in step (a), administering one or more additional immunotherapeutic compositions, wherein the each of the one or more additional immunotherapeutic compositions comprises an additional cancer antigen. In one aspect of either embodiment above, the cancer antigen is selected from: mutated Ras, carcinoembryonic antigen (CEA), MUC-1, EGFR, BCR-Abl, MART-1, MAGE-1, MAGE-3, GAGE, GP-100, MUC-2, PSMA, tyrosinase, TRP-1 (gp75), NY-ESO-1, TRP-2, TAG72, KSA, CA-125, PSA, HER-2/neu/c-erb/B2, hTERT, p73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, and NGEP. In one aspect, the cancer antigen is selected from the group consisting of: mutated Ras, carcinoembryonic antigen (CEA), and MUC-1. Another embodiment of the invention relates to the use of a combination of immunotherapeutic compositions to treat cancer, the immunotherapeutic compositions comprising: (a) a first immunotherapeutic composition comprising a yeast vehicle and a first cancer antigen that does not comprise a Brachyury antigen; and (b) a second immunotherapeutic composition comprising a yeast vehicle and a second cancer antigen comprising a Brachyury antigen.

Yet another embodiment of the invention relates to a method treat cancer. The method includes the steps of: (a) administering to an individual who has cancer a first immunotherapeutic composition comprising a yeast vehicle and a mutated Ras antigen; (b) administering to the individual of (a) a second immunotherapeutic composition comprising a yeast vehicle and an antigen selected from the group consisting of carcinoembryonic antigen (CEA) and mucin-1 (MUC-1); and (c) administering to the individual of (a) and (b) a third immunotherapeutic composition comprising a yeast vehicle and a Brachyury antigen. In one aspect, the steps of administration in (a), (b) and (c) are concurrent. Another embodiment of the invention relates to the use of a combination of immunotherapeutic compositions to treat cancer, the immunotherapeutic compositions comprising: (a) a first immunotherapeutic composition comprising a yeast vehicle and a mutated Ras antigen; (b) a second immunotherapeutic composition comprising a yeast vehicle and an antigen selected from the group consisting of carcinoembryonic antigen (CEA) and mucin-1 (MUC-1); and (c) a third immunotherapeutic composition comprising a yeast vehicle and a Brachyury antigen.

In any of the embodiments or aspects of the invention described above or elsewhere herein, where the individual has cancer or a precancerous lesion, in one aspect of the invention, the individual is being treated or has been treated with another therapy for cancer. For example, such a therapy can include, but is not limited to, chemotherapy, targeted cancer therapy, radiation therapy, adoptive T cell transfer, and/or administration of one or more additional immunotherapeutic compositions. In one aspect, an additional immunotherapeutic composition comprises a yeast vehicle and a second cancer antigen that does not include Brachyury antigen. The second cancer antigen can include, but is not limited to, mutated Ras, carcinoembryonic antigen (CEA), MUC-1, EGFR, BCR-Abl, MART-1, MAGE-1, MAGE-3, GAGE, GP-100, MUC-2, PSMA, tyrosinase, TRP-1 (gp75), NY-ESO-1, TRP-2, TAG72, KSA, CA-125, PSA, HER-2/neu/c-erb/B2, hTERT, p73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, and NGEP. In one aspect, the second cancer antigen is selected from: mutated Ras, carcinoembryonic antigen (CEA), and MUC-1.

In one aspect of any of the embodiments or aspects of the invention described above or elsewhere herein, the method or use reduces tumor burden in the individual, increases survival of the individual, and/or inhibits tumor growth in the individual.

In one aspect of any of the embodiments or aspects of the invention described above or elsewhere herein, the method further comprises surgical resection of a tumor from the individual.

In one aspect of any of the embodiments or aspects of the invention described above or elsewhere herein, the cancer is of epithelial cell origin. In one aspect, the cancer can include, but is not limited to, breast cancer, small intestine cancer, stomach cancer, pancreatic cancer, kidney cancer, bladder cancer, uterine cancer, ovarian cancer, testicular cancer, lung cancer, colon cancer, prostate cancer, chronic lymphocytic leukemia (CLL), Epstein-Barr virus transformed B cells, Burkitt's lymphoma, Hodgkin's lymphoma, or metastatic cancers thereof.

In one aspect of any of the embodiments or aspects of the invention described above or elsewhere herein, the Brachyury antigen is full-length human Brachyury. In one aspect, the Brachyury antigen is not full-length Brachyury. In one aspect, the Brachyury antigen has an amino acid sequence represented by SEQ ID NO:6, SEQ ID NO:18, SEQ ID NO:2, or an amino acid sequence that is at least 95% identical to SEQ ID NO:6, SEQ ID NO:18, or SEQ ID NO:2. In one aspect, the Brachyury antigen comprises from at least position 1 or 2 to between position 255 and the C-terminus of SEQ ID NO:6, SEQ ID NO:18, or SEQ ID NO:2. In one aspect, the Brachyury antigen comprises from at least position 1 or 2 to between position 430 and the C-terminus of SEQ ID NO:6, SEQ ID NO:18, or SEQ ID NO:2. In one aspect, the Brachyury antigen comprises positions 246 to 254 of SEQ ID NO:6, SEQ ID NO:18, or SEQ ID NO:2. In one aspect, the Brachyury antigen comprises SEQ ID NO:6, positions 2-435 of SEQ ID NO:6, or an amino acid sequence that is at least 95% identical to SEQ ID NO:6. In one aspect, the Brachyury antigen comprises SEQ ID NO:18, positions 2-435 of SEQ ID NO:18, or an amino acid sequence that is at least 95% identical to SEQ ID NO:18. In one aspect, the Brachyury antigen comprises SEQ ID NO:2, positions 2-435 of SEQ ID NO:2, or an amino acid sequence that is at least 95% identical to SEQ ID NO:2. In one aspect, the Brachyury antigen comprises SEQ ID NO:6, positions 2-435 of SEQ ID NO:6, or an amino acid sequence that is at least 99% identical to SEQ ID NO:6. In one aspect, the Brachyury antigen comprises SEQ ID NO:18, positions 2-435 of SEQ ID NO:18, or an amino acid sequence that is at least 99% identical to SEQ ID NO:18. In one aspect, the Brachyury antigen comprises SEQ ID NO:2, positions 2-435 of SEQ ID NO:2, or an amino acid sequence that is at least 99% identical to SEQ ID NO:2. In one aspect, the cancer antigen is at least 25 amino acids in length. In one aspect, the Brachyury antigen is at least 25 amino acids in length. In one aspect, the Brachyury antigen is greater than 30 amino acids in length. In one aspect, the cancer antigen comprises two or more immunogenic domains of Brachyury.

In one aspect of any of the embodiments or aspects of the invention described above or elsewhere herein, the cancer antigen is a fusion protein. In one aspect, the fusion protein has an amino acid sequence represented by SEQ ID NO:8, or an amino acid sequence that is at least 95% identical to SEQ ID NO:8. In one aspect, the fusion protein has an amino acid sequence represented by SEQ ID NO:20, or an amino acid sequence that is at least 95% identical to SEQ ID NO:20.

Another embodiment of the invention relates to a yeast-Brachyury immunotherapeutic composition, wherein the immunotherapeutic composition comprises: (a) a yeast vehicle; and (b) an antigen expressed by the yeast vehicle and comprising at least one Brachyury antigen, wherein the Brachyury antigen comprises greater than 30 amino acids of an amino acid sequence represented by SEQ ID NO:6, SEQ ID NO:18 or SEQ ID NO:2. In one aspect, the Brachyury antigen comprises an amino acid sequence that is at least 95% identical to SEQ ID NO:6, SEQ ID NO:18 or SEQ ID NO:2. In one aspect, the Brachyury antigen comprises from at least position 1 or 2 to between position 255 and the C-terminus of SEQ ID NO:6, SEQ ID NO:18 or SEQ ID NO:2. In one aspect, the Brachyury antigen comprises from at least position 1 or 2 to between position 430 and the C-terminus of SEQ ID NO:6, SEQ ID NO:18 or SEQ ID NO:2. In one aspect, the Brachyury antigen comprises positions 246 to 254 of SEQ ID NO:6, SEQ ID NO:18 or SEQ ID NO:2. In one aspect, the Brachyury antigen comprises SEQ ID NO:6, positions 2-435 of SEQ ID NO:6, or an amino acid sequence that is at least 95% identical to SEQ ID NO:6. In one aspect, the Brachyury antigen comprises SEQ ID NO:18, positions 2-435 of SEQ ID NO:18, or an amino acid sequence that is at least 95% identical to SEQ ID NO:18. In one aspect, the Brachyury antigen comprises SEQ ID NO:2, positions 2-435 of SEQ ID NO:2, or an amino acid sequence that is at least 95% identical to SEQ ID NO:2. In one aspect, the Brachyury antigen comprises SEQ ID NO:6, positions 2-435 of SEQ ID NO:6, or an amino acid sequence that is at least 99% identical to SEQ ID NO:6. In one aspect, the Brachyury antigen comprises SEQ ID NO:18, positions 2-435 of SEQ ID NO:18, or an amino acid sequence that is at least 99% identical to SEQ ID NO:18. In one aspect, the Brachyury antigen comprises SEQ ID NO:2, positions 2-435 of SEQ ID NO:2, or an amino acid sequence that is at least 99% identical to SEQ ID NO:2. In one aspect, the cancer antigen is a fusion protein. In one aspect, the fusion protein has an amino acid sequence that is SEQ ID NO:8 or an amino acid sequence that is at least 95% identical to SEQ ID NO:8. In one aspect, the fusion protein has an amino acid sequence of SEQ ID NO:20 or an amino acid sequence that is at least 95% identical to SEQ ID NO:20. In one aspect, the yeast vehicle is a whole yeast. In one aspect, the whole yeast is heat-inactivated.

Yet another embodiment of the invention relates to a yeast-Brachyury immunotherapeutic composition comprising: (a) a whole, inactivated yeast; and (b) a Brachyury fusion protein comprising the amino acid sequence of positions 2-435 of SEQ ID NO:6. The expression of the Brachyury fusion protein is under the control of the promoter CUP1, the Brachyury fusion protein is expressed by the yeast, and the composition elicits a Brachyury-specific T cell response. In one aspect, the fusion protein comprises the amino acid sequence of SEQ ID NO:8.

Yet another embodiment of the invention relates to a yeast-Brachyury immunotherapeutic composition comprising: (a) a whole, inactivated yeast; and (b) a Brachyury fusion protein comprising the amino acid sequence of positions 2-435 of SEQ ID NO:18. The expression of the Brachyury fusion protein is under the control of the promoter CUP1, the Brachyury fusion protein is expressed by the yeast, and the composition elicits a Brachyury-specific T cell response. In one aspect, the fusion protein comprises the amino acid sequence of SEQ ID NO:20.

In one aspect of any of the embodiments or aspects of the invention described above or elsewhere herein, the yeast vehicle is a whole yeast. In one aspect, the whole yeast is killed. In one aspect, the whole yeast is heat-inactivated. In one aspect, the yeast expresses the antigen. In one aspect, the yeast is from a genus selected from the group consisting of: *Saccharomyces, Candida, Cryptococcus, Hansenula, Kluyveromyces, Pichia, Rhodotorula, Schizosaccharomyces* and *Yarrowia*. In one aspect, the yeast is from *Saccharomyces*. In one aspect, the yeast is from *Saccharomyces cerevisiae*.

In one aspect of any of the embodiments of the invention described above or elsewhere herein, the composition is formulated in a pharmaceutically acceptable excipient suitable for administration to a subject.

Yet another embodiment of the invention relates to the use of any of the yeast-Brachyury immunotherapeutic compositions described herein to treat a disease. In one aspect, the disease is cancer. In one aspect, the disease is associated with an infectious agent. In one aspect, the disease is associated with a virus or viral infection. Such a virus can include, but is not limited to, Epstein Barr Virus (EBV).

Another embodiment of the invention relates to a method to treat or prevent a disease or condition associated with Epstein Barr Virus (EBV) infection. The method includes the step of administering to an individual any of the yeast-Brachyury immunotherapeutic compositions described herein.

Yet another embodiment of the invention relates to a method to produce a yeast-Brachyury immunotherapeutic composition. The method includes the steps of: (a) culturing yeast that have been transformed with a recombinant nucleic acid molecule encoding a Brachyury antigen under the control of a CUP1 promoter in a suitable medium in the absence of $CuSO_4$ until the yeast reach mid-log growth phase; (b) inducing expression of the Brachyury antigen in the yeast by adding $CuSO_4$ to the medium; (c) culturing the yeast after step (b) for up to between 6 and 8 hours; and (d) harvesting the yeast. In one aspect, the yeast in step (a) are cultured to a cell density of between 1.0 and 2.0 Y.U. per milliliter total culture volume. In one aspect, the yeast in step (a) are cultured to a cell density of between 1.0 and 1.5 Y.U. per milliliter total culture volume. In one aspect, the yeast are cultured in steps (a)-(c) in a medium where the pH is maintained at pH 5.5 or higher. In one aspect, the method additionally includes a step of heat-inactivating the yeast after step (d). For example, in one aspect, the yeast are heat-inactivated at about 56° C. for about 1 hour. In a further aspect of this embodiment, the yeast can be formulated for injection with a pharmaceutically acceptable excipient. In one aspect, the yeast are from *Saccharomyces*. In one aspect, the yeast are from *Saccharomyces cerevisiae*.

BRIEF DESCRIPTION OF THE DRAWINGS

FIGS. 3A-3C are graphs showing that peripheral blood mononuclear cells (PBMCs) from two out of three healthy donors pulsed with yeast-Brachyury for two cycles of stimulation, followed by pulsing with Brachyury CTL peptide, were capable of generating $CD8^-$ CTLs that could kill SW480 carcinoma cells (HLA-A2 positive/Brachyury high), with minimal lysis of MCF7 carcinoma (HLA-A2 positive/Brachyury low); (FIG. 3A, donor 07706; FIG. 3B, donor 17663; FIG. 3C, donor 26532).

FIG. 5 is a graph showing proliferation of $CD4^+$ T cells isolated from the spleen of mice that were vaccinated with yeast-Brachyury (GI-6301, circles) or control yeast (Yeast control, triangles), in response to indicated doses of purified Brachyury protein or control β-gal protein.

DETAILED DESCRIPTION OF THE INVENTION

Figure 1B:
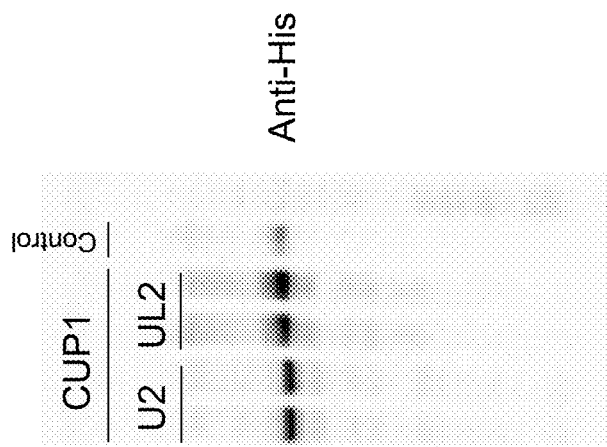
FIG. 1B is a digitized image of a Western blot showing detection by anti-His of expression of Brachyury in a yeast-Brachyury immunotherapeutic composition, with both U2 and UL2 media.

This invention generally relates to yeast-based immunotherapeutic compositions and methods for the prevention and/or treatment of cancers that express or overexpress Brachyury. The invention includes the use of a yeast-based immunotherapeutic composition (also referred to as yeast-based immunotherapy) comprising a yeast vehicle and Brachyury antigens or immunogenic domains thereof (also referred to herein as "yeast-Brachyury immunotherapy" or "yeast-Brachyury immunotherapeutic compositions"). The inventors describe herein the construction and production of novel yeast-Brachyury immunotherapy products, and demonstrate that yeast-Brachyury immunotherapy expands Brachyury-specific T cells, including $CD8^+$ CTLs, from normal individuals and from cancer patients. In addition, mice immunized with yeast-Brachyury immunotherapeutic compositions generated Brachyury-specific T cell responses in vivo, and Brachyury-expressing tumor growth was inhibited in these mice. Taken together, the data presented herein show that yeast-Brachyury immunotherapy is useful for the elicitation of Brachyury-specific cellular immune responses ($CD4^+$ and $CD8^+$) and for the prevention and treatment of Brachyury-expressing tumors, offering novel therapy for the prevention and/or treatment of metastatic cancers and associated conditions.

Yeast-Brachyury immunotherapeutic compositions useful in the present invention are uniquely adapted to effectively target Brachyury-expressing cancers for several reasons. First, Brachyury is involved in EMT processes, and therefore, without being bound by theory, the inventors believe that it plays a role in late-stage tumors and metastatic processes. Accordingly, in one aspect of the invention, yeast-Brachyury immunotherapy is effective at targeting tumor cells before or at the time during which they begin to acquire motility and invade other tissues, thereby preventing, inhibiting, arresting, reversing or delaying the onset of metastatic cancer and/or the progression of cancer, and especially metastatic cancer. There is a great need for effective therapies for late stage cancers, especially metastatic cancers, which may have few options for treatment once conventional cancer therapy has failed. Yeast-Brachyury presents a novel approach to treat such cancers, or to delay, inhibit, reverse, or prevent them altogether. In addition, yeast-Brachyury immunotherapy can be used to prevent or delay metastatic cancer or progression of cancer in individuals who have early stage cancer. The therapy is useful, in one embodiment, in cancers that have a high rate of metastatic progression, and may be useful to arrest progression of the cancer. Furthermore, yeast-Brachyury immunotherapy is useful in individuals who have a precancerous (pre-malignant) lesion or tumor, in individuals who are at a high risk for developing a cancer, particularly one that has a high rate of metastases, and even in normal individuals as a prophylactic agent for the prevention of cancer, which may be used in conjunction with other prophylactic immunotherapy for cancer, such as described herein.

Yeast-Brachyury immunotherapy also provides a benefit to individuals who are undergoing other therapy for cancer, including chemotherapy and radiation therapy. More particularly, metastatic cancers are known in some cases to be more resistant to chemotherapy and/or radiation therapy than the primary cancers. Therefore, the yeast-Brachyury immunotherapy compositions of the invention can be used to inhibit or reduce or eliminate chemotherapy resistance or radiation resistance that may occur in metastatic cancer by inhibiting Brachyury expression in the cancer (and thereby inhibiting anti-proliferative influences), and compositions of the invention may enhance the performance of chemotherapy or radiation therapy in an individual.

Yeast-Brachyury immunotherapy can also be used to treat conditions or diseases associated with Brachyury expression that may be non-oncological in nature, or that may precede malignant transformation. For example, Brachyury may be upregulated in cells that are infected with an infectious agent, e.g., a virus such as Epstein Barr Virus (EBV). Accordingly, yeast-Brachyury immunotherapy can be used to treat or prevent any disease or condition associated with Brachyury expression, including, but not limited to, infectious diseases, such as viral infection, including, but not limited to, EBV-associated conditions (e.g., mononucleosis).

Yeast-Brachyury immunotherapy is also readily adaptable to the use of additional tumor antigens within the same yeast composition, or to use in combination with other yeast-based immunotherapeutics that target other tumor antigens (sequentially or concurrently) or other immunotherapeutics and treatments/therapies for cancer. Accordingly, the yeast-Brachyury immunotherapy can be adapted to the cancer type, the cancer stage, the cancer grade, the antigens expressed by the tumor, and the overall medical status of the individual (i.e., the therapy is easily personalized), and for the individual who already has cancer, its use can be modified as cancer progresses in an individual, in order to provide maximum efficacy at a variety of tumor stages. Yeast-Brachyury immunotherapy offers the opportunity to design sophisticated and effective, individualized approaches for the broad-based prophylactic and/or therapeutic treatment of a wide range of cancers.

Yeast-Brachyury compositions described herein induce innate immune responses, as well as adaptive immune responses against the target antigen (Brachyury), including CD4-dependent TH17 and TH1 T cell responses and antigen-specific $CD8^+$ T cell responses, which include cytotoxic T lymphocyte (CTL) responses, all without the use of exogenous adjuvants, cytokines, or other immunostimulatory molecules, many of which have toxicity issues. In addition, yeast-Brachyury immunotherapeutic compositions inhibit regulatory T cell (Treg) numbers and/or functionality, thereby enhancing effector T cell responses that might normally be suppressed by the presence of the tumor, for example. Moreover, as compared to immunotherapeutic compositions that immunize by generating antibody responses, the antigen-specific, broad-based, and potent cellular immune responses elicited by yeast-Brachyury immunotherapy are believed to be particularly effective in targeting tumor cells. Indeed, numerous studies have shown that immunotherapeutic approaches are enhanced when tumor cells are targeted via $CD8^+$ CTLs which recognize tumor peptides in the context of MHC Class I molecules.

Yeast-Brachyury immunotherapy is highly adept at activating antigen presenting cells, and has a unique ability to cross-prime the immune response, generating $CD8^+$ CTL responses that are typically effective against tumors, even in the face of what may otherwise be a suppressive environment. Since this type of immunotherapy utilizes the natural ability of the antigen presenting cell to present relevant immunogens, it is not necessary to know the precise identity of CTL epitopes or MHC Class II epitopes of Brachyury to produce an effective immunotherapeutic according to the present invention. In fact, multiple $CD4^+$ and $CD8^+$ T cell epitopes can be targeted in a single yeast-Brachyury immunotherapeutic composition, and so the yeast-Brachyury immunotherapeutics of the invention are not limited to the use of short peptides and in fact, the use of longer polypeptides and fusion proteins in these compositions is efficacious. Accordingly, by using yeast-Brachyury immunotherapy, the use of algorithms and complex formulas to identify putative T cell epitopes is eliminated.

Furthermore, since Brachyury is not expressed by most normal (non-tumor) tissues, and is typically over-expressed in tumor cells, any "off target" effects related to normal tissues are not of concern. As mentioned above, yeast-Brachyury can be effectively utilized in an immunization protocol (prophylactic or therapeutic) without the use of exogenous adjuvants, immunostimulatory agents or molecules, costimulatory molecules, or cytokines, although such agents may be included, if desired. Moreover, yeast-Brachyury immunotherapy can be administered repeatedly without losing efficacy, as may be problematic with other types of immunotherapy.

Compositions of the Invention

One embodiment of the present invention relates to a yeast-based immunotherapy composition which can be used to prevent and/or treat cancers characterized by Brachyury expression or overexpression (including cancers that may not contain cells expressing detectable Brachyury initially, but which may or will contain cells expressing Brachyury at later stages of the development of the cancer). The composition is a yeast-Brachyury immunotherapeutic composition comprising: (a) a yeast vehicle; and (b) a cancer antigen comprising one or more Brachyury antigen(s) and/or immunogenic domain(s) thereof. The Brachyury antigen or immunogenic domain thereof is most typically expressed as a recombinant protein by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more Brachyury antigens are loaded into a yeast vehicle or otherwise complexed with, attached to, mixed with or administered with a yeast vehicle as described herein to form a composition of the present invention.

A "yeast-Brachyury immunotherapeutic composition" is a specific type of "yeast-based immunotherapeutic composition" that contains at least one Brachyury antigen or immunogenic domain thereof. The phrase, "yeast-based immunotherapeutic composition" may be used interchangeably with "yeast-based immunotherapy product", "yeast-based immunotherapy composition", "yeast-based composition", "yeast-based immunotherapeutic", "yeast-based vaccine", or derivatives of these phrases. An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and typically, an antigen component, and can elicit or induce an immune response, such as a cellular immune response, including without limitation a T cell-mediated cellular immune response. In one aspect, a yeast-based immunotherapeutic composition useful in the invention is capable of inducing a $CD8^+$ and/or a $CD4^+$ T cell-mediated immune response and in one aspect, a $CD8^+$ and a $CD4^+$ T cell-mediated immune response, particularly against a target antigen (e.g., a cancer antigen). A $CD4^+$ immune response can include TH1 immune responses, TH2 immune responses, TH17 immune responses, or any combination of the above. Yeast-based immunotherapeutics are particularly capable of generating TH1 and TH17 responses. A $CD8_+$ immune response can include a cytotoxic T lymphocyte (CTL) response, and yeast-based immunotherapeutics are capable of generating such responses. In one aspect, a yeast-based immunotherapeutic composition modulates the number and/or functionality of regulatory T cells (Tregs) in a subject. Yeast-based immunotherapy can also be modified to promote one type of response over another, e.g., by the addition of cytokines, antibodies, and/or modulating the manufacturing process for the yeast. Optionally, a yeast-based immunotherapeutic composition is capable of eliciting a humoral immune response.

Yeast-Brachyury immunotherapeutic compositions of the invention may be either "prophylactic" or "therapeutic". When provided prophylactically, the compositions of the present invention are provided in advance of the development of, or the detection of the development of, a cancer that expresses Brachyury, with the goal of preventing, inhibiting or delaying the development of Brachyury-expressing tumors; and/or preventing, inhibiting or delaying tumor migration and/or tumor invasion of other tissues (metastases) and/or generally preventing or inhibiting progression of cancer in an individual. As discussed herein, Brachyury is expressed in several cancers, including late-stage cancers, and has been shown to be involved in the EMT process, which is a process associated with invasiveness and migration of tumors, such as in metastatic cancer. Therefore, prophylactic compositions can be administered to individuals that appear to be cancer-free (healthy, or normal, individuals), to individuals with pre-cancerous (pre-malignant lesions), and also to individuals who have cancer, but in which Brachyury has not yet been detected (i.e. prior to the expression of Brachyury by tumor cells in the cancer). Individuals who are at high risk for developing a cancer, particularly a cancer with which Brachyury expression and/or metastases are typically associated, may be treated prophylactically with a composition of the invention. When provided therapeutically, the immunotherapy compositions are provided to an individual with a Brachyury-expressing cancer, with the goal of ameliorating the cancer, such as by reducing tumor burden in the individual; inhibiting tumor growth in the individual; increasing survival of the individual; preventing, inhibiting, reversing or delaying development of tumor migration and/or tumor invasion of other tissues (metastatic cancer) and/or preventing, inhibiting, reversing or delaying progression of the cancer in the individual. In one aspect, yeast-Brachyury immunotherapy is used therapeutically to inhibit, reduce or eliminate chemotherapy resistance or radiation resistance that may occur in metastatic cancer by inhibiting Brachyury expression in the cancer, and compositions of the invention may enhance the performance of chemotherapy or radiation therapy in an individual.

Typically, a yeast-Brachyury immunotherapy composition includes a yeast vehicle and at least one cancer antigen comprising a Brachyury antigen or immunogenic domain thereof, where the cancer antigen is expressed by, attached to, loaded into, or mixed with the yeast vehicle. In some embodiments, the cancer antigen, Brachyury antigen, or immunogenic domain thereof is provided as a fusion protein. Several Brachyury proteins and fusion proteins suitable for use in the compositions and methods of the invention are described below. In some embodiments, the cancer antigen and the Brachyury antigen are the same element. In some embodiments, the cancer antigen includes other antigens, including other cancer antigens, in addition to the Brachyury antigen. In one aspect of the invention, a fusion protein useful as a cancer antigen can include two or more antigens, e.g., a Brachyury antigen and another cancer antigen that is not a Brachyury antigen, or two different Brachyury antigens. In one aspect, the fusion protein can include two or more immunogenic domains of one or more antigens, such as two or more immunogenic domains of a Brachyury antigen, or two or more epitopes of one or more antigens, such as two or more epitopes of a Brachyury antigen.

According to the present invention, a yeast vehicle used in a yeast-Brachyury immunotherapy composition is any yeast cell (e.g., a whole or intact cell) or a derivative thereof (see below) that can be used in conjunction with one or more antigens, immunogenic domains thereof or epitopes thereof in a composition of the invention (e.g., a therapeutic or prophylactic composition). The yeast vehicle can therefore include, but is not limited to, a live intact (whole) yeast microorganism (i.e., a yeast cell having all its components including a cell wall), a killed (dead) or inactivated intact yeast microorganism, or derivatives of intact yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces*, *Candida* (which can be pathogenic), *Cryptococcus*, *Hansenula*, *Kluyveromyces*, *Pichia*, *Rhodotorula*, *Schizosaccharomyces* and *Yarrowia*. In one aspect, yeast genera are selected from *Saccharomyces*, *Candida*, *Hansenula*, *Pichia* or *Schizosaccharomyces*, and in one aspect, *Saccharomyces* is used. Species of yeast strains that may be used in the invention include but are not limited to *Saccharomyces cerevisiae*, *Saccharomyces carlsbergensis*, *Candida albicans*, *Candida kefyr*, *Candida tropicalis*, *Cryptococcus laurentii*, *Cryptococcus neoformans*, *Hansenula anomala*, *Hansenula polymorpha*, *Kluyveromyces fragilis*, *Kluyveromyces lactis*, *Kluyveromyces marxianus* var. *lactis*, *Pichia pastoris*, *Rhodotorula rubra*, *Schizosaccharomyces pombe*, and *Yarrowia hpolytica*. It is to be appreciated that a number of these species include a variety of subspecies, types, subtypes, etc. that are intended to be included within the aforementioned species. In one aspect, yeast species used in the invention include *S. cerevisiae*, *C. albicans*, *H. polymorpha*, *P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir$^o$ strain. The *S. cerevisiae* strain is one such strain that is capable of supporting expression vectors that allow one or more target antigen(s) and/or antigen fusion protein(s) and/or other proteins to be expressed at high levels. Another yeast strain is useful in the invention is *Saccharomyces cerevisiae* W303α. In addition, any mutant yeast strains can be used in the present invention, including those that exhibit reduced post-translational modifications of expressed target antigens or other proteins, such as mutations in the enzymes that extend N-linked glycosylation.

The yeast-Brachyury immunotherapy composition of the invention includes at least one cancer antigen comprising a Brachyury antigen. According to the present invention, the general use herein of the term "antigen" refers: to any portion of a protein (e.g., peptide, partial protein, full-length protein), wherein the protein is naturally occurring or synthetically derived or designed, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-11 amino acids (i.e., a peptide) and as large as: a full length protein, a multimer, a fusion protein, a chimeric protein, a whole cell, a whole microorganism, or any portions thereof (e.g., protein fragments (polypeptides) lysates of whole cells or extracts of microorganisms). Antigens useful in the yeast-Brachyury immunotherapeutic of the present invention are peptides, polypeptides, full-length proteins, multimers, fusion proteins and chimeric proteins. In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism. For expression in yeast, an antigen is of a minimum size capable of being expressed recombinantly in yeast if the antigen is the entire protein to be expressed by the yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or at least or greater than 25-50 amino acids in length, or at least or greater than 30-50 amino acids in length, or at least or greater than 35-50 amino acids in length, or at least or greater than 40-50 amino acids in length, or at least or greater than 45-50 amino acids in length, although smaller proteins may be expressed, and considerably larger proteins (e.g., hundreds of amino acids in length or even a few thousand amino acids in length) may be expressed. In one aspect, a full-length protein or a protein that is lacking between 1 and 20 amino acids from the N- and/or the C-terminus may be expressed. Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). A "cancer antigen" is an antigen that comprises at least one antigen that is associated with a cancer such as an antigen expressed by a tumor cell, such that targeting the antigen also targets the cancer. A cancer antigen can include one or more antigens from one or more proteins, including one or more tumor-associated proteins. A "Brachyury antigen" is an antigen derived, designed, or produced from a Brachyury protein.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a CD4$^+$ T cell response (e.g., TH1, TH2 and/or TH17) and/or a CD8$^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MEW molecules bound by the epitope. Epitopes can be linear sequence epitopes or conformational epitopes (conserved binding regions). Most antibodies recognize conformational epitopes.

Brachyury (which may also be referred to as "T") is a highly conserved protein among multiple different animal species and is a transcription factor that contains a "T-box" domain or "T-domain", a DNA-binding domain motif shared among several different proteins, collectively called the T-box family of proteins. Human Brachyury was first cloned in 1996 (Edwards et al., supra). One nucleotide sequence encoding human Brachyury is represented herein by SEQ ID NO:1, which is an mRNA sequence that was obtained from GENBANK® Accession No. NM_003181 (GI:19743811). SEQ ID NO:1 encodes a 435 amino acid human Brachyury protein, the amino acid sequence of which is represented here as SEQ ID NO:2 (also found in GENBANK® Accession No. NP_003172; GI:4507339).

Another human Brachyury protein disclosed herein is a variant of the human Brachyury protein represented by SEQ ID NO:2, and has the amino acid sequence of SEQ ID NO:6. SEQ ID NO:6, also a 435 amino acid protein, is encoded by a nucleotide sequence represented herein by SEQ ID NO:5. SEQ ID NO:6 is approximately 99% identical to SEQ ID NO:2 over the full-length of the protein. SEQ ID NO:6 differs from SEQ ID NO:2 at position 177 (Asp vs. Gly, respectively), position 368 (Thr vs. Ser, respectively) and position 409 (Asn vs. Asp, respectively).

Another human Brachyury protein disclosed herein is an agonist of the human Brachyury protein represented by SEQ ID NO:2 or SEQ ID NO:6. As generally used herein, an "agonist" is any compound or agent, including without limitation small molecules, proteins, peptides, antibodies, nucleic acid binding agents, etc., that binds to a receptor or ligand and produces or triggers a response, which may include agents that mimic or enhance the action of a naturally occurring substance that binds to the receptor or ligand. When used in the context of a Brachyury antigen of the invention, an "agonist" antigen or protein refers to an antigen or protein that comprises at least one T cell agonist epitope, which may also be referred to as a "mimotope". A mimotope peptide is a peptide that mimics the structure of a wild-type epitope and as an agonist, the mimotope mimics or enhances the action (biological function) of the natural epitope. For example, the amino acid sequence of SEQ ID NO:12 (WLLPGTSTL) is a T cell epitope of a wild-type Brachyury protein. The amino acid sequence of SEQ ID NO:13 (WLLPGTSTV) is a mimotope or agonist of the T cell epitope of SEQ ID NO:12.

One human Brachyury agonist antigen is represented here by SEQ ID NO:18. SEQ ID NO:18 is a 435 amino acid protein is encoded by a nucleotide sequence represented herein by SEQ ID NO:17. SEQ ID NO:18 is identical to SEQ ID NO:6, except for a substitution of a leucine at position 254 with respect to SEQ ID NO:6 with a valine in SEQ ID NO:18. This substitution creates a T cell agonist epitope in SEQ ID NO:18 at positions 246 to 254 that, without being bound by theory, is believed to induce enhanced T cell responses against Brachyury as compared to the wild-type epitope (positions 246 to 254 of SEQ ID NO:6).

Positions 41 to 223 of any of SEQ ID NO:2, SEQ ID NO:6 or SEQ ID NO:18 represent the T-box DNA binding domain of human Brachyury, and the T-box domain in other Brachyury sequences, including Brachyury sequences from other species, can be readily identified by comparison to these sequences. As used herein, reference to a T-box domain of any Brachyury protein described herein or known in the art and utilized in the invention may include an additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 consecutive amino acids of the Brachyury sequence on the N-terminal and/or the C-terminal end of the defined T-box domain (e.g., on either side of positions 41-223 of SEQ ID NOs:2, 6 or 18). Human Brachyury, including the two human Brachyury proteins described herein, also contains various CD4$^+$ and CD8$^+$ T cell epitopes. Such epitopes have been described, for example, in WO 2008/106551, and include a CD8$^+$ CTL epitope, WLLPGTSTL (also referred to herein as Tp2, SEQ ID NO:12), at positions 246 to 254 of SEQ ID NO:2 or SEQ ID NO:6. As discussed above, SEQ ID NO:18 comprises an agonist epitope of SEQ ID NO:12, represented herein by SEQ ID NO:13.

Human Brachyury has very high homology with Brachyury from other animal species and therefore, one is able to utilize the sequences of Brachyury from other organisms in the preparation of a yeast-Brachyury immunotherapeutic composition of the invention, particularly where these sequences are identical, substantially homologous, and elicit an effective immune response against the target antigen (e.g., native Brachyury expressed by a tumor cell). For example, murine Brachyury, which was first cloned by Hermann and colleagues in 1990 (Hermann et al., supra) is approximately 85% identical to human Brachyury at the nucleotide level, and approximately 91% identical at the amino acid level. With respect to Brachyury from other animals, at the amino acid level, human Brachyury is 99.5% identical to Brachyury from *Pan troglodytes,* 90.1% identical to Brachyury from *Canis lupus familiaris,* 88.5% identical to Brachyury from *Bos Taurus,* 92.2% identical to Brachyury from *Rattus norvegicus,* and 80.9% identical to Brachyury from *Gallus gallus.* Within amino acids 1-223 of Brachyury, which contains the T-box domain, mouse and human Brachyury differ by only two amino acids (at positions 26 and 96). A nucleotide sequence encoding murine Brachyury is represented herein by SEQ ID NO:3, which is an mRNA sequence that was obtained from GENBANK® Accession No. NM_009309 (GI:118130357). SEQ ID NO:3 encodes a 436 amino acid murine Brachyury protein, the amino acid sequence of which is represented here as SEQ ID NO:4. Positions 41 to 223 of SEQ ID NO:4 represent the T-box DNA binding domain of murine Brachyury.

In one embodiment of the invention, a Brachyury antigen comprises or consists of the amino acid sequence represented by SEQ ID NO:2, SEQ ID NO:4, SEQ ID NO:6, SEQ ID NO:18, or at least one immunogenic domain thereof. In one embodiment, a Brachyury antigen comprises or consists of two, three, four, five, or more immunogenic domains of Brachyury. In one embodiment of the invention, a Brachyury antigen comprises or consists of the amino acid sequence represented by amino acid positions 1 or 2 through one of the last 25 amino acids at the C-terminus of SEQ ID NO:2, SEQ ID NO:4, SEQ ID NO:6 or SEQ ID NO:18 (i.e., through any one of positions 441 to 435 of SEQ ID NO:2 or SEQ ID NO:6 or SEQ ID NO:18, or through any one of positions 442 to 436 of SEQ ID NO:4). Another Brachyury antigen useful in the invention also includes at least amino acid positions 1-223 of Brachyury (e.g., positions 1-223 of SEQ ID NO:2, SEQ ID NO:4, SEQ ID NO:6 or SEQ ID NO:18) or positions 41-223 of Brachyury (e.g., positions 41-223 of SEQ ID NO:2, SEQ ID NO:4, SEQ ID NO:6 or SEQ ID NO:18). Another Brachyury antigen useful in the invention includes from at least amino acid positions 1 to 85 to between position 255 and the C-terminus of SEQ ID NO:2, SEQ ID NO:4, SEQ ID NO:6 or SEQ ID NO:18. Another Brachyury antigen useful in the invention includes from at least amino acid positions 1 to 85 to between position 430 and the C-terminus of SEQ ID NO:2, SEQ ID NO:4, SEQ ID NO:6 or SEQ ID NO:18. Another Brachyury antigen useful in the invention includes from at least amino acid positions 1, 2, 3, 4, 5, 6, 7, 8, 9 or 10 to between position 255 and the C-terminus of SEQ ID NO:2, SEQ ID NO:4, SEQ ID NO:6 or SEQ ID NO:18.

According to any embodiment of the present invention, reference to a "full-length" protein (or a full-length functional domain or full-length immunological domain) includes the full-length amino acid sequence of the protein or functional domain or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. By way of example, several of the fusion proteins described herein comprise a "near full-length" Brachyury antigen since the antigen omits the methionine at position 1 and substitutes an N-terminal peptide. General reference to a protein or domain or antigen can include both full-length and near full-length proteins, as well as other homologues thereof.

In one aspect of any embodiments related to a Brachyury antigen, a cancer antigen or a Brachyury antigen is of a minimum size sufficient to allow the antigen to be expressed by yeast. For expression in yeast, a protein is typically at least about 25 amino acids in length, although smaller proteins may be expressed, and considerably larger proteins may be expressed by yeast. For example, a Brachyury antigen useful in the invention is a fragment of a Brachyury protein that can be expressed recombinantly by yeast and that contains at least one immunogenic domain of Brachyury, which could include at least one immunogenic domain of any of SEQ ID NO:2, SEQ ID NO:4, SEQ ID NO:6 or SEQ ID NO:18. In one aspect, such an antigen is at least 25 amino acids in length, and contains at least one immunogenic domain of Brachyury. In one aspect, such an antigen is greater than 30 amino acids in length, and contains at least one immunogenic domain of Brachyury. In one aspect, such an antigen is at least 25-50 amino acids in length, and contains at least one immunogenic domain of Brachyury. In one aspect, such an antigen is at least 30-50 amino acids in length, and contains at least one immunogenic domain of Brachyury. In one aspect, such an antigen is at least 35-50 amino acids in length, and contains at least one immunogenic domain of Brachyury. In one aspect, such an antigen is at least 40-50 amino acids in length, and contains at least one immunogenic domain of Brachyury. In one aspect, such an antigen is at least 45-50 amino acids in length, and contains at least one immunogenic domain of Brachyury. In one embodiment, the Brachyury antigen useful in the present invention is at least 25 amino acids in length, or at least: 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, or 430 amino acids in length, which can include any fragment of at least any of these lengths of SEQ ID NO:2, SEQ ID NO:4, SEQ ID NO:6 or SEQ ID NO:18.

In one aspect, a Brachyury antigen comprises one or more CTL epitopes, which may include two or more copies of any one, two, three, or more of the CTL epitopes described herein. In one aspect, the Brachyury antigen comprises one or more CD4+ T cell epitopes. The T cell In one aspect, the Brachyury antigen comprises one or more CTL epitopes and one or more CD4+ T cell epitopes. In one aspect, the T cell epitope is an agonist epitope.

In one aspect, a Brachyury antigen comprises an amino acid sequence of WLLPGTSTL (SEQ ID NO:12, also represented by positions 245 to 254 of SEQ ID NO:2 or SEQ ID NO:6). In one aspect, the Brachyury antigen comprises an amino acid sequence of WLLPGTSTV (SEQ ID NO:13, also represented by positions 245 to 254 of SEQ ID NO:18). In one aspect, the amino acid at position 4 of either SEQ ID NO:12 or SEQ ID NO:13 (a proline or P in these sequences) is substituted with a serine (S), a threonine (T), an isoleucine (I), or a valine (V).

In one aspect, the Brachyury antigen comprises an amino acid sequence of SQYPSLWSV (SEQ ID NO:14). In one aspect, the amino acid at position 2 of SEQ ID NO:14 (a glutamine or Q in this sequence) is substituted with a leucine (L). In one aspect, the amino acid at position 4 of SEQ ID NO:14 (a proline or P in this sequence) is substituted with a serine (S), threonine (T), leucine (L), or valine (V). In one aspect, the amino acid at position 7 of SEQ ID NO:14 (a tryptophan or W in this sequence) is substituted with a valine (V), leucine (L), isoleucine (I), serine (S), or threonine (T). In one aspect, the amino acid at position 9 of SEQ ID NO:14 (a valine or V in this sequence) is substituted with a leucine (L). An antigen comprising a sequence having any combination of one or more of these substitutions in SEQ ID NO:14 is contemplated by the invention.

In one aspect, the Brachyury antigen comprises an amino acid sequence of RLIASWTPV (SEQ ID NO:15). In one aspect, the amino acid at position 1 of SEQ ID NO:15 (an arginine or R in this sequence) is substituted with a tyrosine (Y) or a tryptophan (W). In one aspect, the amino acid at position 6 of SEQ ID NO:15 (a tryptophan or W in this sequence) is substituted with a valine (V), a lysine (L), an isoleucine (I), a serine (S), or a threonine (T). An antigen comprising a sequence having any combination of one or both of these substitutions in SEQ ID NO:15 is contemplated by the invention.

In one aspect, the Brachyury antigen comprises an amino acid sequence of AMYSFLLDFV (SEQ ID NO:16). In one aspect, the amino acid at position 2 of SEQ ID NO:16 (a methionine or M in this sequence) is substituted with a leucine (L).

In one embodiment of the invention, a Brachyury antigen comprises, consists essentially of, or consists of a fusion protein having the amino acid sequence of SEQ ID NO:8. The fusion protein of SEQ ID NO:8 is a single polypeptide with the following sequence elements fused in frame from N- to C-terminus: (1) an N-terminal peptide to impart resistance to proteasomal degradation and stabilize expression in yeast (positions 1-6 of SEQ ID NO:8); (2) a human Brachyury antigen consisting of positions 2-435 of SEQ ID NO:6 (positions 7-440 of SEQ ID NO:8); and (3) a hexahistidine tag (positions 441-446 of SEQ ID NO:8). The amino acid sequence of SEQ ID NO:8 is encoded by the polynucleotide sequence of SEQ ID NO:7.

In another embodiment of the invention, a Brachyury antigen comprises, consists essentially of, or consists of a fusion protein having the amino acid sequence of SEQ ID NO:10. The fusion protein of SEQ ID NO:10 is a single polypeptide with the following sequence elements fused in frame from N- to C-terminus: (1) an N-terminal peptide to impart resistance to proteasomal degradation and stabilize expression in yeast (positions 1-6 of SEQ ID NO:10); (2) a murine Brachyury antigen consisting of positions 2-436 of SEQ ID NO:4 (positions 7-441 of SEQ ID NO:10); and (3) a hexahistidine tag (positions 442-447 of SEQ ID NO:10). The amino acid sequence of SEQ ID NO:10 is encoded by the polynucleotide sequence of SEQ ID NO:9.

In another embodiment of the invention, a Brachyury antigen comprises, consists essentially of, or consists of a fusion protein having the amino acid sequence of SEQ ID NO:20. The fusion protein of SEQ ID NO:20 is a single polypeptide with the following sequence elements fused in frame from N- to C-terminus: (1) an N-terminal peptide to impart resistance to proteasomal degradation and stabilize expression (positions 1 to 6 of SEQ ID NO:20, the peptide sequence also represented herein by SEQ ID NO:11); 2) amino acids 2-435 of SEQ ID NO:18 (positions 7-440 of SEQ ID NO:20), SEQ ID NO:18 representing a full-length human Brachyury agonist protein; and (3) a hexahistidine tag (positions 441-446 of SEQ ID NO:20). The agonist epitope (SEQ ID NO:13) is located at positions 251 to 259 of SEQ ID NO:20 (positions 246 to 254 of SEQ ID NO:18). The amino acid sequence of SEQ ID NO:20 is encoded by the polynucleotide sequence of SEQ ID NO:19.

A Brachyury antigen useful in the present invention also includes proteins having an amino acid sequence that is at least 85%, 86%, 87%, 88%, 89%, 90%, 91%, 92%, 93%, 94%, 95%, 96%, 97%, 98%, or 99% identical to the amino acid sequence of any of the Brachyury proteins or antigens described herein over the full length of the protein, or with respect to a defined fragment or domain thereof (e.g., an immunological domain or functional domain (domain with at least one biological activity)) that forms part of the protein. For example, a domain of the Brachyury protein described herein includes the T-box domain. An immunological domain has been described in detail above.

In some aspects of the invention, amino acid insertions, deletions, and/or substitutions can be made for one, two, three, four, five, six, seven, eight, nine, ten, or more amino acids of a wild-type or reference Brachyury protein, provided that the resulting Brachyury protein, when used as an antigen in a yeast-Brachyury immunotherapeutic composition of the invention, elicits an immune response against a native Brachyury protein as the wild-type or reference Brachyury protein, which may include an enhanced immune response, a diminished immune response, or a substantially similar immune response. For example, the invention includes the use of Brachyury agonist antigens, which may include one or more T cell epitopes that have been mutated to enhance the T cell response against the Brachyury agonist, such as by improving the avidity or affinity of the epitope for an WIC molecule or for the T cell receptor that recognizes the epitope in the context of WIC presentation. Brachyury agonists may therefore improve the potency or efficiency of a T cell response against native Brachyury expressed by a tumor cell. The Brachyury antigen having the amino acid sequence of SEQ ID NO:18 is a non-limiting example of a Brachyury agonist (or a Brachyury antigen comprising an agonist epitope).

In addition, N-terminal expression sequences and the C-terminal tags, such as those described above with respect to the fusion proteins of SEQ ID NO:8, SEQ ID NO:10, or SEQ ID NO:20 are optional, but may be selected from several different sequences described elsewhere herein to improve or assist with expression, stability, and/or allow for identification and/or purification of the protein. Also, many different promoters suitable for use in yeast are known in the art. Furthermore, short intervening linker sequences (e.g., 1, 2, 3, 4, or 5 amino acid peptides) may be introduced between portions of a fusion protein comprising a Brachyury antigen for a variety of reasons, including the introduction of restriction enzyme sites to facilitate cloning, as cleavage sites for host phagosomal proteases, to accelerate protein or antigen processing, and for future manipulation of the constructs.

Optionally, proteins, including fusion proteins, which are used as a component of the yeast-Brachyury immunotherapeutic composition of the invention are produced using antigen constructs that are particularly useful for improving or stabilizing the expression of heterologous antigens in yeast. In one embodiment, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to yeast alpha factor leader sequence, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., 6× His or hexapeptide) or any other short epitope tag. Peptides attached to the C-terminus of an antigen according to the invention can be used with or without the addition of the N-terminal peptides discussed above, and vice versa.

In one embodiment, a synthetic peptide useful in a fusion protein to be expressed in a yeast is linked to the N-terminus of the antigen, the peptide consisting of at least two amino acid positions that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid positions at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (represented herein by SEQ ID NO:11). In addition to the enhanced stability of the expression product, this fusion partner does not appear to negatively impact the immune response against the immunizing antigen in the construct. In addition, the synthetic fusion peptides can be designed to provide an epitope that can be recognized by a selection agent, such as an antibody.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SECT; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be formulated with a pharmaceutically acceptable excipient and administered directly to a patient, stored for later administration, or loaded into a dendritic cell as an intact cell. The yeast cell can also be killed, or it can be derivatized such as by formation of yeast spheroplasts, cytoplasts, ghosts, or subcellular particles, any of which may be followed by storing, administering, or loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses the antigen. Yeast cells or yeast spheroplasts that recombinantly express the antigen(s) may be used to produce a yeast vehicle comprising a yeast cytoplast, a yeast ghost, or a yeast membrane particle or yeast cell wall particle, or fraction thereof.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) are expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome cl (CYC1), Sec7 protein (SECT) and acid phosphatase (PHOS), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego). For example, under one protocol, liquid cultures containing a suitable medium can be inoculated using cultures obtained from starter plates and/or starter cultures of yeast-Brachyury immunotherapy compositions, and are grown for approximately 20 h at 30° C., with agitation at 250 rpm. Primary cultures can then be expanded into larger cultures as desired. Protein expression from vectors with which the yeast were transformed (e.g., Brachyury expression) may be constitutive if the promoter utilized is a constitutive promoter, or may be induced by addition of the appropriate induction conditions for the promoter if the promoter utilized is an inducible promoter (e.g., copper sulfate in the case of the CUP1 promoter). In the case of an inducible promoter, induction of protein expression may be initiated after the culture has grown to a suitable cell density, which may be at about 0.2 Y.U./ml or higher densities.

One non-limiting example of a medium suitable for the culture of a yeast-Brachyury immunotherapy composition of the invention is U2 medium. U2 medium comprises the following components: 20 g/L of glucose, 6.7 g/L of Yeast nitrogen base containing ammonium sulfate, and 0.04 mg/mL each of histidine, leucine, tryptophan, and adenine. Another non-limiting example of a medium suitable for the culture of yeast-Brachyury immunotherapy composition of the invention is UL2 medium. UL2 medium comprises the following components: 20 g/L of glucose, 6.7 g/L of Yeast nitrogen base containing ammonium sulfate, and 0.04 mg/mL each of histidine, tryptophan, and adenine.

In one embodiment of the invention, when an inducible promoter is used (e.g. the CUP1 promoter) to express a Brachyury protein in a yeast vehicle according to the invention, induction of protein expression is initiated at a higher cell density as compared to the cell density that would be suitable for most proteins expressed by yeast using such a promoter. More specifically, the present inventors have discovered that optimal Brachyury antigen expression driven by the CUP1 promoter occurs when the yeast expressing the Brachyury antigen are allowed to grow to a cell density of between at least 0.5 Y.U/ml and approximately 2.0 Y.U./ml, and in one aspect, to between 0.5 Y.U./ml and approximately 1.5 Y.U./ml, and in one aspect, to between at least 1.0 Y.U./ml and about 2.0 Y.U./ml, and in another aspect, to at least about 1.0 Y.U./ml, prior to inducing expression of the Brachyury antigen in the yeast. The present inventors have discovered that subsequent to induction of Brachyury expression, the yeast will double only about 1× to 1.5×. Moreover, after induction of Brachyury expression, the inventors have discovered that growth of the yeast to cell densities higher than about 2.0 Y.U./ml, or for longer than about 6-8 hours, results in decreased viability of the cultures, while not substantially improving antigen accumulation in the yeast. Therefore, in one embodiment of the invention, a yeast-Brachyury immunotherapy composition having antigen expression under the control of an inducible promoter, such as the CUP1 promoter, is grown to mid-log phase prior to inducing antigen expression. In one aspect, the cells are grown to between about 1 and 2 Y.U./ml prior to induction of antigen expression. In one aspect, antigen expression is induced (e.g., by the addition of copper sulfate) and continues for up to 6, 6.5, 7, 7.5, or 8 hours. In one aspect, the induction occurs at a temperature of about 30° C. and agitation rate of 250 rpm.

In some embodiments of the invention, the yeast are grown under neutral pH conditions. As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5).

In one embodiment, control of the amount of yeast glycosylation is used to control the expression of antigens by the yeast, particularly on the surface. The amount of yeast glycosylation can affect the immunogenicity and antigenicity of the antigen, particularly one expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use yeast with abbreviated glycosylation patterns, e.g., *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens, viral vector vaccines) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-$\alpha$) or agonists or antagonists of type I interferon or a receptor thereof; type II interferon (including IFN-$\gamma$) or agonists or antagonists of type II interferon or a receptor thereof; anti-CD40, CD40L, lymphocyte-activation gene 3 (LAG3) protein and/or IMP321 (T-cell immunostimulatory factor derived from the soluble form of LAG3), anti-CTLA-4 antibody (e.g., to release anergic T cells); T cell co-stimulators (e.g., anti-CD 137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+ T regulatory cells); Flt3 ligand, imiquimod (Aldara™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, pro-inflammatory agents, and any agents that modulate the number of, modulate the activation state of, and/or modulate the survival of antigen-presenting cells or of TH17, TH1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic or enhance the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other agents or compositions or protocols that are useful for preventing or treating cancer or any compounds that treat or ameliorate any symptom of cancer, and particularly cancers associated with Brachyury expression or overexpression. In addition, compositions of the invention can be used together with other immunotherapeutic compositions, including prophylactic and/or therapeutic immunotherapy. Indeed, the compositions of the invention can be used to inhibit or reduce chemotherapy resistance or radiation resistance that may occur in metastatic cancer by inhibiting Brachyury expression in the cancer (and thereby inhibiting anti-proliferative influences) or compositions of the invention may enhance the performance of chemotherapy or radiation therapy in an individual. Additional agents, compositions or protocols (e.g., therapeutic protocols) that are useful for the treatment of cancer include, but are not limited to, chemotherapy, surgical resection of a tumor, radiation therapy, allogeneic or autologous stem cell transplantation, and/or targeted cancer therapies (e.g., small molecule drugs, biologics, or monoclonal antibody therapies that specifically target molecules involved in tumor growth and progression, including, but not limited to, selective estrogen receptor modulators (SERMs), aromatase inhibitors, tyrosine kinase inhibitors, serine/threonine kinase inhibitors, histone deacetylase (HDAC) inhibitors, retinoid receptor activators, apoptosis stimulators, angiogenesis inhibitors, poly (ADP-ribose_) polymerase (PARP) inhibitors, or immunostimulators). Any of these additional therapeutic agents and/or therapeutic protocols may be administered before, concurrently with, alternating with, or after the immunotherapy compositions of the invention, or at different time points. For example, when given to an individual in conjunction with chemotherapy or a targeted cancer therapy, it may be desirable to administer the yeast-Brachyury immunotherapy compositions during the "holiday" between doses of chemotherapy or targeted cancer therapy, in order to maximize the efficacy of the immunotherapy compositions. Surgical resection of a tumor may frequently precede administration of a yeast-Brachyury immunotherapy composition, but additional or primary surgery may occur during or after administration of a yeast-Brachyury immunotherapy composition.

The invention also includes a kit comprising any of the compositions described herein, or any of the individual components of the compositions described herein. Kits may include additional reagents and written instructions or directions for using any of the compositions of the invention to prevent or treat cancer associated with Brachyury expression or overexpression.

Methods for Administration or Use of Compositions of the Invention

Yeast-Brachyury immunotherapeutic compositions of the invention are designed for use to prevent or treat cancers that are associated with or characterized by Brachyury expression or overexpression, including by preventing emergence of such cancers, arresting progression of such cancers or eliminating such cancers. More particularly, yeast-Brachyury immunotherapeutic compositions can be used to prevent, inhibit or delay the development of Brachyury-expressing tumors, and/or to prevent, inhibit or delay tumor migration and/or tumor invasion of other tissues (metastases) and/or to generally prevent or inhibit progression of cancer in an individual. Yeast-Brachyury immunotherapeutic compositions can also be used to ameliorate at least one symptom of the cancer, such as by reducing tumor burden in the individual; inhibiting tumor growth in the individual; increasing survival of the individual; preventing, inhibiting, reversing or delaying development of tumor migration and/or tumor invasion of other tissues (metastatic cancer) and/or preventing, inhibiting, reversing or delaying progression of the cancer in the individual. Yeast-Brachyury immunotherapy can also be used therapeutically to inhibit, reduce or eliminate chemotherapy resistance or radiation resistance that may occur in metastatic cancer by inhibiting Brachyury expression in the cancer, and compositions of the invention may enhance the performance of chemotherapy or radiation therapy in an individual.

Cancers that are relevant to the compositions and methods of the invention are any cancer that expresses, or may express, Brachyury, or cancers in proximity to cancers that express or may express Brachyury, and include, but are not limited to, cancer of the breast, small intestine, stomach, kidney, bladder, uterus, ovary, testes, lung, colon, pancreas, or prostate, and include metastatic and late-stage cancers. In addition, Brachyury is expressed in tumors of B cell origin, such as chronic lymphocytic leukemia (CLL), Epstein-Barr virus transformed B cells, Burkitt's and Hodgkin's lymphomas, as well as metastatic cancers thereof.

One embodiment of the invention relates to a method to inhibit tumor migration and/or to reduce, halt (arrest), reverse or prevent the metastatic progression of cancer in an individual who has cancer, or to reverse the development of metastatic events in a cancer. As discussed above, Brachyury promotes the epithelial-mesenchymal transition (EMT) in human tumor cells, conferring on tumor cells a mesenchymal phenotype, as well as migratory and invasive abilities, while attenuating tumor cell cycle progression. Therefore, the involvement of Brachyury in metastatic processes makes it an ideal target for the prevention or inhibition of metastatic processes, including arresting cancer at a pre-metastatic stage. Use of a yeast-Brachyury immunotherapeutic composition of the invention can be effective to prevent or treat metastatic cancer, including arresting progression of the cancer, in the face of escape (or attempted escape) of the cancer from traditional therapy, such as chemotherapy and radiation. The method includes the steps of administering to the individual who has cancer an immunotherapeutic composition a yeast-Brachyury immunotherapeutic composition of the invention as described herein, including, but not limited to: (a) a yeast vehicle; and (b) a cancer antigen comprising at least one Brachyury antigen.

In one aspect, Brachyury is not detected in the individual's cancer at the time the composition is first administered. In general, when Brachyury is not detected in the individual's cancer, the individual may have an earlier stage cancer in which Brachyury expression has not yet manifested (e.g., stage I or stage II), or in which Brachyury expression is not yet detectable in any event (i.e., Brachyury may or may not be expressed at a low level or in a small number of tumor cells, but is not yet readily detectable using standard detection methods). In this aspect of the invention, the development of Brachyury-expressing tumor cells is prevented, delayed or inhibited by use of the yeast-Brachyury immunotherapeutic composition. As a result, tumor migration and/or other metastatic processes leading to metastatic progression of the tumor are prevented, delayed or inhibited and/or general arrest of tumor progression occurs in the individual.

In another aspect, Brachyury expression is or can be detected in the individual's cancer at the time the composition is first administered. The individual may have stage I, stage II, stage III, or stage IV cancer in this aspect of the invention. In this aspect, use of the yeast-Brachyury immunotherapeutic composition reduces, eliminates or slows or arrests the growth of tumors expressing Brachyury, which can result in reduction in tumor burden in the individual, inhibition of Brachyury-expressing tumor growth, and/or increased survival of the individual. The individual may experience an arrest, slowing or reversal in metastatic processes, improving survival and health of the patient, and furthermore, allowing other therapeutic protocols to treat the cancer.

Indeed, metastatic cancer can be associated with resistance, or increased resistance, to cancer therapies such as chemotherapy, radiation, or targeted cancer therapy, whereby the cancer "escapes" from the therapy or is simply less impacted by the therapy and progresses. Accordingly, there is a need to reduce or eliminate resistance to such therapies to improve or enhance the efficacy of the therapy and improve patient health and survival. Accordingly, one embodiment of the invention relates to a method to reduce or prevent chemotherapy-resistance, targeted cancer therapy-resistance, or radiation-resistance in a patient with cancer. The method comprises administering to an individual who has cancer and is receiving chemotherapy and/or radiation therapy for the cancer, a yeast-Brachyury immunotherapeutic composition as described herein, which may include a composition comprising: (a) a yeast vehicle; and (b) a cancer antigen comprising at least one Brachyury antigen. This method of the invention may also be used to treat resistance associated with other therapeutic treatments for cancer, including, but not limited to, targeted cancer therapy.

In one aspect of this embodiment, Brachyury is not detected in the individual's cancer at the time the composition is first administered. In this aspect, administration of a yeast-Brachyury immunotherapeutic composition prevents or inhibits the onset of resistance to chemotherapy or radiation therapy by inhibiting the development of Brachyury-expressing tumor cells in the cancer. In another aspect, Brachyury expression is detected in the individual's cancer at the time the composition is first administered. In this aspect, the individual may or may not already be experiencing resistance to chemotherapy or radiation. In either case, administration of the yeast-Brachyury immunotherapeutic composition of the invention prevents or inhibits the resistance to chemotherapy or radiation therapy or enhances the ability of the chemotherapy or radiation therapy to treat the individual, by reducing or eliminating Brachyury-expressing tumor cells in the patient.

Another embodiment of the invention relates to a method to treat cancer, and particularly, a Brachyury-expressing cancer. The method includes administering to an individual who has a Brachyury-expressing cancer a yeast-Brachyury immunotherapeutic composition described herein, which can include a composition comprising: (a) a yeast vehicle; and (b) a cancer antigen comprising at least one Brachyury antigen. In one aspect, the method reduces tumor burden in the patient. In one aspect, the method increases survival of the patient. In one aspect, the method inhibits tumor growth in the individual. In one aspect, the method prevents, arrests or reverses metastatic progression of the tumor.

Since Brachyury expression is believed to be more prevalent as a cancer advances or progresses into higher stages (e.g., from stage I to stage II to stage III to stage IV, depending on the particular cancer) and is associated with metastatic processes, it is an embodiment of the invention to provide a method to prevent or delay the onset of a Brachyury-expressing cancer, or to arrest the cancer at a pre-metastatic or pre-malignant stage. Such a method includes administering to an individual in whom Brachyury-expressing cancer cells are not detected a yeast-Brachyury immunotherapeutic composition described herein, which can include a composition comprising: (a) a yeast vehicle; and (b) a cancer antigen comprising at least one Brachyury antigen. In one aspect of this embodiment, the cancer is known to express or believed to be susceptible to expressing Brachyury at some stage of the cancer in at least a subset of individuals with the cancer. In one aspect of this embodiment, the individual already has a cancer, but Brachyury is not detected in the cancer at the time the composition is first administered, meaning that the individual may have an earlier stage cancer in which Brachyury expression has not yet manifested, or in which Brachyury expression is not yet detectable in any event (i.e., Brachyury may or may not be expressed at a low level or in a small number of tumor cells, but is not yet readily detectable using standard detection methods). In some cases, the type of cancer may be known to have a high rate of metastatic progression, In this aspect, administration of the yeast-Brachyury immunotherapeutic composition prevents, delays or inhibits the development of Brachyury-expressing tumor cells in the patient's cancer, and therefore prevents, arrests, delays or inhibits metastatic processes that accompany Brachyury expression. In another aspect, the individual does not have cancer when the composition is administered. Such an individual may be "predisposed" or likely to develop cancer, perhaps because of family history or a genetic marker, or because the individual has shown signs of precancerous cells or lesions or has precancerous (premalignant) cells or lesions.

In one aspect, the individual is additionally treated with at least one other therapeutic compound or therapeutic protocol useful for the treatment of cancer. Such therapeutic agents and protocols have been discussed in detail elsewhere herein. For example, in any of the embodiments regarding methods of the invention described herein, in one aspect, when the individual has cancer (regardless of the status of detectable Brachyury expression in tumor cells) the individual is being treated or has been treated with another therapy for cancer. Such therapy can include any of the therapeutic protocols or use of any therapeutic compound or agent described previously herein, including, but not limited to, chemotherapy, radiation therapy, targeted cancer therapy, surgical resection of a tumor, stem cell transfer, cytokine therapy, adoptive T cell transfer, and/or administration of a second immunotherapeutic composition. In the case of administration of a second immunotherapeutic composition, such compositions may include, but are not limited to, additional yeast-based immunotherapy, recombinant virus-based immunotherapy (viral vectors), cytokine therapy, immunostimulant therapy (including chemotherapy with immunostimulating properties), DNA vaccines, and other immunotherapy compositions.

In one aspect, the second immunotherapeutic composition includes a second cancer antigen that does not include Brachyury antigen. For example, a second immunotherapeutic composition useful in combination with a yeast-Brachyury immunotherapeutic composition is a yeast-immunotherapeutic composition comprising another cancer antigen. Such cancer antigens may include, but are not limited to, carcinoembryonic antigen (CEA), point mutated Ras oncoprotein, MUC-1, EGFR, BCR-Abl, MART-1, MAGE-1, MAGE-3, GAGE, GP-100, MUC-2, normal and point mutated p53 oncoproteins, PSMA, tyrosinase, TRP-1 (gp75), NY-ESO-1, TRP-2, TAG72, KSA, CA-125, PSA, HER-2/neu/c-erb/B2, hTERT, p73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, NGEP, modifications of such antigens, splice variants of such antigens, and epitope agonists of such antigens, as well as combinations of such antigens, and/or immunogenic domains thereof, modifications thereof, variants thereof, and/or epitope agonists thereof.

As used herein, to "treat" a cancer, or any permutation thereof (e.g., "treated for cancer", etc.) generally refers to administering a composition of the invention once the cancer has occurred (e.g., once the cancer has been diagnosed or detected in an individual), with at least one therapeutic goal of the treatment (as compared to in the absence of this treatment) including: reduction in tumor burden, inhibition of tumor growth, increase in survival of the individual, delaying, inhibiting, arresting or preventing the onset or development of metastatic cancer (such as by delaying, inhibiting, arresting or preventing the onset of development of tumor migration and/or tumor invasion of tissues outside of primary cancer and/or other processes associated with metastatic progression of cancer), delaying or arresting cancer progression, improvement of immune responses against the tumor, improvement of long term memory immune responses against the tumor antigens, and/or improved general health of the individual. To "prevent" or "protect" from a cancer, or any permutation thereof (e.g., "prevention of cancer", etc.), generally refers to administering a composition of the invention before a cancer has occurred, or before a specific stage of cancer or tumor antigen expression in a cancer has occurred (e.g., before Brachyury expression is detected in the cancer), with at least one goal of the treatment (as compared to in the absence of this treatment) including: preventing or delaying the onset or development of a cancer, or, should the cancer occur after the treatment, at least reducing the severity of the cancer (e.g., reducing the level of tumor growth, arresting cancer progression, improving the immune response against the cancer, inhibiting metastatic processes) or improving outcomes in the individual (e.g., improving survival).

The present invention includes the delivery (administration, immunization) of a yeast-Brachyury immunotherapeutic composition of the invention to a subject or individual. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of a tumor). Suitable routes of administration will be apparent to those of skill in the art, depending on the type of cancer to be prevented or treated and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). In one aspect, a yeast-Brachyury immunotherapeutic composition of the invention is administered subcutaneously. In one aspect, the yeast-Brachyury immunotherapeutic composition is administered directly into a tumor milieu.

In general, a suitable single dose of a yeast-Brachyury immunotherapeutic composition is a dose that is capable of effectively providing a yeast vehicle and the Brachyury antigen to a given cell type, tissue, or region of the patient body in an amount effective to elicit an antigen-specific immune response against one or more Brachyury antigens or epitopes, when administered one or more times over a suitable time period. For example, in one embodiment, a single dose of a yeast-Brachyury of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Yeast Units (Y.U., which is $1 \times 10^6$ yeast cells or yeast cell equivalents) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one embodiment, a suitable dose includes doses between 1 Y.U. and 40 Y.U. and in one aspect, between 10 Y.U. and 40 Y.U. In one embodiment, the doses are administered at different sites on the individual but during the same dosing period. For example, a 40 Y.U. dose may be administered by injecting 10 Y.U. doses to four different sites on the individual during one dosing period. The invention includes administration of an amount of the yeast-Brachyury immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose. One Yeast Unit (Y.U.) is $1 \times 10^7$ yeast cells or yeast cell equivalents.

"Boosters" or "boosts" of a therapeutic composition are administered, for example, when the immune response against the antigen has waned or as needed to provide an immune response or induce a memory response against a particular antigen or antigen(s). Boosters can be administered about 1, 2, 3, 4, 5, 6, 7, or 8 weeks apart, or monthly, bimonthly, quarterly, annually, and/or in a few or several year increments after the original administration, depending on the status of the individual being treated and the goal of the therapy at the time of administration (e.g., prophylactic, active treatment, maintenance). In one embodiment, an administration schedule is one in which doses of yeast-Brachyury immunotherapeutic composition is administered at least 1, 2, 3, 4, 5, 6, 7, 8, 9, 10, or more times over a time period of from weeks, to months, to years. In one embodiment, the doses are administered weekly or biweekly for 1, 2, 3, 4, 5, 6, 7, 8, 9, 10 or more doses, followed by biweekly or monthly doses as needed to achieve the desired preventative or therapeutic treatment for cancer. Additional boosters can then be given at similar or longer intervals (months or years) as a maintenance or remission therapy, if desired.

In one aspect of the invention, one or more additional therapeutic agents or therapeutic protocols are administered or performed sequentially and/or concurrently with the administration of the yeast-Brachyury immunotherapy composition (e.g., surgical resection of the tumor, administration of chemotherapy, administration of radiation therapy, administration of another immunotherapy composition or protocol, cytokine therapy, adoptive T cell transfer, or stem cell transplantation). For example, one or more therapies can be administered or performed prior to the first dose of yeast-Brachyury immunotherapy composition or after the first dose is administered. In one embodiment, one or more therapies can be administered or performed in an alternating manner with the dosing of yeast-Brachyury immunotherapy composition, such as in a protocol in which the yeast-Brachyury composition is administered at prescribed intervals in between one or more consecutive doses of chemotherapy or other therapy. In one embodiment, the yeast-Brachyury immunotherapy composition is administered in one or more doses over a period of time prior to commencing additional therapies. In other words, the yeast-Brachyury immunotherapeutic composition is administered as a monotherapy for a period of time, and then an additional therapy is added (e.g., chemotherapy), either concurrently with new doses of yeast-Brachyury immunotherapy, or in an alternating fashion with yeast-Brachyury immunotherapy. Alternatively or in addition, another therapy may be administered for a period of time prior to beginning administration of the yeast-Brachyury immunotherapy composition, and the concepts may be combined (e.g., surgical resection of a tumor, followed by monotherapy with yeast-Brachyury immunotherapy for several weeks, followed by alternating doses of chemotherapy and yeast-Brachyury immunotherapy for weeks or months, optionally followed by monotherapy using yeast-Brachyury immunotherapy or another therapy, or by a new protocol of combinations of therapy provided sequentially, concurrently, or in alternating fashion). Various protocols for the treatment of cancer using yeast-Brachyury immunotherapy are contemplated by the invention, and these examples should be considered to be non-limiting examples of various possible protocols.

In one aspect of the invention, additional antigens other than Brachyury are also targeted using yeast-based immunotherapy, in addition to targeting Brachyury. Such additional target antigens can be included within the same yeast-vehicle as the Brachyury antigens, or additional yeast-based immunotherapy compositions targeting different antigens can be produced and then combined as desired depending on the individual to be treated, the antigens expressed by the type of cancer or by the individual's particular tumor, and/or depending on the stage of cancer in the individual, or the stage of treatment of the individual. For examples a combination of antigens may be selected that cover: (1) antigens involved in seminal events in cancer development, such as mutated Ras, antigens involved in or associated with dysregulation of cellular processes, such as CEA, and (3) Brachyury, which is involved in metastatic processes. For example, on or more other yeast-based immunotherapy compositions may express one or more antigens including, but not limited to, carcinoembryonic antigen (CEA), point mutated Ras oncoprotein, MUC-1, EGFR, BCR-Abl1, MART-1, MAGE-1, MAGE-3, GAGE, GP-100, MUC-2, normal and point mutated p53 oncoproteins, PSMA, tyrosinase, TRP-1 (gp75), NY-ESO-1, TRP-2, TAG72, KSA, CA-125, PSA, HER-2/neu/c-erb/B2, hTERT, p73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, NGEP, modifications of such antigens, splice variants of such antigens, and epitope agonists of such antigens, as well as combinations of such antigens, and/or immunogenic domains thereof, modifications thereof, variants thereof, and/or epitope agonists thereof. One, two, three, or more of these yeast-based immunotherapy compositions may be administered to an individual prior to, concurrently or alternating with, and/or after administration of a yeast-Brachyury immunotherapy composition, in order to optimize targeting of antigens in the individual's tumor. As above, additional therapies can also be used in such protocols (e.g., surgical resection of tumor, chemotherapy, targeted cancer therapy, radiation therapy, etc.).

In one embodiment of the invention, a method to treat cancer is provided. The method includes the steps of: (a) administering to an individual who has cancer in which Brachyury expression has not been detected, a first immunotherapeutic composition comprising a yeast vehicle and a first cancer antigen that does not comprise a Brachyury antigen; and (b) administering to the individual, prior to, concurrently with, or subsequent to, administration of the first immunotherapeutic composition a second immunotherapeutic composition comprising a yeast vehicle and a second cancer antigen comprising a Brachyury antigen. In additional embodiments, the method can include administering one or more additional immunotherapeutic compositions, wherein the each of the one or more additional immunotherapeutic compositions comprises an additional cancer antigen. The additional antigen can be any of those known in the art or described herein, including, but not limited to, mutated Ras, carcinoembryonic antigen (CEA), and MUC-1.

In another embodiment of the invention, a method to treat cancer includes the following steps: (a) administering to an individual who has cancer a first immunotherapeutic composition comprising a yeast vehicle and a mutated Ras antigen; (b) administering to the individual of (a) a second immunotherapeutic composition comprising a yeast vehicle and an antigen selected from the group consisting of carcinoembryonic antigen (CEA) and mucin-1 (MUC-1); and (c) administering to the individual of (a) and (b) a third immunotherapeutic composition comprising a yeast vehicle and a Brachyury antigen. One or more of the steps of administration in (a), (b) and (c) can be performed concurrently, or sequentially. Steps may be repeated as needed to treat a particular individual's cancer, and the cancer antigens can be modified before or during treatment to specifically address the particular individual's cancer.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect utilizing the invention include humans, non-human primates, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin, W. Orenstein, and P. Offit, eds., Fifth Edition (2008).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN®s have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic, physiological, chemical, or other processes of a cell, a tissue, or an organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

General reference to a protein or polypeptide used in the present invention includes full-length proteins, near full-length proteins (defined above), or any fragment, domain (structural, functional, or immunogenic), conformational epitope, or a homologue or variant of a given protein. A fusion protein may also be generally referred to as a protein or polypeptide. An isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" or "variant" is used to refer to a protein or peptide which differs from a reference protein or peptide (i.e., the "prototype" or "wild-type" protein) by minor modifications to the reference protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue or variant can have enhanced, decreased, or substantially similar properties as compared to the reference protein or peptide. A homologue or variant can include an agonist of a protein or an antagonist of a protein. Homologues or variants can be produced using techniques known in the art for the production of proteins including, but not limited to, direct modifications to the isolated reference protein, direct protein synthesis, or modifications to the nucleic acid sequence encoding the protein using, for example, classic or recombinant DNA techniques to effect random or targeted mutagenesis, resulting in the encoding of a protein variant. In addition, naturally occurring variants of a reference protein may exist (e.g., isoforms, allelic variants, or other natural variants that may occur from individual to individual) and may be isolated, produced and/or utilized in the invention.

A homologue or variant of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 86% identical, or at least about 87% identical, or at least about 88% identical, or at least about 89% identical, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein (e.g., an amino acid sequence specified herein, or the amino acid sequence of a specified protein). In one embodiment, the homologue or variant comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the amino acid sequence of the reference protein.

As used herein, unless otherwise specified, reference to a percent (%) identity refers to an evaluation of homology which is performed using: (1) a Basic Local Alignment Search Tool (BLAST) basic homology search using blastp for amino acid searches and blastn for nucleic acid searches with standard default parameters, wherein the query sequence is filtered for low complexity regions by default (such as described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." *Nucleic Acids Res.* 25:3389-3402, incorporated herein by reference in its entirety); (2) a BLAST alignment of two sequences (e.g., using the parameters described below); (3) and/or PSI-BLAST with the standard default parameters (Position-Specific Iterated BLAST. It is noted that due to some differences in the standard parameters between Basic BLAST and BLAST for two sequences, two specific sequences might be recognized as having significant homology using the BLAST program, whereas a search performed in Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST as described in Tatusova and Madden, (1999), "Blast 2 sequences—a new tool for comparing protein and nucleotide sequences", FEMS Microbiol Lett. 174:247-250, incorporated herein by reference in its entirety. Such a sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST sequence alignment for two sequences is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome or a segment of the genome containing more than one gene, in which the nucleic acid molecule is found in nature. An isolated nucleic acid molecule can include a complete gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule may also include portions of a gene. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a plasmid useful for transfecting yeast. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell, such as a yeast.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of a yeast-Brachyury immunotherapeutic composition.

In this experiment, yeast (*Saccharomyces cerevisiae*) were engineered to express human Brachyury under the control of the copper-inducible promoter, CUP1, or the constitutive promoter, TEF2, producing yeast-Brachyury immunotherapy compositions. In each case, a fusion protein comprising a Brachyury antigen was produced as a single polypeptide with the following sequence elements fused in frame from N- to C-terminus, represented by SEQ ID NO:8 (1) an N-terminal peptide to impart resistance to proteasomal degradation and stabilize expression (positions 1 to 6 of SEQ ID NO:8, the peptide sequence also represented herein by SEQ ID NO:11); 2) amino acids 2-435 of SEQ ID NO:6, SEQ ID NO:6 representing a near full-length human Brachyury protein (positions 7-440 of SEQ ID NO:8); and (3) a hexahistidine tag (positions 441-446 of SEQ ID NO:8). The amino acid sequences used in this fusion protein can be modified by the use of additional or alternate amino acids flanking either end of the Brachyury antigen, if desired, and shorter portions of the Brachyury antigen may also be used. A nucleic acid sequence encoding the fusion protein of SEQ ID NO:8 (codon optimized for yeast expression) is represented herein by SEQ ID NO:7.

Briefly, DNA encoding a full length human Brachyury protein from a Brachyury-PCRII plasmid provided by the National Cancer Institute (Dr. Jeffrey Schlom) was amplified using PCR, and then inserted at EcoRI and SpeI cloning sites behind the CUP1 promoter (vector pGI-100) or the TEF2 promoter (vectors plu011 or pGI-172) in yeast 2 μm expression vectors. Nucleotide sequences encoding the N-terminal stabilization peptide, MADEAP (SEQ ID NO:11) and a C-terminal hexahistidine peptide were also added to the plasmid vector to encode the complete fusion protein represented by SEQ ID NO:8. The resulting plasmids were transformed into DH5α for plasmid storage, and into *Saccharomyces cerevisiae* W303α for production of the yeast-Brachyury immunotherapeutic compositions.

Transformation into *Saccharomyces cerevisiae* was performed by lithium acetate/polyethylene glycol transfection, and primary transfectants were selected on solid minimal plates lacking Uracil (UDM; uridine dropout medium). Colonies were selected by growing in U2 (uridine dropout medium) or UL2 (uridine and leucine dropout medium) medium at 30° C.

The yeast-Brachyury immunotherapy composition comprising a polynucleotide encoding the human Brachyury fusion protein represented by SEQ ID NO:8 under the control of the CUP1 promoter is also referred to herein as GI-6301. The yeast-Brachyury immunotherapy composition comprising a polynucleotide encoding the human Brachyury fusion protein represented by SEQ ID NO:8 under the control of the TEF2 promoter (in vector plu011) is also referred to herein as GI-6302. The yeast Brachyury immunotherapy composition comprising a polynucleotide encoding the human Brachyury fusion protein represented by SEQ ID NO:8 under the control of the TEF2 promoter (in vector pGI-172) is also referred to herein as GI-6303.

Liquid cultures lacking uridine (U2) or lacking uridine and leucine (UL2) were inoculated using the plates and starter cultures described above, and were grown for 20 h at 30° C., 250 rpm. pH buffered media containing 4.2 g/L of Bis-Tris (BT-U2; BT-UL2) were also inoculated to evaluate yeast-Brachyury immunotherapeutics produced under neutral pH manufacturing conditions (data not shown). Primary cultures were used to inoculate final cultures of the same formulation.

Recipe for U2 Liquid Media:
  15 g/L of glucose
  6.7 g/L of Yeast nitrogen base containing ammonium sulfate
  0.04 g/L each of histidine, tryptophan, adenine and 0.06 g/L of leucine Recipe for UL2 Liquid Media:
  15 g/L of glucose
  6.7 g/L of Yeast nitrogen base containing ammonium sulfate
  0.04 g/L each of histidine, tryptophan, and adenine In initial experiments comparing yeast-Brachyury immunotherapeutic compositions under the control of different promoters, CUP1-driven (inducible expression) yeast-Brachyury expression was initiated by the addition of 0.5 mM copper sulfate after the yeast-Brachyury culture reached a density of approximately 0.2 Y.U./ml, and was continued until the culture reached a density of 0.5-1.5 Y.U. (yeast-Brachyury doubled only about 1-1.5 after the addition of copper sulfate, but a large amount of Brachyury protein was produced by the cells). TEF2-driven yeast-Brachyury expression is constitutive, and growth of these cells was continued until the cultures reached a density of between 1.1 to 4.0 Y.U./ml. The cells from each culture were then harvested, washed and heat-killed at 56° C. for 1 hour in PBS. Live cells from each culture were also processed for comparison.

After heat-kill of the cultures, the cells were washed three times in PBS. Total protein expression was measured by a TCA precipitation/nitrocellulose binding assay and by Western blot using an anti-his tag monoclonal antibody and an anti-Brachyury antibody (Abcam, Cambridge, Mass.). Protein content was quantified using semi-quantitative digital imaging methods.

The results of the initial expression experiments (data not shown) demonstrated that each of the yeast-Brachyury immunotherapy compositions of the invention expressed the Brachyury fusion protein, i.e., using either the CUP1 promoter or the TEF2 promoter, and expression was detected using either media (U2 and UL2). In addition, antigen expression was detectable in both heat-killed and live yeast cells (data not shown). Brachyury expression was significantly higher in the yeast-Brachyury immunotherapeutic composition comprising the CUP1 promoter (GI-6301) and so this composition was selected for further studies, including expression optimization and for in vitro and in vivo experiments (see Examples below).

Figure 1A:
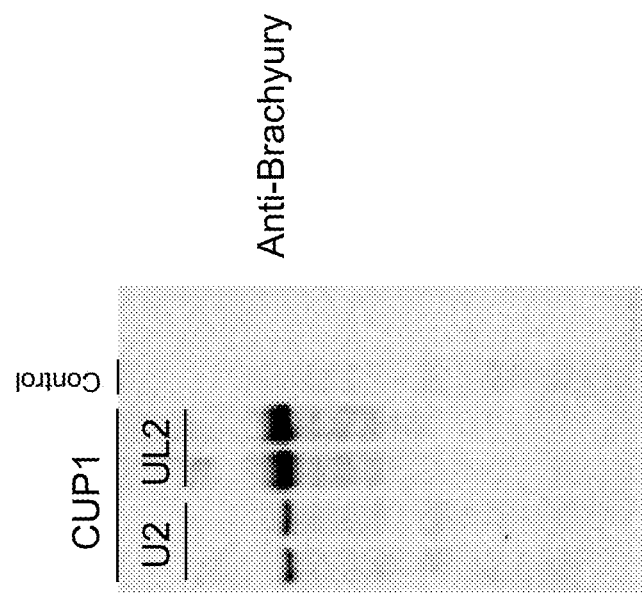
FIG. 1A is a digitized image of a Western blot showing detection by anti-Brachyury of expression of Brachyury in a yeast-Brachyury immunotherapeutic composition, with both U2 and UL2 media.

FIG. 1A shows expression of Brachyury in GI-6301 using both U2 and UL2 media using the anti-Brachyury antibody for detection. Control yeast expressing a non-Brachyury antigen did not stain with the antibody. FIG. 1B shows expression of Brachyury in the same GI-6301 preparations, using anti-His to identify the hexahistidine tag on the Brachyury fusion protein. Control yeast expressing a non-Brachyury antigen but having a hexahistidine tag is also shown. These results showed good Brachyury expression using either media, although expression in UL2 media was significantly higher.

Example 2

The following example describes the identification of conditions for antigen expression and manufacturing of the yeast-Brachyury immunotherapeutic composition, GI-6301.

To determine the optimum density for copper induction of GI-6301 antigen expression, starter and intermediate cultures of GI-6301 were prepared using the standard growth conditions in UL2 media described in Example 1 above. Aliquots of the culture were then diluted to 0.5 Y.U./ml, 1.0 Y.U./ml and 1.5 Y.U./ml and incubated at 30° C. for 1 hour. 0.5 mM CuSO$_4$ was added to the cultures to induce Brachyury expression, and culturing was continued. Cells were collected and counted at 6 hours and 14 hours for measurement of cell density. 20 Y.U. of heat-killed yeast from each condition was lysed, total protein was measured, and Western blots were generated using anti-His.

TABLE 1

|  | Induction Time | | |
| --- | --- | --- | --- |
|  | 0 hours | 6 hours | 14 hours |
| Cell Density | 0.5 | 1.03 | 0.96 |
| (Y.U./ml) | 1.0 | 1.88 | 1.74 |
|  | 1.5 | 3.14 | 2.7 |

Figure 2:
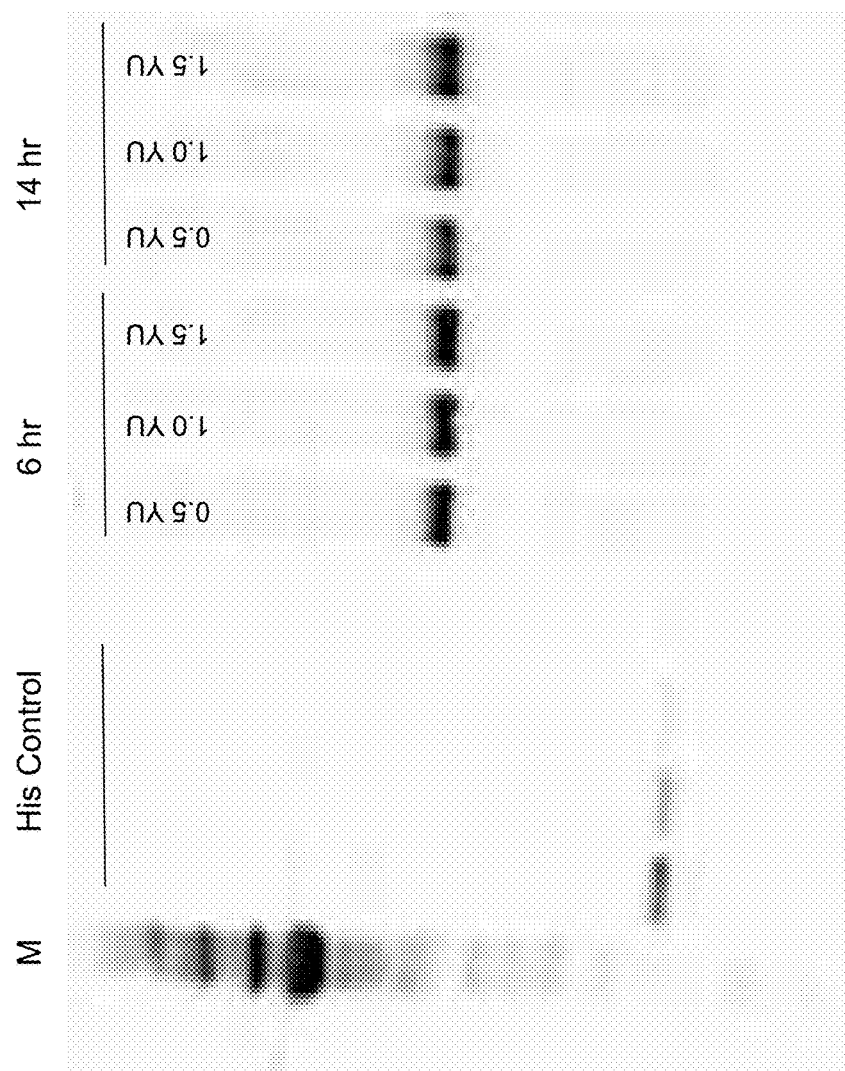
FIG. 2 is a digitized image of a Western blot showing expression of Brachyury in a yeast-Brachyury immunotherapeutic composition where the cell density at antigen induction and the time to harvest after antigen induction were varied.

As shown in Table 1, yeast only doubled about 1 time after copper induction (other experiments showed up to 1.5× doubling), and cell density and viability (not shown) decreased after 6 hours of copper induction. FIG. 2 shows that all three induction densities resulted in significant expression of Brachyury, with a trend toward higher Brachyury expression at the higher induction densities. However, additional experiments using induction starting densities of 2.1 Y.U./ml and 2.8 Y.U./ml and 375 µM CuSO$_4$ showed that protein expression began to decrease as the density of the cultures at the start of copper induction increased, and did not significantly improve after about 6-8 hours (data not shown).

Next, the effect of the amount of CuSO$_4$ on Brachyury expression was investigated. GI-6301 was grown from starter and intermediate cultures in UL2 media as described in Example 1. Aliquots of the culture were then diluted to 1.0 Y.U./ml and incubated at 30° C. for 1 hour. CuSO$_4$ was added to each culture at a concentration of either 375 µM or 500 µM, and induction of protein expression was allowed to proceed to various time points (2 hrs, 4 hrs, 6 hrs, 8 hrs, 24 hrs), at which point the cells were harvested, heat-killed, and processed for evaluation of protein expression using anti-His Western blots as described above. While both concentrations of CuSO$_4$ resulted in good expression of Brachyury, protein expression using 375 µM appeared to be slightly better, particularly at later time points (data not shown).

Accordingly, for CUP1-driven yeast-Brachyury (inducible expression), the inventors discovered that induction of antigen expression at mid-log phase growth of the yeast was optimal for antigen production. For production of the yeast-Brachyury immunotherapeutic composition (GI-6301) used in the following Examples, cells were grown in UL2 media as described in Example 1 to between 1 and 2 Y.U./ml, and were then induced by the addition of 0.375-0.5 mM copper sulfate for up to 6-8 hours at 30° C., 250 rpm. Cells were harvested, washed and heat killed at 56° C. for 1 h in PBS.

Example 3

The following example describes the construction and production of an additional yeast-Brachyury immunotherapeutic composition, where the Brachyury antigen contains a T cell agonist epitope.

In this experiment, yeast (Saccharomyces cerevisiae) were engineered to express a human Brachyury antigen that is a near-full-length Brachyury protein comprising the T cell epitope WLLPGTSTV (SEQ ID NO:13), which is an agonist epitope. The native Brachyury T cell epitope, present in SEQ ID NO:6 or 8, for example, is WLLPGTSTL (SEQ ID NO:12). The human Brachyury agonist antigen was expressed under the control of the copper-inducible promoter, CUP1, producing a yeast-Brachyury immunotherapy composition. More particularly, a fusion protein comprising a Brachyury agonist antigen (i.e., a Brachyury antigen containing at least one agonist epitope) was produced as a single polypeptide with the following sequence elements fused in frame from N- to C-terminus, represented by SEQ ID NO:20 (1) an N-terminal peptide to impart resistance to proteasomal degradation and stabilize expression (positions 1 to 6 of SEQ ID NO:20, the peptide sequence also represented herein by SEQ ID NO:11); 2) amino acids 2-435 of SEQ ID NO:18 (represented by positions 7-440 of SEQ ID NO:20; SEQ ID NO:18 represents a full-length human Brachyury agonist protein having a single amino acid substitution at position 254 as compared to wild-type Brachyury protein); and (3) a hexahistidine tag (positions 441-446 of SEQ ID NO:20). The agonist epitope (SEQ ID NO:13) is located at positions 251 to 259 of SEQ ID NO:20 (positions 246 to 254 of SEQ ID NO:18). The amino acid sequences used in this fusion protein can be modified by the use of additional or alternate amino acids flanking either end of the Brachyury antigen, if desired, and shorter portions of the Brachyury antigen may also be used. A nucleic acid sequence encoding the fusion protein of SEQ ID NO:20 (codon optimized for yeast expression) is represented herein by SEQ ID NO:19.

Briefly, DNA encoding the near full-length human Brachyury protein as described in Example 1 (i.e., full-length Brachyury minus the N-terminal methionine), modified by site directed mutagenesis to introduce a substitution of a valine for the leucine at position 254 with respect to the full-length Brachyury protein, was amplified using PCR, and then inserted at EcoRI and SpeI cloning sites behind the CUP1 promoter (vector pGI-100) in yeast 2 µm expression vectors. Nucleotide sequences encoding the N-terminal stabilization peptide, MADEAP (SEQ ID NO:11) and a C-terminal hexahistidine peptide were also added to the plasmid vector to encode the complete fusion protein represented by SEQ ID NO:20. The resulting plasmids were transformed into DH5a for plasmid storage, and into Saccharomyces cerevisiae W303α for production of the yeast-Brachyury immunotherapeutic composition.

Transformation into Saccharomyces cerevisiae was performed by lithium acetate/polyethylene glycol transfection, and primary transfectants were selected on solid minimal plates lacking Uracil (UDM; uridine dropout medium). Colonies were selected by growing in UL2 (uridine and leucine dropout medium) medium at 30° C.

The yeast-Brachyury immunotherapy composition comprising a polynucleotide encoding the human Brachyury agonist fusion protein represented by SEQ ID NO:20 under the control of the CUP1 promoter is also referred to herein as GI-6305.

GI-6305 cells were grown in UL2 media as described in Example 1 to between 1 and 2 Y.U./ml, and were then induced by the addition of 0.375-0.5 mM copper sulfate for up to 6-8 hours at 30° C., 250 rpm, using the conditions developed by the inventors for GI-6301 as described in Example 2. Cells were harvested, washed and heat killed at 56° C. for 1 h in PBS.

After heat-kill of the cultures, the cells were washed three times in PBS. Total protein expression was measured by a TCA precipitation/nitrocellulose binding assay and by Western blot using an anti-his tag monoclonal antibody and an anti-Brachyury antibody (Abcam, Cambridge, Mass.). Protein content was quantified using semi-quantitative digital imaging methods.

Figure 1C:
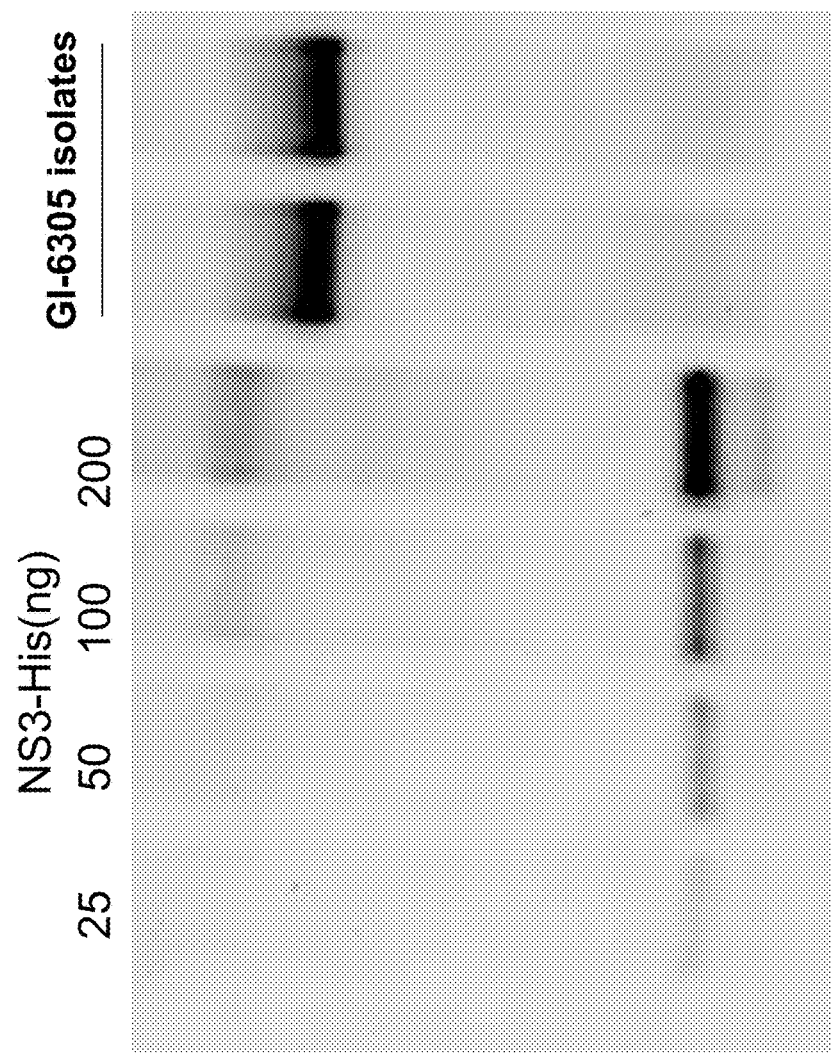
FIG. 1C is a digitized image of a Western blot showing the robust expression of Brachyury agonist antigen in GI-6305 using anti-His to identify the hexahistidine tag on the Brachyury fusion protein.

FIG. 1C shows the robust expression of Brachyury agonist antigen in GI-6305 using anti-His to identify the hexahistidine tag on the Brachyury fusion protein. The approximate antigen content for GI-6305 grown in UL2 medium in this experiment was >22615 ng/Y.U.

Example 4

The following example demonstrates the expansion of Brachyury-specific T cells using a yeast-Brachyury immunotherapeutic composition of the invention.

To determine whether T cells from normal donors were capable of generating T cells that are specific for Brachyury antigen, dendritic cells (DCs) were prepared from the peripheral blood mononuclear cells (PBMCs) of two normal donors. Briefly, isolated PBMCs were cultured for 5-days in the presence of GM-CSF and IL-4, and were subsequently incubated with Control Yeast (also denoted "YVEC", which is a *Saccharomyces cerevisiae* yeast that is transformed with an empty vector, or vector that does not contain an antigen-encoding insert) or Brachyury Yeast (GI-6301, described in Examples 1 and 2 above), at a ratio of yeast:DCs=1:1. After 48-hours co-culture, the DCs were used as APCs for stimulation of autologous T cells. Each cycle of stimulation, designated as IVS (in vitro stimulation), consisted of 3 days culture in absence of IL-2, following by 4 additional days in the presence of recombinant IL-2 (20 U/ml). At the end of IVS 2, T cells were stained with a control tetramer or a tetramer specific for the Brachyury peptide Tp2 (WLLPGTSTL, positions 246 to 254 of SEQ ID NO:2 or SEQ ID NO:6). Table 2 shows the percentage of CD8+ T cells that stained positive with each tetramer.

TABLE 2

| Donor | Stimulation | Control Tetramer | Brachyury Tetramer |
|---|---|---|---|
| 07706 | Control Yeast | 0.21 | 0.30 |
|  | Brachyury Yeast | 0.28 | 0.67 |
| 17663 | Control Yeast | 0.04 | 0.29 |
|  | Brachyury Yeast | 0.05 | 0.54 |

In a second experiment, dendritic cells (DCs) were prepared from PBMCs of nine normal donors using a 5-day culture in presence of GM-CSF and IL-4, subsequently incubated with Brachyury yeast (GI-6301), at a ratio yeast:DCs=1:1, as described above. After 48-hours in co-culture, the DCs were used as APCs for stimulation of autologous T cells. Each cycle of IVS was performed as described above. At the end of IVS 2, T cells were stained with a control tetramer or a tetramer specific for the Brachyury peptide Tp2. Table 3 shows the percentage of CD8+ T cells that stained positive with each Tetramer.

TABLE 3

| Donor | Stimulation | Control Tetramer | Brachyury Tetramer |
|---|---|---|---|
| 07706 | Brachyury Yeast | 0.28 | 0.67 |
| 17663 | Brachyury Yeast | 0.05 | 0.54 |
| 32249 | Brachyury Yeast | 0.01 | 1.24 |
| 29004 | Brachyury Yeast | 0.02 | 0.36 |
| 19063 | Brachyury Yeast | 0.10 | 2.57 |
| 06852 | Brachyury Yeast | 0.05 | 0.33 |
| 26532 | Brachyury Yeast | 0.07 | 0.11 |
| 12172 | Brachyury Yeast | 0.01 | 0.11 |
| 26725 | Brachyury Yeast | 0.01 | 0.20 |

The results in Tables 2 and 3 show that stimulation of normal donor T cells with a yeast-Brachyury immunotherapeutic of the invention increases the percentage of tetramer-positive CD8+ T cells in a majority of the normal donors, as compared to controls, indicating that normal human T cells have the capacity to recognize Brachyury as an immunogen.

Example 5

The following example demonstrates the ability of a yeast-Brachyury immunotherapeutic composition to generate Brachyury-specific CTLs from normal donor PBMCs that lyse Brachyury-expressing targets.

In this experiment, Brachyury-specific T cells from three of the normal donors from Table 2 above were expanded in vitro using DCs incubated with Brachyury yeast (GI-6301) for 2 cycles of IVS (as described in Example 4). A third IVS was carried out with DCs matured in presence of CD40L and pulsed with the Brachyury-specific Tp2 peptide (WLLPGTSTL, positions 246 to 254 of SEQ ID NO:2 or SEQ ID NO:6). At day 5, CD8− T cells were isolated and used in an overnight cytotoxic T lymphocyte (CTL) assay against SW480 (HLA-A2+/Brachyury high) and MCF7 (HLA-A2+/Brachyury low) tumor cell targets, at the indicated effector:target (ET) ratios (see FIG. 3). Shown in Table 4 is the percentage of CD8+ T cells that stained positive with a control tetramer versus a Brachyury-specific Tp2 tetramer.

TABLE 4

| Normal Donor | Stimulation | Control Tetramer | Brachyury Tetramer |
|---|---|---|---|
| 07706 | Brachyury Yeast/Tp2 | 0.33 | 1.84 |
| 17663 | Brachyury Yeast/Tp2 | 0.11 | 0.65 |
| 26532 | Brachyury Yeast/Tp2 | 0.05 | 0.11 |

FIGS. 3A (donor 07706), 3B (donor 17663) and 3C (donor 26532) show that PBMCs from two out of three normal donors were capable of generating CD8+ CTLs that could kill targets expressing Brachyury. Taken together, these data demonstrate that yeast-Brachyury immunotherapeutic compositions can generate Brachyury-specific CTLs that are capable of killing a Brachyury-expressing tumor cell.

Figure 4B:
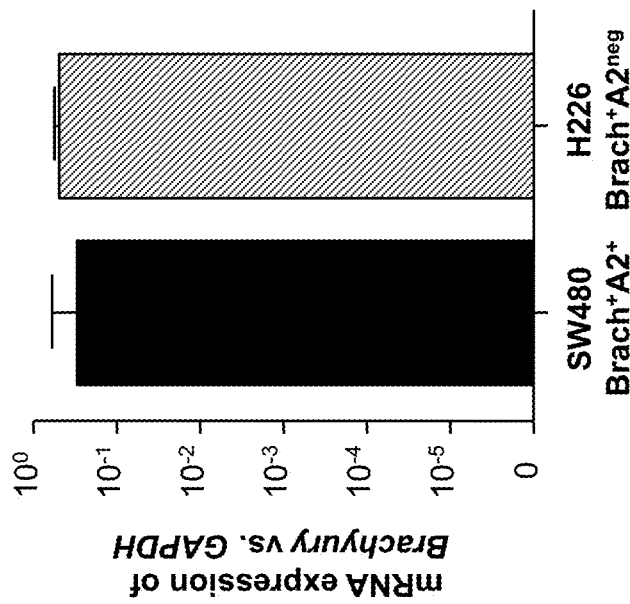
FIG. 4B is a graph showing the expression of Brachyury mRNA relative to that of a control gene (GAPDH) in the SW480 and H226 tumor cells used in the experiment shown in FIG. 4A.
Figure 4A:
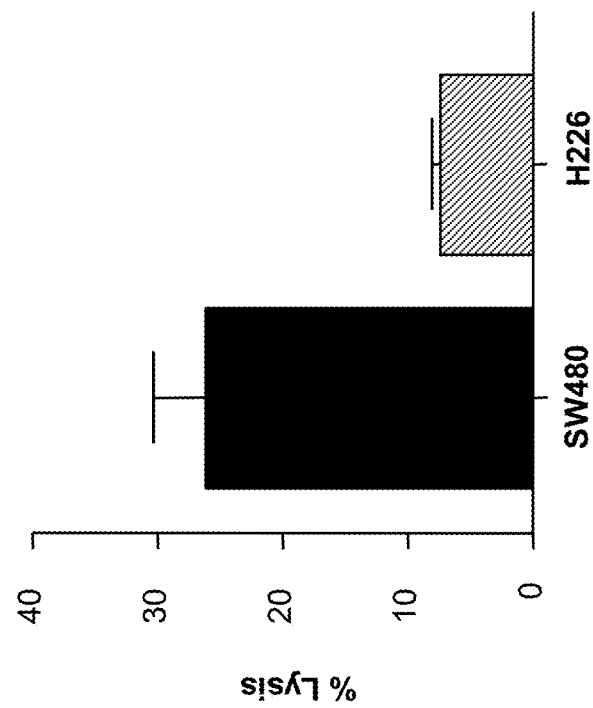
FIG. 4A is a graph showing that Brachyury-specific T cells from healthy donor PBMCs stimulated with a yeast-Brachyury immunotherapeutic composition specifically lyse tumor cells that have the appropriate MHC (SW480, HLA-A2 positive/Brachyury high) versus H226 carcinoma cells (HLA-A2 negative/Brachyury high).

In order to show that yeast-Brachyury immunotherapy can induce Brachyury-specific CTLs in the absence of pulsing with a specific peptide (i.e., by generating CTLs against potentially multiple different CTL epitopes), additional experiments were performed using normal donor T cells expanded in vitro using only the yeast-Brachyury immunotherapeutic composition, GI-6301 (i.e., no peptide pulse). Briefly, Brachyury-specific T cells from normal donor PBMCs (donor 19063) were expanded in vitro by using DCs incubated with GI-6301 for 2 cycles of IVS (as described in Example 4). At day 5, CD8+ T cells were isolated and used in an overnight CTL assay against SW480 (HLA-A2 positive/Brachyury high) and H226 (HLA-A2 negative/Brachyury high) tumor cells, at an effector:target (ET) ratio of 15:1. FIG. 4A shows the percentage of specific lysis of SW480 and H226 tumor cells. FIG. 4B shows the expression of Brachyury mRNA relative to that of GAPDH in SW480 and H226 tumor cells by real-time RT-PCR. These experiments further demonstrate that yeast-Brachyury immunotherapeutic composition can generate Brachyury-specific CTLs that are capable of killing a Brachyury-expressing tumor cell.

Example 6

The following example demonstrates that a yeast-Brachyury composition of the invention can expand Brachyury-specific T cells from cancer patients.

In this experiment, DCs were prepared from the PBMCs of two breast cancer patients, post-vaccination with viral vector vaccines comprising CEA and MUC-1 antigens. The DCs were prepared in a 5-day culture in presence of GM-CSF and IL-4 as described in Example 4, followed by incubation in presence of Brachyury yeast (GI-6301) at a ratio of yeast:DCs=1:1. After 48-hours co-culture, the DCs were used as APCs for stimulation of autologous T cells. Each cycle of IVS consisted of 3 days in absence of IL-2, following by 4 additional days in presence of 20 U/ml of recombinant IL-2. Shown in Table 5 is the percentage of $CD8^-$ T cells (IVS1) that stained positive with a control tetramer or a tetramer specific for the Brachyury peptide Tp2.

TABLE 5

| Patient | Stimulation | Control Tetramer | Brachyury Tetramer |
|---|---|---|---|
| Breast Pt 01 | Brachyury Yeast | 0.11 | 0.42 |
| Breast Pt 10 | Brachyury Yeast | 0.23 | 0.91 |

The results in Table 5 demonstrate that stimulation of T cells from breast cancer donors with a yeast-Brachyury immunotherapeutic of the invention increases the percentage of tetramer-positive $CD8^+$ T cells in a majority of the donors, as compared to controls, indicating that T cells from donors with ongoing cancer have the capacity to recognize Brachyury as an immunogen.

Example 7

The following Example demonstrates the generation of $CD4^+$ T cell responses specific for Brachyury in vivo using yeast-Brachyury immunotherapy.

In this experiment, C57BL/6 mice were vaccinated weekly for a total of 4 times with 4 YU of yeast-hBrachyury (GI-6301), administered at four separate injection sites at 1 YU per site). Two weeks after the final boost, the mice were sacrificed and $CD4^+$ T cells were purified and assayed for proliferation in presence of various concentrations of Brachyury purified protein (obtained from insect cells). As a control, l3-Gal was used at 40 μg/ml.

The results showing the proliferation of $CD4^+$ T cells isolated from the spleens of animals vaccinated with yeast-control (YVEC, see Example 4) and yeast-hBrachyury (GI-6301) are shown in FIG. 5. FIG. 5 shows that immunization with yeast-Brachyury (GI-6301) generates Brachyury-specific $CD4^+$ T cells.

Example 8

The following example demonstrates that immunization with yeast-Brachyury immunotherapeutic composition reduces Brachyury-expressing tumors in vivo.

In this experiment, C57BL/6 mice received $1 \times 10^6$ MC38-phBrachyury cells (MC38 tumor cells expressing a recombinant human Brachyury) via the tail vein (day 0). Four days post-tumor implantation, animals began receiving weekly vaccinations with yeast control (YVEC, see Example 4) versus yeast-hBrachyury (GI-6301), administered at a dose of 1 YU per site at four different sites (4 YU total per dose).

Figure 6:
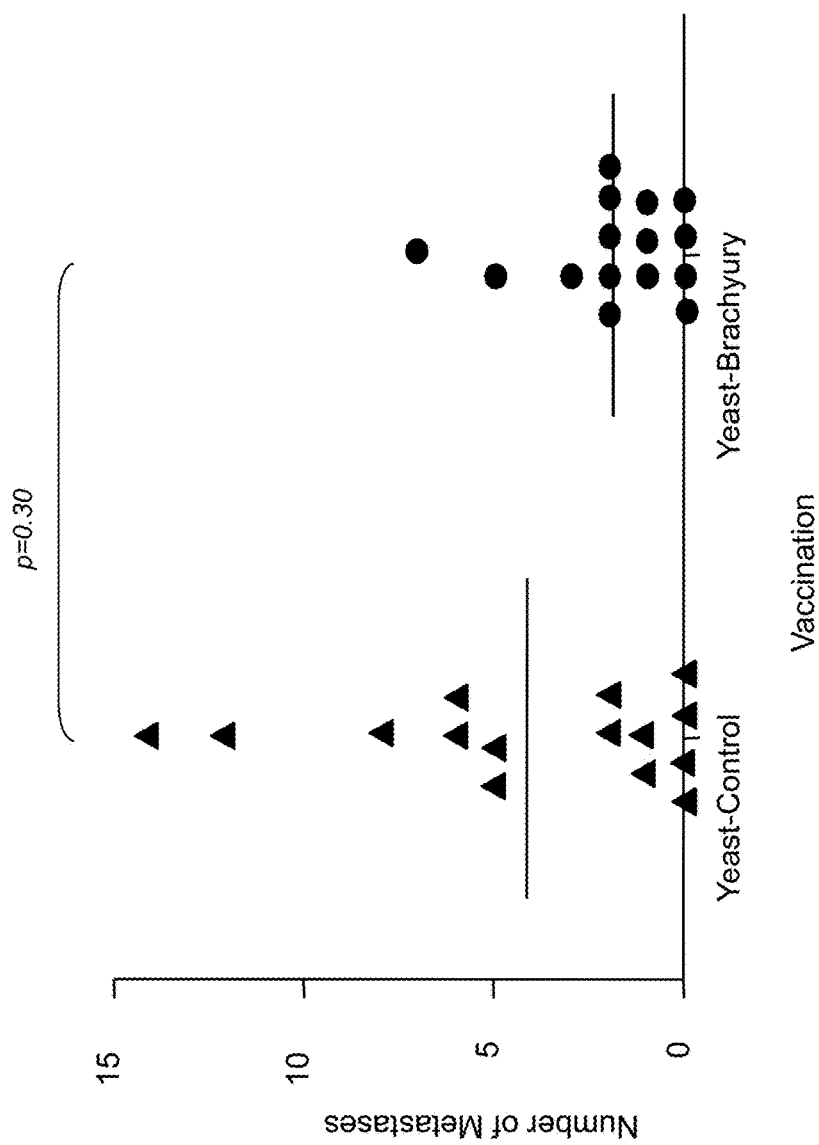
FIG. 6 graph showing that administration of a yeast-Brachyury immunotherapeutic composition (GI-6301, circles) of the invention shows a trend towards reducing Brachyury-expressing tumors in mice compared to mice receiving yeast alone (no Brachyury antigen).

At day 40 post-tumor implantation, animals were sacrificed and the number of lung tumor nodules was evaluated. Results from two combined experiments are shown in FIG. 6. Table 6 shows the mean lung tumor number (±SEM) and the number (and percentage) of animals bearing≥5 lung nodules.

TABLE 6

| Vaccine Treatment | Lung Tumors (mean ± SEM) | Animals Bearing ≥ 5 Lung Nodules (%) |
|---|---|---|
| Yeast-Control (YVEC) | 4.1 ± 1.2 | 7/15 (46.7%) |
| Yeast-Brachyury (GI-6301) | 1.9 ± 0.5 | 2/15 (13.3%) |

The results in FIG. 6 and Table 6 demonstrate that administration of a yeast-Brachyury immunotherapeutic composition of the invention is capable of reducing Brachyury-expressing tumors in mice, as compared to mice receiving yeast alone (no Brachyury antigen).

Example 9

The following example demonstrates the generation of Brachyury-specific $CD4^+$ T cell responses in vitro using yeast-Brachyury immunotherapy in human peripheral blood mononuclear cells (PBMCs) obtained from healthy donors.

In the following experiments, a full-length human Brachyury protein was expressed in insect cells via baculovirus expression and subsequently purified.

Dendritic cells (DCs) were prepared from PBMCs of healthy donors by 5-day culture with GM-CSF and IL-4 and subsequently treated in vitro with yeast-control (YVEC, see Example 4) or yeast-Brachyury (GI-6301, see Examples 1 and 2) (ratio yeast:DCs=1:1). After 48 hours, DCs were harvested, irradiated (30 Gy) and used for stimulation of autologous PBMCs, at a ratio DC:PBMCs=1:10. On day 3, IL-2 (10 U/ml) was added to the cultures. On day 7, stimulated T cells were harvested and subsequently tested for IFN-γ production in response to autologous, irradiated PBMCs (ratio T cells:PBMCs=1:3) alone or in the presence of 10 μg/ml of purified Brachyury protein or control human serum albumin protein. Following 96 hours stimulation, supernatants were collected and evaluated for IFN-γ levels by ELISA assay. A total of 9 healthy donors were evaluated, with 3/9 donors demonstrating Brachyury-specific $CD4^-$ T-cell responses post-stimulation in vitro with yeast-Brachyury-treated DCs. Results for 3 positive cases are presented in Table 7 (values indicate the levels of IFN-γ in response to Brachyury protein, after subtracting background levels induced by stimulation with control Human Serum Albumin protein; for donor 3, two cycles of stimulation were performed prior to evaluating response to Brachyury protein).

TABLE 7

| Donor ID | DC stimulation | ΔIFN-γ (pg/ml) |
|---|---|---|
| 1 | Yeast-control | 1500.0 |
|   | Yeast-Brachyury | 2950.0 |
| 2 | Yeast-control | 13.4 |
|   | Yeast-Brachyury | 889.0 |
| 3 | Yeast-control | 17.4 |
|   | Yeast-Brachyury | 102.8 |

Six additional healthy donors were evaluated for $CD4^+$ T cell responses to the Brachyury protein, following in vitro stimulation with yeast-Brachyury (GI-6301)-treated DCs by intracellular cytokine staining of IFN-γ in CD4+ cells. Dendritic cells were prepared from PBMCs of healthy donors by 5-day culture with GMCSF and IL-4 and subsequently treated in vitro with yeast-control (YVEC) or yeast-Brachyury (GI-6301) (ratio yeast:DCs=1:1). After 48 hours, the DCs were harvested, irradiated (30 Gy) and used for stimulation of autologous PBMCs, at a ratio DC:PBMCs=1:10. On day 3, IL-2 (10 U/ml) was added to the cultures. On day 7, stimulated T cells were harvested and subsequently tested for IFN-γ production in response to autologous PBMCs (ratio T cells:PBMCs=1:3) alone or in the presence of 10 µg/ml of purified Brachyury protein or control human serum albumin protein. Following 2 hours stimulation, BD GOLGISTOP™ Protein Transport Inhibitor (BD Biosciences) was added to the cultures. Following 4 hours stimulation, cells were harvested, permeabilized, and stained for CD4 and IFN-γ utilizing anti-CD4 PerCP-Cy5.5 and anti-IFN-γ FITC antibodies (BD Biosciences). A total of 6 healthy donors were evaluated, with 2/6 donors demonstrating Brachyury-specific CD4+ T-cell responses post-stimulation in vitro with yeast-Brachyury treated DCs. Results for positive cases are shown in Table 8 (values indicate the percentage of T cells that were simultaneously positive for CD4 and intracellular IFN-γ in response to control human serum albumin (HSA) or Brachyury protein, after subtracting background levels induced by stimulation with PBMCs alone).

TABLE 8

| Donor | Number of stimulations in vitro | % CD4+/IFN-γ+ cells | |
|---|---|---|---|
| | | HSA | Brachyury |
| 4 | 1 | 0.07 | 0.24 |
| 5 | 2 | 0.00 | 1.00 |

Example 10

The following example demonstrates that a yeast-Brachyury immunotherapy composition expressing a Brachyury agonist antigen generates Brachyury-specific T cells from a prostate cancer patient.

To generate a Brachyury-specific T-cell line, immature autologous dendritic cells (DCs) were exposed to the yeast-Brachyury immunotherapy composition known at GI-6305 (see Example 3) at a ratio of DCs:GI-6305=1:1 for 48 hours, and subsequently used as antigen presenting cells (APCs) to stimulate autologous non-adherent cells at an effector-to-APC ratio of 10:1. Cultures were incubated for 3 days at 37° C., in a humidified atmosphere containing 5% $CO_2$, and subsequently supplemented with recombinant human IL-2 at a concentration of 20 U/ml for an additional 7 days. The 10-day culture constituted one in vitro stimulation (IVS) cycle. T cells were restimulated with GI-6305-exposed autologous DCs as described above on day 11, to begin the next IVS cycle. GI-6305-exposed autologous DCs were used as APCs for three IVS cycles. After the third IVS, irradiated (23,000 rads) autologous EBV-transformed B cells, pulsed with an agonist Brachyury peptide, WLLPGT-STV (SEQ ID NO:13), were used as APCs. A Brachyury-specific T cell line, denoted, T-2-BR-A, was established. This T cell line was used in the immunoassays described below.

Table 9 demonstrates that Brachyury-specific T cells (T-2-BR-A) release significant levels of IFN-γ after stimulation with allogeneic DCs treated with GI-6305, whereas control yeast (YVEC, see Example 4) did not stimulate the release of IFN-γ by T-2-BR-A cells. Results are expressed in pg/ml/$10^5$ T cells. Briefly, allogeneic HLA-A2 positive DCs from a normal donor were treated with GI-6305 for 48 hours at various yeast to DC ratios (indicated in Table 9) and then used to stimulate Brachyury agonist epitope-specific T cells (T-2-BR-A). In this experiment, the DC to T cell ratio was 1:10.

TABLE 9

| Dendritic Cells | Treatment | Yeast/DC Ratio | T Cells | IFN-γ |
|---|---|---|---|---|
| + | Control yeast | 10:1 | − | <15.6 |
| + | Control yeast | 10:1 | + | <15.6 |
| − | — | — | + | 52.1 |
| + | GI-6305 | 10:1 | − | <15.6 |
| + | GI-6305 | 10:1 | + | 589.0 |
| + | GI-6305 | 5:1 | − | <15.6 |
| + | GI-6305 | 5:1 | + | 661.1 |
| + | GI-6305 | 2.5:1 | − | <15.6 |
| + | GI-6305 | 2.5:1 | + | 341.3 |
| + | GI-6305 | 1:1 | − | <15.6 |
| + | GI-6305 | 1:1 | + | 388.2 |

Table 10 demonstrates that Brachyury-specific T cells established by using GI-6305 treated DCs can effectively lyse MDA-MB-231 breast cancer cells that are HLA-A2 positive/Brachyury positive, but do not lyse ASPC-1 pancreatic cancer cells that are HLA-A2 negative/Brachyury positive. Briefly, the Brachyury-specific T cell line T-2-BR-A was used at IVS-6 in an overnight cytotoxic T lymphocyte (CTL) assay against MDA-MB-231 (HLA-A2−/Brachyury+) and ASPC-1 (HLA-A2−/Brachyury+) tumor cell targets, at the indicated effector:target (ET) ratios (see Table 10). Results are expressed as the percentage of specific lysis.

TABLE 10

| E:T ratio | MDA-MB-231 | ASPC-1 |
|---|---|---|
| 25:1 | 52.2 (2.8) | −5.1 (2.6) |
| 12.5:1 | 23.8 (1.4) | 0.2 (5.6) |
| 6.25:1 | 13.9 (4.4) | 2.3 (3.3) |

Figure 7A:
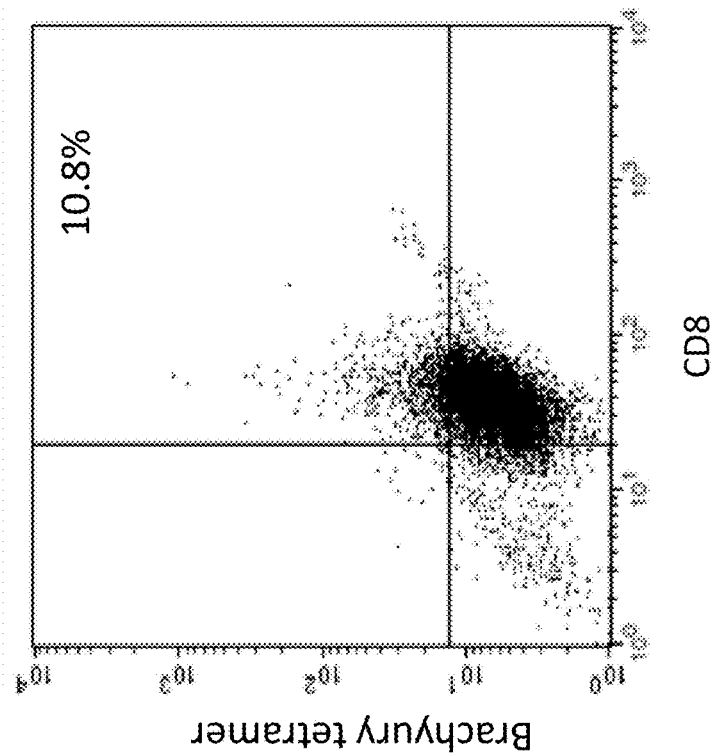
FIGS. 7A and 7B are flow cytometry analyses showing that the Brachyury-specific T cell line, T-2-BR-A, binds to a Brachyury-specific HLA-A2 tetramer (FIG. 7B) and not to a control tetramer (FIG. 7A).
Figure 7B:
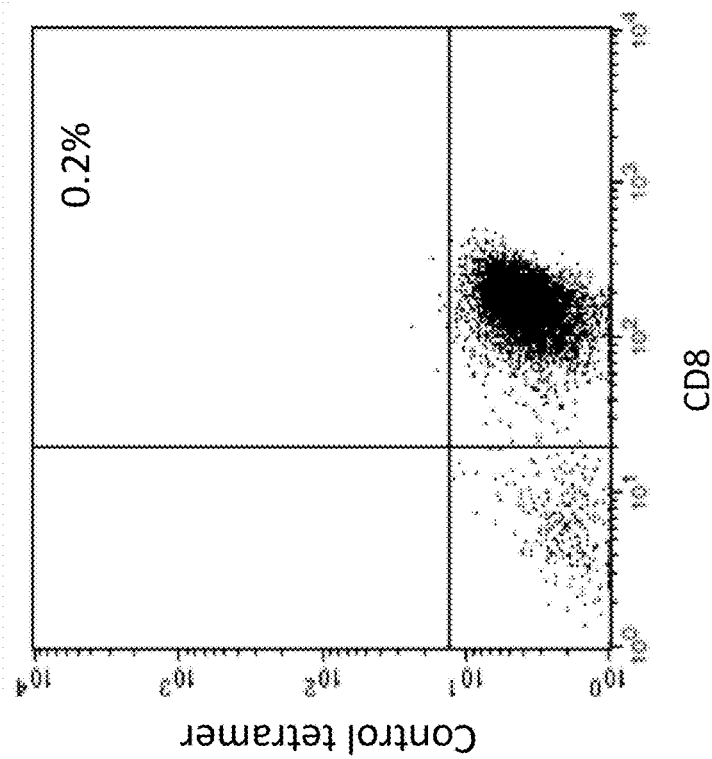

In another experiment, the ability of the T-2-BR-A cell line to bind to Brachyury-specific HLA-A2 tetramers was evaluated. Briefly, T-2-BR-A cells (used at IVS-4) were stained with a control tetramer or a tetramer specific for the Brachyury agonist peptide. FIGS. 7A and 7B show that 10.8% of CD8+ T cells in the T-2-BR-A cell line generated with GI-6305-treated DCs specifically bind to a Brachyury-HLA-A2 tetramer (FIG. 7B) and not to a control tetramer (FIG. 7A).

Figure 8:
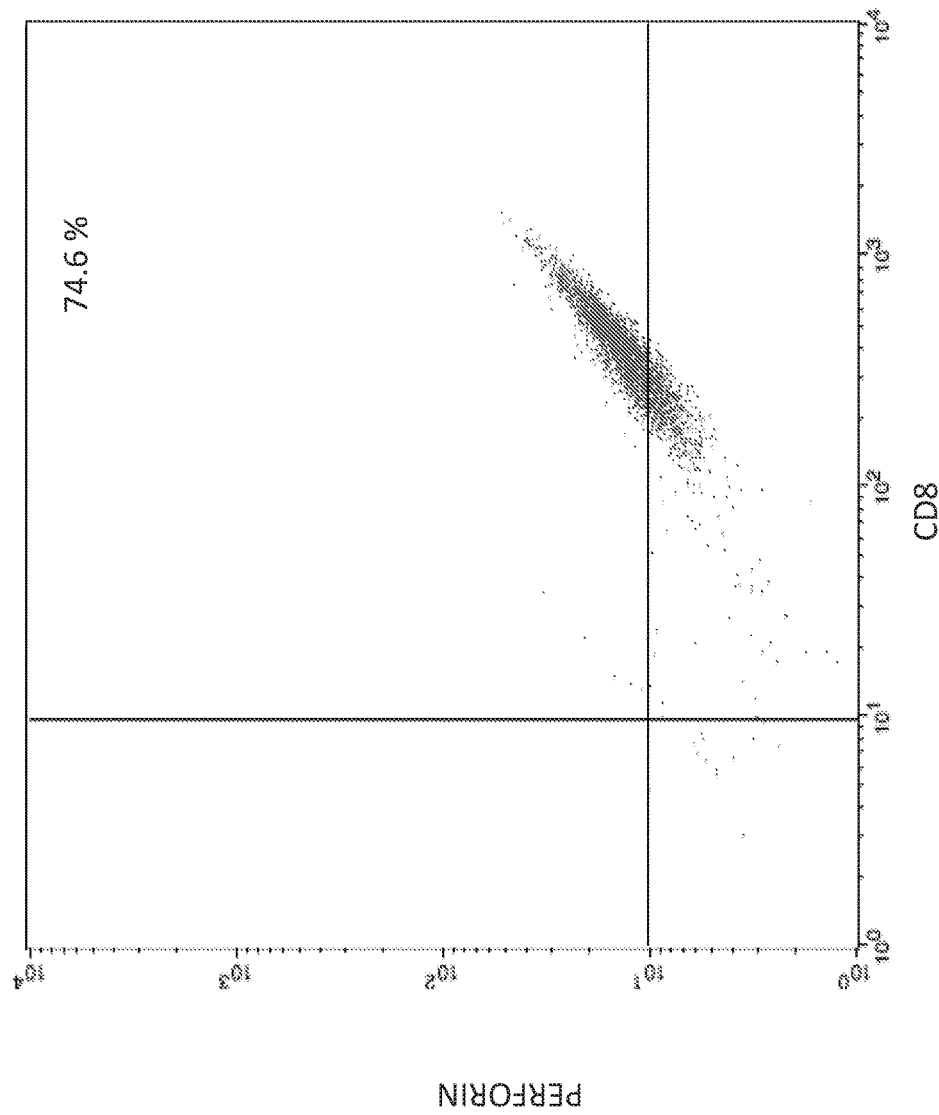
FIG. 8 is a flow cytometry analysis showing the expression of perforin in the Brachyury-specific T cell line, T-2-BR-A, after stimulation with Brachyury agonist peptide-pulsed autologous B cells.

Perforin expression of the T-2-BR-A T cell line was analyzed by flow cytometry (perforin is a mediator of the cytolytic activity of cytotoxic T lymphocytes (CTLs)). Briefly, T cells were tested on day 5 after restimulation with Brachyury agonist peptide-pulsed autologous EBV transformed B cells. FIG. 8 shows the expression of perforin in the T-2-BR-A cell line after stimulation with Brachyury agonist peptide-pulsed autologous B cells, further demonstrating the cytotoxic capability of this Brachyury-specific T cell line, which was generated using GI-6305-treated DCs.

Example 11

The following example describes a phase 1 clinical trial in subjects with Brachyury-positive cancer.

An open-label, sequential dose-escalation, phase 1 clinical trial has been initiated using the yeast-Brachyury immunotherapy composition known as GI-6301, described in Examples 1, 2, and 4-9. Under this clinical trial protocol, 9-18 cancer patients (3-6 patients per dose cohort) are administered the yeast-Brachyury immunotherapy composition known as GI-6301 in a sequential dose cohort escalation protocol utilizing dose ranges of 4 Y.U. (1 Y.U.×4 sites, meaning that 1 Y.U. of GI-6301 is administered at 4 different sites on the body of the patient each visit), 16 Y.U. (4 Y.U.×4 sites) and 40 Y.U. (10 Y.U.×4 sites), administered subcutaneously. GI-6301 is administered at 2 week intervals for a total of 7 visits (~3 months), and then monthly thereafter until the patients meet off-study criteria. An expansion cohort of patients (n=10) at maximum tolerated dose (MTD) or the observed best dose are selected for additional study. The results are monitoring safety and tolerability as a primary endpoint, and in the expanded cohort, whether a significant change in T cell precursors is detectable as measured by an increase in Brachyury-specific T cells in ELISpot assay and proliferation in response to Brachyury protein (e.g., Brachyury-specific $CD8^+$ or $CD4^+$ T cells emerging or expanding on treatment). As secondary endpoints, clinical benefit, such as progression-free survival, clinical radiographic response, reduction in serum markers, and/or reduction in circulating tumor cells is measured, as well as parameters of general immune activation, including frequency of immune cell subsets in peripheral blood ($CD8^+$ memory/effector T cells, $CD4^+$ memory/effector T cells, Tregs, NK cells, DCs) and changes in serum levels of cytokines (e.g., IFN-$\gamma$, IL-10, IL-12, IL-2, IL-4, TGF-$\beta$, etc.).

GI-6301 is expected to be safe and well-tolerated with no significant toxicities. In addition, GI-6301 is expected to produce treatment-emergent Brachyury-specific T cell responses or an improvement in pre-existing Brachyury-specific baseline T cell responses at least some or a majority of patients. Some patients are also expected to have stabilized disease.

In an additional study or an expansion of this study, the yeast-Brachyury immunotherapeutic composition known as GI-6305 (see Example 3) is administered to an additional cohort of patients, utilizing the maximum tolerated dose or observed best dose determined above, and the same primary and secondary endpoints are measured. GI-6305 is also expected to be safe and well-tolerated with no significant toxicities, as well as produce treatment-emergent Brachyury-specific T cell responses or an improvement in pre-existing Brachyury-specific baseline T cell responses at least some or a majority of patients. Some patients are also expected to have stabilized disease.

Example 12

The following example describes a phase 2 clinical trial using yeast-Brachyury immunotherapeutic compositions.

A randomized phase 2 clinical trial in patients with breast cancer is run using a yeast-Brachyury immunotherapeutic composition as described in Example 1 and 2 (e.g., GI-6301) or in Example 3 (GI-6305). At least 100 or more subjects with Stage I, II or III Brachyury-positive breast cancer are enrolled. Subject inclusion criteria can include subjects with Grade 1, 2 or 3 cancers. Subject including criteria can also include subjects with "triple negative" breast cancer (cancers that are negative for each of estrogen receptor (ER), progesterone receptor (PR) and HER2). Subject inclusion criteria can also include patients with lymph node-negative cancer.

The trial is run as a double-blind or open-label, placebo-controlled, multi-center trial. All patients receive standard of care therapy with treatment arm patients receiving several serial injections of yeast-Brachyury immunotherapeutic composition during treatment. The primary endpoint is recurrence free survival or overall survival. Additional endpoints can include antigen-specific T cell responses (e.g., Brachyury-specific $CD8^-$ T cells emerging or expanding on treatment), maintenance of lymph node negativity, progression to metastases, and Brachyury expression in tumor cells.

The yeast-Brachyury immunotherapeutic composition is expected to be safe and well-tolerated with no significant toxicities. In addition, the yeast-Brachyury immunotherapeutic composition is expected to produce treatment-emergent Brachyury-specific T cell responses and/or an improvement in pre-existing Brachyury-specific baseline T cell responses in at least some or a majority of patients. Some or a majority of patients are also expected to have stabilized disease, maintain lymph node negativity, and/or prevention, reduction or arrest in metastatic progression.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A method to treat cancer in an individual, comprising administering to an individual who has cancer, an immunotherapeutic composition comprising:
   a) a whole, inactivated yeast; and
   b) a cancer antigen comprising a Brachyury antigen, wherein the Brachyury antigen comprises SEQ ID NO:6, positions 2-435 of SEQ ID NO:6, SEQ ID NO:18, or positions 2-435 of SEQ ID NO:18.

2. The method of claim 1, wherein the individual has a stage I cancer.

3. The method of claim 1, wherein the individual has a stage II cancer.

4. The method of claim 1, wherein the individual has a stage III cancer.

5. The method of claim 1, wherein the individual has a stage IV cancer.

6. The method of claim 1, wherein the cancer is selected from the group consisting of: breast cancer, small intestine cancer, stomach cancer, pancreatic cancer, kidney cancer, bladder cancer, uterine cancer, ovarian cancer, testicular cancer, lung cancer, colon cancer, prostate cancer, chronic lymphocytic leukemia (CLL), Epstein-Barr virus transformed B cells, Burkitt's lymphoma, Hodgkin's lymphoma, and metastatic cancers thereof.

7. The method of claim 1, wherein the whole yeast is heat-inactivated.

8. The method of claim 1, wherein the yeast expresses the antigen.

9. The method of claim 1, wherein the yeast is from a genus selected from the group consisting of: *Saccharomyces, Candida, Cryptococcus, Hansenula, Kluyveromyces, Pichia, Rhodotorula, Schizosaccharomyces* and *Yarrowia*.

10. The method of claim 1, wherein the yeast is from *Saccharomyces*.

11. The method of claim 10, wherein the yeast is from *Saccharomyces cerevisiae*.

12. The method of claim 1, wherein the composition is formulated in a pharmaceutically acceptable excipient suitable for administration by injection of a subject.

13. The method of claim 1, wherein the subject is administered the immunotherapeutic composition in a dose from about 10 Y.U. to about 100 Y.U.

14. The method of claim 1, wherein the subject is administered the immunotherapeutic composition in a dose from about 10 Y.U. to about 40 Y.U.

15. The method of claim 1, wherein the immunotherapeutic composition is administered weekly.

16. The method of claim 1, wherein the immunotherapeutic composition is administered every other week.

17. The method of claim 1, wherein the immunotherapeutic composition is administered monthly.

18. The method of claim 1, wherein the immunotherapeutic composition is administered weekly for 5 weeks followed by monthly.

19. The method of claim 1, wherein the immunotherapeutic composition is administered at two week intervals for 7 rounds of treatment, followed by monthly.

20. The method of claim 1, wherein the immunotherapeutic composition is administered at more than one site on the individual to a form a single dose.

21. The method of claim 1, wherein the immunotherapeutic composition is administered concurrently with another therapy for cancer.

22. A method to treat cancer in an individual, comprising administering to an individual who has cancer, an immunotherapeutic composition comprising:
a. a whole, inactivated yeast; and
b. a Brachyury fusion protein comprising the amino acid sequence of positions 2-435 of SEQ ID NO:6 or the amino acid sequence of positions 2-435 of SEQ ID NO:18; wherein the Brachyury fusion protein is expressed by the yeast; and wherein the composition elicits a Brachyury-specific T cell response.

23. An immunotherapeutic composition comprising:
a) a whole, inactivated yeast;
b) a cancer antigen comprising a Brachyury antigen, wherein the Brachyury antigen comprises SEQ ID NO:6, positions 2-435 of SEQ ID NO:6, SEQ ID NO:18, or positions 2-435 of SEQ ID NO:18; and
c) a pharmaceutically acceptable excipient suitable for administration to a human.

24. The immunotherapeutic composition of claim 23, wherein the whole yeast is heat-inactivated.

25. The immunotherapeutic composition of claim 23, wherein the yeast expresses the antigen.

26. The immunotherapeutic composition of claim 23, wherein the yeast is from a genus selected from the group consisting of: *Saccharomyces, Candida, Cryptococcus, Hansenula, Kluyveromyces, Pichia, Rhodotorula, Schizosaccharomyces* and *Yarrowia*.

27. The immunotherapeutic composition of claim 23, wherein the yeast is from *Saccharomyces*.

28. The immunotherapeutic composition of claim 23, wherein the yeast is from *Saccharomyces cerevisiae*.

29. The method of claim 22, wherein the yeast is *Saccharomyces cerevisiae*.

30. A recombinant nucleic acid molecule encoding a fusion protein comprising at least one Brachyury antigen, wherein the Brachyury antigen comprises SEQ ID NO:6, positions 2-435 of SEQ ID NO:6, SEQ ID NO:18, or positions 2-435 of SEQ ID NO:18, and wherein the fusion protein was expressed by yeast.

31. A fusion protein comprising at least one Brachyury antigen, wherein the Brachyury antigen comprises SEQ ID NO:6, positions 2-435 of SEQ ID NO:6, SEQ ID NO:18, or positions 2-435 of SEQ ID NO:18, and wherein the fusion protein was expressed by yeast.

32. A method to treat cancer in an individual, comprising administering to an individual who has cancer, an immunotherapeutic composition comprising:
a) a whole, inactivated yeast;
b) a cancer antigen comprising a Brachyury antigen, wherein the Brachyury antigen comprises SEQ ID NO:6, positions 2-435 of SEQ ID NO:6, SEQ ID NO:18, or positions 2-435 of SEQ ID NO:18; and
c) an agent selected from the group consisting of an immunotherapeutic virus-based vaccine, a cytokine, a T-cell co-stimulator, a immunomodulator, CD40L, anti-CTLA-4 antibody, anti-PD-1, anti-PD-L1, anti-PD-L2 and combinations thereof.

* * * * *

SEQUENCE LISTING

<160> NUMBER OF SEQ ID NOS: 20

<210> SEQ ID NO 1
<211> LENGTH: 2518
<212> TYPE: DNA
<213> ORGANISM: Homo sapiens
<220> FEATURE:
<221> NAME/KEY: CDS
<222> LOCATION: (494)..(1801)

<400> SEQUENCE: 1

```
tttgcttttg cttatttccg tccatttccc tctctgcgcg cggaccttcc ttttccagat      60
ggtgagagcc gcggggacac ccgacgccgg ggcaggctga tccacgatcc tgggtgtgcg     120
```

```
taacgccgcc tggggctccg tgggcgaggg acgtgtgggg acaggtgcac cggaaactgc    180
cagactggag agttgaggca tcggaggcgc gagaacagca ctactactgc ggcgagacga    240
gcgcggcgca tcccaaagcc cggccaaatg cgctcgtccc tgggagggga gggaggcgcg    300
cctggagcgg ggacagtctt ggtccgcgcc ctcctcccgg gtctgtgccg ggacccggga    360
cccgggagcc gtcgcaggtc tcggtccaag gggccccttt tctcggaagg gcggcggcca    420
agagcaggga aggtggatct caggtagcga gtctgggctt cggggacggc ggggagggga    480
gccggacggg agg atg agc tcc cct ggc acc gag agc gcg gga aag agc      529
            Met Ser Ser Pro Gly Thr Glu Ser Ala Gly Lys Ser
            1               5                   10 ctg cag tac cga gtg gac cac ctg ctg agc gcc gtg gag aat gag ctg    577
Leu Gln Tyr Arg Val Asp His Leu Leu Ser Ala Val Glu Asn Glu Leu
        15                  20                  25 cag gcg ggc agc gag aag ggc gac ccc aca gag cgc gaa ctg cgc gtg    625
Gln Ala Gly Ser Glu Lys Gly Asp Pro Thr Glu Arg Glu Leu Arg Val
    30                  35                  40 ggc ctg gag gag agc gag ctg tgg ctg cgc ttc aag gag ctc acc aat    673
Gly Leu Glu Glu Ser Glu Leu Trp Leu Arg Phe Lys Glu Leu Thr Asn
45                  50                  55                  60 gag atg atc gtg acc aag aac ggc agg agg atg ttt ccg gtg ctg aag    721
Glu Met Ile Val Thr Lys Asn Gly Arg Arg Met Phe Pro Val Leu Lys
                65                  70                  75 gtg aac gtg tct ggc ctg gac ccc aac gcc atg tac tcc ttc ctg ctg    769
Val Asn Val Ser Gly Leu Asp Pro Asn Ala Met Tyr Ser Phe Leu Leu
            80                  85                  90 gac ttc gtg gcg gcg gac aac cac cgc tgg aag tac gtg aac ggg gaa    817
Asp Phe Val Ala Ala Asp Asn His Arg Trp Lys Tyr Val Asn Gly Glu
        95                  100                 105 tgg gtg ccg ggg ggc aag ccg gag ccg cag gcg ccc agc tgc gtc tac    865
Trp Val Pro Gly Gly Lys Pro Glu Pro Gln Ala Pro Ser Cys Val Tyr
    110                 115                 120 atc cac ccc gac tcg ccc aac ttc ggg gcc cac tgg atg aag gct ccc    913
Ile His Pro Asp Ser Pro Asn Phe Gly Ala His Trp Met Lys Ala Pro
125                 130                 135                 140 gtc tcc ttc agc aaa gtc aag ctc acc aac aag ctc aac gga ggg ggc    961
Val Ser Phe Ser Lys Val Lys Leu Thr Asn Lys Leu Asn Gly Gly Gly
                145                 150                 155 cag atc atg ctg aac tcc ttg cat aag tat gag cct cga atc cac ata    1009
Gln Ile Met Leu Asn Ser Leu His Lys Tyr Glu Pro Arg Ile His Ile
            160                 165                 170 gtg aga gtt ggg ggt cca cag cgc atg atc acc agc cac tgc ttc cct    1057
Val Arg Val Gly Gly Pro Gln Arg Met Ile Thr Ser His Cys Phe Pro
        175                 180                 185 gag acc cag ttc ata gcg gtg act gct tat cag aac gag gag atc aca    1105
Glu Thr Gln Phe Ile Ala Val Thr Ala Tyr Gln Asn Glu Glu Ile Thr
    190                 195                 200 gct ctt aaa att aag tac aat cca ttt gca aaa gct ttc ctt gat gca    1153
Ala Leu Lys Ile Lys Tyr Asn Pro Phe Ala Lys Ala Phe Leu Asp Ala
205                 210                 215                 220 aag gaa aga agt gat cac aaa gag atg atg gag gaa ccc gga gac agc    1201
Lys Glu Arg Ser Asp His Lys Glu Met Met Glu Glu Pro Gly Asp Ser
                225                 230                 235 cag caa cct ggg tac tcc caa tgg ggg tgg ctt ctt cct gga acc agc    1249
Gln Gln Pro Gly Tyr Ser Gln Trp Gly Trp Leu Leu Pro Gly Thr Ser
            240                 245                 250 acc ctg tgt cca cct gca aat cct cat cct cag ttt gga ggt gcc ctc    1297
Thr Leu Cys Pro Pro Ala Asn Pro His Pro Gln Phe Gly Gly Ala Leu
```

```
                 255                 260                 265
tcc ctc ccc tcc acg cac agc tgt gac agg tac cca acc ctg agg agc    1345
Ser Leu Pro Ser Thr His Ser Cys Asp Arg Tyr Pro Thr Leu Arg Ser
    270                 275                 280 cac cgg tcc tca ccc tac ccc agc ccc tat gct cat cgg aac aat tct    1393
His Arg Ser Ser Pro Tyr Pro Ser Pro Tyr Ala His Arg Asn Asn Ser
285                 290                 295                 300 cca acc tat tct gac aac tca cct gca tgt tta tcc atg ctg caa tcc    1441
Pro Thr Tyr Ser Asp Asn Ser Pro Ala Cys Leu Ser Met Leu Gln Ser
                305                 310                 315 cat gac aat tgg tcc agc ctt gga atg cct gcc cat ccc agc atg ctc    1489
His Asp Asn Trp Ser Ser Leu Gly Met Pro Ala His Pro Ser Met Leu
            320                 325                 330 ccc gtg agc cac aat gcc agc cca cct acc agc tcc agt cag tac ccc    1537
Pro Val Ser His Asn Ala Ser Pro Pro Thr Ser Ser Ser Gln Tyr Pro
        335                 340                 345 agc ctg tgg tct gtg agc aac ggc gcc gtc acc ccg ggc tcc cag gca    1585
Ser Leu Trp Ser Val Ser Asn Gly Ala Val Thr Pro Gly Ser Gln Ala
    350                 355                 360 gca gcc gtg tcc aac ggg ctg ggg gcc cag ttc ttc cgg ggc tcc ccc    1633
Ala Ala Val Ser Asn Gly Leu Gly Ala Gln Phe Phe Arg Gly Ser Pro
365                 370                 375                 380 gcg cac tac aca ccc ctc acc cat ccg gtc tcg gcg ccc tct tcc tcg    1681
Ala His Tyr Thr Pro Leu Thr His Pro Val Ser Ala Pro Ser Ser Ser
                385                 390                 395 gga tcc cca ctg tac gaa ggg gcg gcc gcg gcc aca gac atc gtg gac    1729
Gly Ser Pro Leu Tyr Glu Gly Ala Ala Ala Ala Thr Asp Ile Val Asp
            400                 405                 410 agc cag tac gac gcc gca gcc caa ggc cgc ctc ata gcc tca tgg aca    1777
Ser Gln Tyr Asp Ala Ala Ala Gln Gly Arg Leu Ile Ala Ser Trp Thr
        415                 420                 425 cct gtg tcg cca cct tcc atg tga agcagcaagg cccaggtccc gaaagatgca   1831
Pro Val Ser Pro Pro Ser Met
    430             435 gtgactttttt gtcgtggcag ccagtggtga ctggattgac ctactaggta cccagtggca  1891
gtctcaggtt aagaaggaaa tgcagcctca gtaacttcct tttcaaagca gtggaggagc   1951
acacggcacc tttccccaga gccccagcat cccttgctca cacctgcagt agcggtgctg   2011
tcccaggtgg cttacagatg aacccaactg tggagatgat gcagttggcc caacctcact   2071
gacggtgaaa aaatgtttgc cagggtccag aaacttttt tggtttattt ctcatacagt   2131
gtattggcaa ctttggcaca ccagaatttg taaactccac cagtcctact ttagtgagat   2191
aaaaagcaca ctcttaatct tcttccttgt tgctttcaag tagttagagt tgagctgtta   2251
aggacagaat aaaatcatag ttgaggacag caggttttag ttgaattgaa aatttgactg   2311
ctctgccccc tagaatgtgt gtattttaag catatgtagc taatctcttg tgttgttaaa   2371
ctataactgt ttcatatttt tcttttgaca aagtagccaa agacaatcag cagaaagcat   2431
tttctgcaaa ataaacgcaa tatgcaaaat gtgattcgtc cagttattag tgaagcccct   2491 cctttttgtga gtatttactg tttattg                                     2518

<210> SEQ ID NO 2
<211> LENGTH: 435
<212> TYPE: PRT
<213> ORGANISM: Homo sapiens

<400> SEQUENCE: 2

Met Ser Ser Pro Gly Thr Glu Ser Ala Gly Lys Ser Leu Gln Tyr Arg
```

-continued

```
1               5                   10                  15
Val Asp His Leu Leu Ser Ala Val Glu Asn Glu Leu Gln Ala Gly Ser
                20                  25                  30
Glu Lys Gly Asp Pro Thr Glu Arg Glu Leu Arg Val Gly Leu Glu Glu
                35                  40                  45
Ser Glu Leu Trp Leu Arg Phe Lys Glu Leu Thr Asn Glu Met Ile Val
    50                  55                  60
Thr Lys Asn Gly Arg Arg Met Phe Pro Val Leu Lys Val Asn Val Ser
65                  70                  75                  80
Gly Leu Asp Pro Asn Ala Met Tyr Ser Phe Leu Leu Asp Phe Val Ala
                85                  90                  95
Ala Asp Asn His Arg Trp Lys Tyr Val Asn Gly Glu Trp Val Pro Gly
                100                 105                 110
Gly Lys Pro Glu Pro Gln Ala Pro Ser Cys Val Tyr Ile His Pro Asp
                115                 120                 125
Ser Pro Asn Phe Gly Ala His Trp Met Lys Ala Pro Val Ser Phe Ser
                130                 135                 140
Lys Val Lys Leu Thr Asn Lys Leu Asn Gly Gly Gln Ile Met Leu
145                 150                 155                 160
Asn Ser Leu His Lys Tyr Glu Pro Arg Ile His Ile Val Arg Val Gly
                165                 170                 175
Gly Pro Gln Arg Met Ile Thr Ser His Cys Phe Pro Glu Thr Gln Phe
                180                 185                 190
Ile Ala Val Thr Ala Tyr Gln Asn Glu Glu Ile Thr Ala Leu Lys Ile
                195                 200                 205
Lys Tyr Asn Pro Phe Ala Lys Ala Phe Leu Asp Ala Lys Glu Arg Ser
                210                 215                 220
Asp His Lys Glu Met Met Glu Glu Pro Gly Asp Ser Gln Gln Pro Gly
225                 230                 235                 240
Tyr Ser Gln Trp Gly Trp Leu Leu Pro Gly Thr Ser Thr Leu Cys Pro
                245                 250                 255
Pro Ala Asn Pro His Pro Gln Phe Gly Gly Ala Leu Ser Leu Pro Ser
                260                 265                 270
Thr His Ser Cys Asp Arg Tyr Pro Thr Leu Arg Ser His Arg Ser Ser
                275                 280                 285
Pro Tyr Pro Ser Pro Tyr Ala His Arg Asn Asn Ser Pro Thr Tyr Ser
                290                 295                 300
Asp Asn Ser Pro Ala Cys Leu Ser Met Leu Gln Ser His Asp Asn Trp
305                 310                 315                 320
Ser Ser Leu Gly Met Pro Ala His Pro Ser Met Leu Pro Val Ser His
                325                 330                 335
Asn Ala Ser Pro Pro Thr Ser Ser Ser Gln Tyr Pro Ser Leu Trp Ser
                340                 345                 350
Val Ser Asn Gly Ala Val Thr Pro Gly Ser Gln Ala Ala Ala Val Ser
                355                 360                 365
Asn Gly Leu Gly Ala Gln Phe Phe Arg Gly Ser Pro Ala His Tyr Thr
                370                 375                 380
Pro Leu Thr His Pro Val Ser Ala Pro Ser Ser Ser Gly Ser Pro Leu
385                 390                 395                 400
Tyr Glu Gly Ala Ala Ala Ala Thr Asp Ile Val Asp Ser Gln Tyr Asp
                405                 410                 415
Ala Ala Ala Gln Gly Arg Leu Ile Ala Ser Trp Thr Pro Val Ser Pro
                420                 425                 430
```

```
Pro Ser Met
        435

<210> SEQ ID NO 3
<211> LENGTH: 2046
<212> TYPE: DNA
<213> ORGANISM: Mus musculus
<220> FEATURE:
<221> NAME/KEY: CDS
<222> LOCATION: (109)..(1419)

<400> SEQUENCE: 3
ggctccgcag agtgacccct tttcttggaa aagcggtggc gagagaagtg aaggtggctg      60
ttgggtaggg agtcaagact cctggaaggt ggagagggtg gcgggagg atg agc tcg     117
                                                    Met Ser Ser
                                                      1 ccg ggc aca gag agc gca ggg aag agc ctg cag tac cga gtg gac cac     165
Pro Gly Thr Glu Ser Ala Gly Lys Ser Leu Gln Tyr Arg Val Asp His
      5                  10                  15 ctg ctc agc gcc gtg gag agc gag ctg cag gcg ggc agc gag aag gga     213
Leu Leu Ser Ala Val Glu Ser Glu Leu Gln Ala Gly Ser Glu Lys Gly
 20                  25                  30                  35 gac ccc acc gaa cgc gaa ctg cga gtg ggc ctg gag gag agc gag ctg     261
Asp Pro Thr Glu Arg Glu Leu Arg Val Gly Leu Glu Glu Ser Glu Leu
                 40                  45                  50 tgg ctg cgc ttc aag gag cta act aac gag atg att gtg acc aag aac     309
Trp Leu Arg Phe Lys Glu Leu Thr Asn Glu Met Ile Val Thr Lys Asn
             55                  60                  65 ggc agg agg atg ttc ccg gtg ctg aag gta aat gtg tca ggc ctg gac     357
Gly Arg Arg Met Phe Pro Val Leu Lys Val Asn Val Ser Gly Leu Asp
         70                  75                  80 ccc aat gcc atg tac tct ttc ttg ctg gac ttc gtg acg gct gac aac     405
Pro Asn Ala Met Tyr Ser Phe Leu Leu Asp Phe Val Thr Ala Asp Asn
     85                  90                  95 cac cgc tgg aaa tat gtg aac ggg gag tgg gta cct ggg ggc aaa cca     453
His Arg Trp Lys Tyr Val Asn Gly Glu Trp Val Pro Gly Gly Lys Pro
100                 105                 110                 115 gag cct cag gcg ccc agc tgc gtc tac atc cac cca gac tcg ccc aat     501
Glu Pro Gln Ala Pro Ser Cys Val Tyr Ile His Pro Asp Ser Pro Asn
                120                 125                 130 ttt ggg gcc cac tgg atg aag gcg cct gtg tct ttc agc aaa gtc aaa     549
Phe Gly Ala His Trp Met Lys Ala Pro Val Ser Phe Ser Lys Val Lys
            135                 140                 145 ctc acc aac aag ctc aat gga ggg gga cag atc atg tta aac tcc ttg     597
Leu Thr Asn Lys Leu Asn Gly Gly Gly Gln Ile Met Leu Asn Ser Leu
        150                 155                 160 cat aag tat gaa cct cgg att cac atc gtg aga gtt ggg ggc cga caa     645
His Lys Tyr Glu Pro Arg Ile His Ile Val Arg Val Gly Gly Pro Gln
    165                 170                 175 cgc atg atc acc agc cac tgc ttt ccc gag acc cag ttc ata gct gtg     693
Arg Met Ile Thr Ser His Cys Phe Pro Glu Thr Gln Phe Ile Ala Val
180                 185                 190                 195 act gcc tac cag aat gag gag att aca gcc ctt aaa att aaa tac aac     741
Thr Ala Tyr Gln Asn Glu Glu Ile Thr Ala Leu Lys Ile Lys Tyr Asn
                200                 205                 210 cca ttt gct aaa gcc ttc ctt gat gcc aaa gaa aga aac gac cac aaa     789
Pro Phe Ala Lys Ala Phe Leu Asp Ala Lys Glu Arg Asn Asp His Lys
            215                 220                 225 gat gta atg gag gaa ccg ggg gac tgc cag cag ccg ggg tat tcc caa     837
Asp Val Met Glu Glu Pro Gly Asp Cys Gln Gln Pro Gly Tyr Ser Gln
```

|   |   |   |   |   |   |   |   |   |   |   |   |   |   |   |   |   |
|---|---|---|---|---|---|---|---|---|---|---|---|---|---|---|---|---|
|   |   | 230 |   |   |   |   | 235 |   |   |   |   | 240 |   |   |   |   |

| tgg | ggg | tgg | ctt | gtt | cct | ggt | gct | ggc | acc | ctc | tgc | ccg | cct | gcc | agc | 885 |
|---|---|---|---|---|---|---|---|---|---|---|---|---|---|---|---|---|
| Trp | Gly | Trp | Leu | Val | Pro | Gly | Ala | Gly | Thr | Leu | Cys | Pro | Pro | Ala | Ser |   |
|   | 245 |   |   |   | 250 |   |   |   | 255 |   |   |   |   |   |   |   |

| tcc | cac | cct | cag | ttt | gga | ggc | tcg | ctc | tct | ctc | ccc | tcc | aca | cac | ggc | 933 |
|---|---|---|---|---|---|---|---|---|---|---|---|---|---|---|---|---|
| Ser | His | Pro | Gln | Phe | Gly | Gly | Ser | Leu | Ser | Leu | Pro | Ser | Thr | His | Gly |   |
| 260 |   |   |   |   | 265 |   |   |   |   | 270 |   |   |   |   | 275 |   |

| tgt | gag | agg | tac | cca | gct | cta | agg | aac | cac | cgg | tca | tcg | ccc | tac | ccc | 981 |
|---|---|---|---|---|---|---|---|---|---|---|---|---|---|---|---|---|
| Cys | Glu | Arg | Tyr | Pro | Ala | Leu | Arg | Asn | His | Arg | Ser | Ser | Pro | Tyr | Pro |   |
|   |   |   |   | 280 |   |   |   |   | 285 |   |   |   |   | 290 |   |   |

| agc | ccc | tat | gct | cat | cgg | aac | agc | tct | cca | acc | tat | gcg | gac | aat | tca | 1029 |
|---|---|---|---|---|---|---|---|---|---|---|---|---|---|---|---|---|
| Ser | Pro | Tyr | Ala | His | Arg | Asn | Ser | Ser | Pro | Thr | Tyr | Ala | Asp | Asn | Ser |   |
|   |   |   |   | 295 |   |   |   |   | 300 |   |   |   |   | 305 |   |   |

| tct | gct | tgt | ctg | tcc | atg | ctg | cag | tcc | cat | gat | aac | tgg | tct | agc | ctc | 1077 |
|---|---|---|---|---|---|---|---|---|---|---|---|---|---|---|---|---|
| Ser | Ala | Cys | Leu | Ser | Met | Leu | Gln | Ser | His | Asp | Asn | Trp | Ser | Ser | Leu |   |
|   |   |   | 310 |   |   |   |   | 315 |   |   |   |   | 320 |   |   |   |

| gga | gtg | cct | ggc | cac | acc | agc | atg | ctg | cct | gtg | agt | cat | aac | gcc | agc | 1125 |
|---|---|---|---|---|---|---|---|---|---|---|---|---|---|---|---|---|
| Gly | Val | Pro | Gly | His | Thr | Ser | Met | Leu | Pro | Val | Ser | His | Asn | Ala | Ser |   |
|   |   | 325 |   |   |   |   | 330 |   |   |   |   | 335 |   |   |   |   |

| cca | cct | act | ggc | tct | agc | cag | tat | ccc | agt | ctc | tgg | tct | gtg | agc | aat | 1173 |
|---|---|---|---|---|---|---|---|---|---|---|---|---|---|---|---|---|
| Pro | Pro | Thr | Gly | Ser | Ser | Gln | Tyr | Pro | Ser | Leu | Trp | Ser | Val | Ser | Asn |   |
| 340 |   |   |   |   | 345 |   |   |   |   | 350 |   |   |   |   | 355 |   |

| ggt | acc | atc | acc | cca | ggc | tcc | cag | aca | gct | ggg | gtg | tcc | aac | ggg | ctg | 1221 |
|---|---|---|---|---|---|---|---|---|---|---|---|---|---|---|---|---|
| Gly | Thr | Ile | Thr | Pro | Gly | Ser | Gln | Thr | Ala | Gly | Val | Ser | Asn | Gly | Leu |   |
|   |   |   |   | 360 |   |   |   |   | 365 |   |   |   |   | 370 |   |   |

| gga | gct | cag | ttc | ttt | cga | ggc | tcc | cct | gca | cat | tac | aca | cca | ctg | acg | 1269 |
|---|---|---|---|---|---|---|---|---|---|---|---|---|---|---|---|---|
| Gly | Ala | Gln | Phe | Phe | Arg | Gly | Ser | Pro | Ala | His | Tyr | Thr | Pro | Leu | Thr |   |
|   |   |   | 375 |   |   |   |   | 380 |   |   |   |   | 385 |   |   |   |

| cac | acg | gtc | tca | gct | gcc | acg | tcc | tcg | tct | tct | ggt | tct | ccg | atg | tat | 1317 |
|---|---|---|---|---|---|---|---|---|---|---|---|---|---|---|---|---|
| His | Thr | Val | Ser | Ala | Ala | Thr | Ser | Ser | Ser | Ser | Gly | Ser | Pro | Met | Tyr |   |
|   |   | 390 |   |   |   |   | 395 |   |   |   |   | 400 |   |   |   |   |

| gaa | ggg | gct | gct | aca | gtc | aca | gac | att | tct | gac | agc | cag | tat | gac | acg | 1365 |
|---|---|---|---|---|---|---|---|---|---|---|---|---|---|---|---|---|
| Glu | Gly | Ala | Ala | Thr | Val | Thr | Asp | Ile | Ser | Asp | Ser | Gln | Tyr | Asp | Thr |   |
|   | 405 |   |   |   |   | 410 |   |   |   |   | 415 |   |   |   |   |   |

| gcc | caa | agc | ctc | ctc | ata | gcc | tcg | tgg | aca | cct | gtg | tca | ccc | cca | tct | 1413 |
|---|---|---|---|---|---|---|---|---|---|---|---|---|---|---|---|---|
| Ala | Gln | Ser | Leu | Leu | Ile | Ala | Ser | Trp | Thr | Pro | Val | Ser | Pro | Pro | Ser |   |
| 420 |   |   |   |   | 425 |   |   |   |   | 430 |   |   |   |   | 435 |   |

| atg | tga | attgaacttt | cctccatgtg | ctgagacttg | taacaaccgg | tgtcaactgg | 1469 |
|---|---|---|---|---|---|---|---|
| Met |   |   |   |   |   |   |   |

| atcttctagg ctcaaagtgg caggctcttg ggacaaggga aaataaata aataaaagct | 1529 |
|---|---|
| agatactaac aactccattt tcaaataaga gcaataatac atgtcctata atcatgttct | 1589 |
| acagcctctt gtttgatacc tacagtagtg atatgtgtcc tacattatga agccaaggac | 1649 |
| agagagacgg ctgtggtcca gttttttgtg actggcagtt aatcagagtc ctttgctagg | 1709 |
| tagggtccta tatcttgtgt ttctctacaa catatatgtg actttgaaat cctggaattc | 1769 |
| gtccaccccc tgtcctactt tagtgagaca caaggtacac ctctaatgtc ctcccttgtt | 1829 |
| gccttagagt agttaacttt gaggacagaa aaaagcatag ccagaagatt gtaactgaac | 1889 |
| cgtcaactgt tctgcccttg aacatgcct actttaagca cacgtagctt tttgtgttgg | 1949 |
| gaagtcaact gtatggatac ttttctgttg acaaagtagc caaagacaat ctgcagaaag | 2009 |
| tgttttctgc acaataaagg caatatatag cacctgg | 2046 |

<210> SEQ ID NO 4
<211> LENGTH: 436
<212> TYPE: PRT
<213> ORGANISM: Mus musculus

```
<400> SEQUENCE: 4

Met Ser Ser Pro Gly Thr Glu Ser Ala Gly Lys Ser Leu Gln Tyr Arg
1               5                   10                  15

Val Asp His Leu Leu Ser Ala Val Glu Ser Glu Leu Gln Ala Gly Ser
            20                  25                  30

Glu Lys Gly Asp Pro Thr Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Thr
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Asn
    210                 215                 220

Asp His Lys Asp Val Met Glu Glu Pro Gly Asp Cys Gln Gln Pro Gly
225                 230                 235                 240

Tyr Ser Gln Trp Gly Trp Leu Val Pro Gly Ala Gly Thr Leu Cys Pro
                245                 250                 255

Pro Ala Ser Ser His Pro Gln Phe Gly Gly Ser Leu Ser Leu Pro Ser
            260                 265                 270

Thr His Gly Cys Glu Arg Tyr Pro Ala Leu Arg Asn His Arg Ser Ser
        275                 280                 285

Pro Tyr Pro Ser Pro Tyr Ala His Arg Asn Ser Ser Pro Thr Tyr Ala
    290                 295                 300

Asp Asn Ser Ser Ala Cys Leu Ser Met Leu Gln Ser His Asp Asn Trp
305                 310                 315                 320

Ser Ser Leu Gly Val Pro Gly His Thr Ser Met Leu Pro Val Ser His
                325                 330                 335

Asn Ala Ser Pro Pro Thr Gly Ser Ser Gln Tyr Pro Ser Leu Trp Ser
            340                 345                 350

Val Ser Asn Gly Thr Ile Thr Pro Gly Ser Gln Thr Ala Gly Val Ser
        355                 360                 365

Asn Gly Leu Gly Ala Gln Phe Phe Arg Gly Ser Pro Ala His Tyr Thr
    370                 375                 380

Pro Leu Thr His Thr Val Ser Ala Ala Thr Ser Ser Ser Gly Ser
385                 390                 395                 400

Pro Met Tyr Glu Gly Ala Ala Thr Val Thr Asp Ile Ser Asp Ser Gln
                405                 410                 415
```

```
        Tyr Asp Thr Ala Gln Ser Leu Leu Ile Ala Ser Trp Thr Pro Val Ser
                    420                 425                 430

Pro Pro Ser Met
                    435

<210> SEQ ID NO 5
<211> LENGTH: 1305
<212> TYPE: DNA
<213> ORGANISM: Homo sapiens
<220> FEATURE:
<221> NAME/KEY: CDS
<222> LOCATION: (1)..(1305)

<400> SEQUENCE: 5 atg agc tcc cct ggc acc gag agc gcg gga aag agc ctg cag tac cga        48
Met Ser Ser Pro Gly Thr Glu Ser Ala Gly Lys Ser Leu Gln Tyr Arg
1               5                   10                  15 gtg gac cac ctg ctg agc gcc gtg gag aat gag ctg cag gcg ggc agc        96
Val Asp His Leu Leu Ser Ala Val Glu Asn Glu Leu Gln Ala Gly Ser
            20                  25                  30 gag aag ggc gac ccc aca gag cgc gaa ctg cgc gtg ggc ctg gag gag       144
Glu Lys Gly Asp Pro Thr Glu Arg Glu Leu Arg Val Gly Leu Glu Glu
        35                  40                  45 agc gag ctg tgg ctg cgc ttc aag gag ctc acc aat gag atg atc gtg       192
Ser Glu Leu Trp Leu Arg Phe Lys Glu Leu Thr Asn Glu Met Ile Val
    50                  55                  60 acc aag aac ggc agg agg atg ttt ccg gtg ctg aag gtg aac gtg tct       240
Thr Lys Asn Gly Arg Arg Met Phe Pro Val Leu Lys Val Asn Val Ser
65                  70                  75                  80 ggc ctg gac ccc aac gcc atg tac tcc ttc ctg ctg gac ttc gtg gcg       288
Gly Leu Asp Pro Asn Ala Met Tyr Ser Phe Leu Leu Asp Phe Val Ala
                85                  90                  95 gcg gac aac cac cgc tgg aag tac gtg aac ggg gaa tgg gtg ccg ggg       336
Ala Asp Asn His Arg Trp Lys Tyr Val Asn Gly Glu Trp Val Pro Gly
            100                 105                 110 ggc aag ccg gag ccg cag gcg ccc agc tgc gtc tac atc cac ccc gac       384
Gly Lys Pro Glu Pro Gln Ala Pro Ser Cys Val Tyr Ile His Pro Asp
        115                 120                 125 tcg ccc aac ttc ggg gcc cac tgg atg aag gct ccc gtc tcc ttc agc       432
Ser Pro Asn Phe Gly Ala His Trp Met Lys Ala Pro Val Ser Phe Ser
    130                 135                 140 aaa gtc aag ctc acc aac aag ctc aac gga ggg ggc cag atc atg ctg       480
Lys Val Lys Leu Thr Asn Lys Leu Asn Gly Gly Gly Gln Ile Met Leu
145                 150                 155                 160 aac tcc ttg cat aag tat gag cct cga atc cac ata gtg aga gtt ggg       528
Asn Ser Leu His Lys Tyr Glu Pro Arg Ile His Ile Val Arg Val Gly
                165                 170                 175 gat cca cag cgc atg atc acc agc cac tgc ttc cct gag acc cag ttc       576
Asp Pro Gln Arg Met Ile Thr Ser His Cys Phe Pro Glu Thr Gln Phe
            180                 185                 190 ata gcg gtg act gct tat cag aac gag gag atc aca gct ctt aaa att       624
Ile Ala Val Thr Ala Tyr Gln Asn Glu Glu Ile Thr Ala Leu Lys Ile
        195                 200                 205 aag tac aat cca ttt gca aaa gct ttc ctt gat gca aag gaa aga agt       672
Lys Tyr Asn Pro Phe Ala Lys Ala Phe Leu Asp Ala Lys Glu Arg Ser
    210                 215                 220 gat cac aaa gag atg atg gag gaa ccc gga gac agc cag caa cct ggg       720
Asp His Lys Glu Met Met Glu Glu Pro Gly Asp Ser Gln Gln Pro Gly
225                 230                 235                 240 tac tcc caa tgg ggg tgg ctt ctt cct gga acc agc acc ctg tgt cca       768
```

```
                Tyr Ser Gln Trp Gly Trp Leu Leu Pro Gly Thr Ser Thr Leu Cys Pro
                                    245                 250                 255 cct gca aat cct cat cct cag ttt gga ggt gcc ctc tcc ctc ccc tcc         816
Pro Ala Asn Pro His Pro Gln Phe Gly Gly Ala Leu Ser Leu Pro Ser
        260                 265                 270 acg cac agc tgt gac agg tac cca acc ctg agg agc cac cgg tcc tca         864
Thr His Ser Cys Asp Arg Tyr Pro Thr Leu Arg Ser His Arg Ser Ser
            275                 280                 285 ccc tac ccc agc ccc tat gct cat cgg aac aat tct cca acc tat tct         912
Pro Tyr Pro Ser Pro Tyr Ala His Arg Asn Asn Ser Pro Thr Tyr Ser
        290                 295                 300 gac aac tca cct gca tgt tta tcc atg ctg caa tcc cat gac aat tgg         960
Asp Asn Ser Pro Ala Cys Leu Ser Met Leu Gln Ser His Asp Asn Trp
305                 310                 315                 320 tcc agc ctt gga atg cct gcc cat ccc agc atg ctc ccc gtg agc cac        1008
Ser Ser Leu Gly Met Pro Ala His Pro Ser Met Leu Pro Val Ser His
                325                 330                 335 aat gcc agc cca cct acc agc tcc agt cag tac ccc agc ctg tgg tct        1056
Asn Ala Ser Pro Pro Thr Ser Ser Ser Gln Tyr Pro Ser Leu Trp Ser
            340                 345                 350 gtg agc aac ggc gcc gtc acc ccg ggc tcc cag gca gca gcc gtg acc        1104
Val Ser Asn Gly Ala Val Thr Pro Gly Ser Gln Ala Ala Ala Val Thr
        355                 360                 365 aac ggg ctg ggg gcc cag ttc ttc cgg ggc tcc ccc gcg cac tac aca        1152
Asn Gly Leu Gly Ala Gln Phe Phe Arg Gly Ser Pro Ala His Tyr Thr
    370                 375                 380 ccc ctc acc cat ccg gtc tcg gca ccc tct tcc tcg gga tcc cca ctg        1200
Pro Leu Thr His Pro Val Ser Ala Pro Ser Ser Ser Gly Ser Pro Leu
385                 390                 395                 400 tac gaa ggg gcg gcc gcg gcc aca aac atc gtg gac agc cag tac gac        1248
Tyr Glu Gly Ala Ala Ala Ala Thr Asn Ile Val Asp Ser Gln Tyr Asp
                405                 410                 415 gcc gca gcc caa ggc cgc ctc ata gcc tca tgg aca cct gtg tcg cca        1296
Ala Ala Ala Gln Gly Arg Leu Ile Ala Ser Trp Thr Pro Val Ser Pro
            420                 425                 430 cct tcc atg                                                            1305
Pro Ser Met
        435

<210> SEQ ID NO 6
<211> LENGTH: 435
<212> TYPE: PRT
<213> ORGANISM: Homo sapiens

<400> SEQUENCE: 6

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
                20                  25                  30

Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
        50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110
```

```
Gly Lys Pro Glu Pro Gln Ala Pro Ser Cys Val Tyr Ile His Pro Asp
        115                 120                 125
Ser Pro Asn Phe Gly Ala His Trp Met Lys Ala Pro Val Ser Phe Ser
    130                 135                 140
Lys Val Lys Leu Thr Asn Lys Leu Asn Gly Gly Gln Ile Met Leu
145                 150                 155                 160
Asn Ser Leu His Lys Tyr Glu Pro Arg Ile His Ile Val Arg Val Gly
                165                 170                 175
Asp Pro Gln Arg Met Ile Thr Ser His Cys Phe Pro Glu Thr Gln Phe
            180                 185                 190
Ile Ala Val Thr Ala Tyr Gln Asn Glu Glu Ile Thr Ala Leu Lys Ile
        195                 200                 205
Lys Tyr Asn Pro Phe Ala Lys Ala Phe Leu Asp Ala Lys Glu Arg Ser
    210                 215                 220
Asp His Lys Glu Met Met Glu Glu Pro Gly Asp Ser Gln Gln Pro Gly
225                 230                 235                 240
Tyr Ser Gln Trp Gly Trp Leu Leu Pro Gly Thr Ser Thr Leu Cys Pro
                245                 250                 255
Pro Ala Asn Pro His Pro Gln Phe Gly Gly Ala Leu Ser Leu Pro Ser
            260                 265                 270
Thr His Ser Cys Asp Arg Tyr Pro Thr Leu Arg Ser His Arg Ser Ser
        275                 280                 285
Pro Tyr Pro Ser Pro Tyr Ala His Arg Asn Asn Ser Pro Thr Tyr Ser
    290                 295                 300
Asp Asn Ser Pro Ala Cys Leu Ser Met Leu Gln Ser His Asp Asn Trp
305                 310                 315                 320
Ser Ser Leu Gly Met Pro Ala His Pro Ser Met Leu Pro Val Ser His
                325                 330                 335
Asn Ala Ser Pro Pro Thr Ser Ser Gln Tyr Pro Ser Leu Trp Ser
            340                 345                 350
Val Ser Asn Gly Ala Val Thr Pro Gly Ser Gln Ala Ala Val Thr
        355                 360                 365
Asn Gly Leu Gly Ala Gln Phe Phe Arg Gly Ser Pro Ala His Tyr Thr
    370                 375                 380
Pro Leu Thr His Pro Val Ser Ala Pro Ser Ser Ser Gly Ser Pro Leu
385                 390                 395                 400
Tyr Glu Gly Ala Ala Ala Ala Thr Asn Ile Val Asp Ser Gln Tyr Asp
                405                 410                 415
Ala Ala Ala Gln Gly Arg Leu Ile Ala Ser Trp Thr Pro Val Ser Pro
            420                 425                 430
Pro Ser Met
        435

<210> SEQ ID NO 7
<211> LENGTH: 1357
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1347)

<400> SEQUENCE: 7 gaattccgc atg gcc gat gaa gct ccg agc tcc cct ggc acc gag agc gcg    51
          Met Ala Asp Glu Ala Pro Ser Ser Pro Gly Thr Glu Ser Ala
```

| | | | | | | | | | | | | | | | |
|---|---|---|---|---|---|---|---|---|---|---|---|---|---|---|---|
| | 1 | | | | 5 | | | | | 10 | | | | | |
| gga | aag | agc | ctg | cag | tac | cga | gtg | gac | cac | ctg | ctg | agc | gcc | gtg | gag | 99 |
| Gly | Lys | Ser | Leu | Gln | Tyr | Arg | Val | Asp | His | Leu | Leu | Ser | Ala | Val | Glu | |
| 15 | | | | 20 | | | | | 25 | | | | | 30 | | |

| aat | gag | ctg | cag | gcg | ggc | agc | gag | aag | ggc | gac | ccc | aca | gag | cgc | gaa | 147 |
|---|---|---|---|---|---|---|---|---|---|---|---|---|---|---|---|---|
| Asn | Glu | Leu | Gln | Ala | Gly | Ser | Glu | Lys | Gly | Asp | Pro | Thr | Glu | Arg | Glu | |
| | | | | 35 | | | | 40 | | | | | 45 | | | |

| ctg | cgc | gtg | ggc | ctg | gag | gag | agc | gag | ctg | tgg | ctg | cgc | ttc | aag | gag | 195 |
|---|---|---|---|---|---|---|---|---|---|---|---|---|---|---|---|---|
| Leu | Arg | Val | Gly | Leu | Glu | Glu | Ser | Glu | Leu | Trp | Leu | Arg | Phe | Lys | Glu | |
| | | 50 | | | | | 55 | | | | | 60 | | | | |

| ctc | acc | aat | gag | atg | atc | gtg | acc | aag | aac | ggc | agg | agg | atg | ttt | ccg | 243 |
|---|---|---|---|---|---|---|---|---|---|---|---|---|---|---|---|---|
| Leu | Thr | Asn | Glu | Met | Ile | Val | Thr | Lys | Asn | Gly | Arg | Arg | Met | Phe | Pro | |
| | | 65 | | | | 70 | | | | | 75 | | | | | |

| gtg | ctg | aag | gtg | aac | gtg | tct | ggc | ctg | gac | ccc | aac | gcc | atg | tac | tcc | 291 |
|---|---|---|---|---|---|---|---|---|---|---|---|---|---|---|---|---|
| Val | Leu | Lys | Val | Asn | Val | Ser | Gly | Leu | Asp | Pro | Asn | Ala | Met | Tyr | Ser | |
| 80 | | | | | 85 | | | | | 90 | | | | | | |

| ttc | ctg | ctg | gac | ttc | gtg | gcg | gcg | gac | aac | cac | cgc | tgg | aag | tac | gtg | 339 |
|---|---|---|---|---|---|---|---|---|---|---|---|---|---|---|---|---|
| Phe | Leu | Leu | Asp | Phe | Val | Ala | Ala | Asp | Asn | His | Arg | Trp | Lys | Tyr | Val | |
| 95 | | | | | 100 | | | | | 105 | | | | | 110 | |

| aac | ggg | gaa | tgg | gtg | ccg | ggg | ggc | aag | ccg | gag | ccg | cag | gcg | ccc | agc | 387 |
|---|---|---|---|---|---|---|---|---|---|---|---|---|---|---|---|---|
| Asn | Gly | Glu | Trp | Val | Pro | Gly | Gly | Lys | Pro | Glu | Pro | Gln | Ala | Pro | Ser | |
| | | | | 115 | | | | | 120 | | | | | 125 | | |

| tgc | gtc | tac | atc | cac | ccc | gac | tcg | ccc | aac | ttc | ggg | gcc | cac | tgg | atg | 435 |
|---|---|---|---|---|---|---|---|---|---|---|---|---|---|---|---|---|
| Cys | Val | Tyr | Ile | His | Pro | Asp | Ser | Pro | Asn | Phe | Gly | Ala | His | Trp | Met | |
| | | | 130 | | | | | 135 | | | | | 140 | | | |

| aag | gct | ccc | gtc | tcc | ttc | agc | aaa | gtc | aag | ctc | acc | aac | aag | ctc | aac | 483 |
|---|---|---|---|---|---|---|---|---|---|---|---|---|---|---|---|---|
| Lys | Ala | Pro | Val | Ser | Phe | Ser | Lys | Val | Lys | Leu | Thr | Asn | Lys | Leu | Asn | |
| | | 145 | | | | | 150 | | | | | 155 | | | | |

| gga | ggg | ggc | cag | atc | atg | ctg | aac | tcc | ttg | cat | aag | tat | gag | cct | cga | 531 |
|---|---|---|---|---|---|---|---|---|---|---|---|---|---|---|---|---|
| Gly | Gly | Gly | Gln | Ile | Met | Leu | Asn | Ser | Leu | His | Lys | Tyr | Glu | Pro | Arg | |
| | 160 | | | | | 165 | | | | | 170 | | | | | |

| atc | cac | ata | gtg | aga | gtt | ggg | gat | cca | cag | cgc | atg | atc | acc | agc | cac | 579 |
|---|---|---|---|---|---|---|---|---|---|---|---|---|---|---|---|---|
| Ile | His | Ile | Val | Arg | Val | Gly | Asp | Pro | Gln | Arg | Met | Ile | Thr | Ser | His | |
| 175 | | | | | 180 | | | | | 185 | | | | | 190 | |

| tgc | ttc | cct | gag | acc | cag | ttc | ata | gcg | gtg | act | gct | tat | cag | aac | gag | 627 |
|---|---|---|---|---|---|---|---|---|---|---|---|---|---|---|---|---|
| Cys | Phe | Pro | Glu | Thr | Gln | Phe | Ile | Ala | Val | Thr | Ala | Tyr | Gln | Asn | Glu | |
| | | | | 195 | | | | | 200 | | | | | 205 | | |

| gag | atc | aca | gct | ctt | aaa | att | aag | tac | aat | cca | ttt | gca | aaa | gct | ttc | 675 |
|---|---|---|---|---|---|---|---|---|---|---|---|---|---|---|---|---|
| Glu | Ile | Thr | Ala | Leu | Lys | Ile | Lys | Tyr | Asn | Pro | Phe | Ala | Lys | Ala | Phe | |
| | | | 210 | | | | | 215 | | | | | 220 | | | |

| ctt | gat | gca | aag | gaa | aga | agt | gat | cac | aaa | gag | atg | atg | gag | gaa | ccc | 723 |
|---|---|---|---|---|---|---|---|---|---|---|---|---|---|---|---|---|
| Leu | Asp | Ala | Lys | Glu | Arg | Ser | Asp | His | Lys | Glu | Met | Met | Glu | Glu | Pro | |
| | | 225 | | | | | 230 | | | | | 235 | | | | |

| gga | gac | agc | cag | caa | cct | ggg | tac | tcc | caa | tgg | ggg | tgg | ctt | ctt | cct | 771 |
|---|---|---|---|---|---|---|---|---|---|---|---|---|---|---|---|---|
| Gly | Asp | Ser | Gln | Gln | Pro | Gly | Tyr | Ser | Gln | Trp | Gly | Trp | Leu | Leu | Pro | |
| | 240 | | | | | 245 | | | | | 250 | | | | | |

| gga | acc | agc | acc | ctg | tgt | cca | cct | gca | aat | cct | cat | cct | cag | ttt | gga | 819 |
|---|---|---|---|---|---|---|---|---|---|---|---|---|---|---|---|---|
| Gly | Thr | Ser | Thr | Leu | Cys | Pro | Pro | Ala | Asn | Pro | His | Pro | Gln | Phe | Gly | |
| 255 | | | | | 260 | | | | | 265 | | | | | 270 | |

| ggt | gcc | ctc | tcc | ctc | ccc | tcc | acg | cac | agc | tgt | gac | agg | tac | cca | acc | 867 |
|---|---|---|---|---|---|---|---|---|---|---|---|---|---|---|---|---|
| Gly | Ala | Leu | Ser | Leu | Pro | Ser | Thr | His | Ser | Cys | Asp | Arg | Tyr | Pro | Thr | |
| | | | 275 | | | | | 280 | | | | | 285 | | | |

| ctg | agg | agc | cac | cgg | tcc | tca | ccc | tac | ccc | agc | cct | tat | gct | cat | cgg | 915 |
|---|---|---|---|---|---|---|---|---|---|---|---|---|---|---|---|---|
| Leu | Arg | Ser | His | Arg | Ser | Ser | Pro | Tyr | Pro | Ser | Pro | Tyr | Ala | His | Arg | |
| | | 290 | | | | | 295 | | | | | 300 | | | | |

| aac | aat | tct | cca | acc | tat | tct | gac | aac | tca | cct | gca | tgt | tta | tcc | atg | 963 |
|---|---|---|---|---|---|---|---|---|---|---|---|---|---|---|---|---|
| Asn | Asn | Ser | Pro | Thr | Tyr | Ser | Asp | Asn | Ser | Pro | Ala | Cys | Leu | Ser | Met | |
| | 305 | | | | | 310 | | | | | 315 | | | | | |

| ctg | caa | tcc | cat | gac | aat | tgg | tcc | agc | ctt | gga | atg | cct | gcc | cat | ccc | 1011 |

```
Leu Gln Ser His Asp Asn Trp Ser Ser Leu Gly Met Pro Ala His Pro
    320                 325                 330 agc atg ctc ccc gtg agc cac aat gcc agc cca cct acc agc tcc agt    1059
Ser Met Leu Pro Val Ser His Asn Ala Ser Pro Pro Thr Ser Ser Ser
335                 340                 345                 350 cag tac ccc agc ctg tgg tct gtg agc aac ggc gcc gtc acc ccg ggc    1107
Gln Tyr Pro Ser Leu Trp Ser Val Ser Asn Gly Ala Val Thr Pro Gly
                355                 360                 365 tcc cag gca gca gcc gtg acc aac ggg ctg ggg gcc cag ttc ttc cgg    1155
Ser Gln Ala Ala Ala Val Thr Asn Gly Leu Gly Ala Gln Phe Phe Arg
            370                 375                 380 ggc tcc ccc gcg cac tac aca ccc ctc acc cat ccg gtc tcg gca ccc    1203
Gly Ser Pro Ala His Tyr Thr Pro Leu Thr His Pro Val Ser Ala Pro
        385                 390                 395 tct tcc tcg gga tcc cca ctg tac gaa ggg gcg gcc gcg gcc aca aac    1251
Ser Ser Ser Gly Ser Pro Leu Tyr Glu Gly Ala Ala Ala Ala Thr Asn
    400                 405                 410 atc gtg gac agc cag tac gac gcc gca gcc caa ggc cgc ctc ata gcc    1299
Ile Val Asp Ser Gln Tyr Asp Ala Ala Ala Gln Gly Arg Leu Ile Ala
415                 420                 425                 430 tca tgg aca cct gtg tcg cca cct tcc atg cat cac cat cac cat cac    1347
Ser Trp Thr Pro Val Ser Pro Pro Ser Met His His His His His His
                435                 440                 445 tgagactagt                                                         1357

<210> SEQ ID NO 8
<211> LENGTH: 446
<212> TYPE: PRT
<213> ORGANISM: Artificial
<220> FEATURE:
<223> OTHER INFORMATION: Synthetic Construct

<400> SEQUENCE: 8

Met Ala Asp Glu Ala Pro Ser Ser Pro Gly Thr Glu Ser Ala Gly Lys
1               5                   10                  15

Ser Leu Gln Tyr Arg Val Asp His Leu Leu Ser Ala Val Glu Asn Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

Tyr Ile His Pro Asp Ser Pro Asn Phe Gly Ala His Trp Met Lys Ala
    130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Asp Pro Gln Arg Met Ile Thr Ser His Cys Phe
            180                 185                 190
```

```
Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
    210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Leu Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
        275                 280                 285

Ser His Arg Ser Ser Pro Tyr Pro Ser Pro Tyr Ala His Arg Asn Asn
    290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
        355                 360                 365

Ala Ala Ala Val Thr Asn Gly Leu Gly Ala Gln Phe Phe Arg Gly Ser
    370                 375                 380

Pro Ala His Tyr Thr Pro Leu Thr His Pro Val Ser Ala Pro Ser Ser
385                 390                 395                 400

Ser Gly Ser Pro Leu Tyr Glu Gly Ala Ala Ala Thr Asn Ile Val
                405                 410                 415

Asp Ser Gln Tyr Asp Ala Ala Ala Gln Gly Arg Leu Ile Ala Ser Trp
            420                 425                 430

Thr Pro Val Ser Pro Pro Ser Met His His His His His
        435                 440                 445

<210> SEQ ID NO 9
<211> LENGTH: 1360
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1353)

<400> SEQUENCE: 9 gaattccgc atg gcc gat gaa gct ccg agc tcg ccg ggc aca gag agc gca      51
          Met Ala Asp Glu Ala Pro Ser Ser Pro Gly Thr Glu Ser Ala
              1               5                   10 ggg aag agc ctg cag tac cga gtg gac cac ctg ctc agc gcc gtg gag       99
Gly Lys Ser Leu Gln Tyr Arg Val Asp His Leu Leu Ser Ala Val Glu
15                  20                  25                  30 agc gag ctg cag gcg ggc agc gag aag gga gac ccc acc gaa cgc gaa      147
Ser Glu Leu Gln Ala Gly Ser Glu Lys Gly Asp Pro Thr Glu Arg Glu
                35                  40                  45 ctg cga gtg ggc ctg gag gag agc gag ctg tgg ctg cgc ttc aag gag      195
Leu Arg Val Gly Leu Glu Glu Ser Glu Leu Trp Leu Arg Phe Lys Glu
            50                  55                  60 cta act aac gag atg att gtg acc aag aac ggc agg agg atg ttc ccg      243
Leu Thr Asn Glu Met Ile Val Thr Lys Asn Gly Arg Arg Met Phe Pro
```

-continued

| | | | | | | | | | | | | | | | | |
|---|---|---|---|---|---|---|---|---|---|---|---|---|---|---|---|---|
| | | 65 | | | | | 70 | | | | | 75 | | | | |
| gtg | ctg | aag | gta | aat | gtg | tca | ggc | ctg | gac | ccc | aat | gcc | atg | tac | tct | 291 |
| Val | Leu | Lys | Val | Asn | Val | Ser | Gly | Leu | Asp | Pro | Asn | Ala | Met | Tyr | Ser | |
| | 80 | | | | | 85 | | | | | 90 | | | | | |
| ttc | ttg | ctg | gac | ttc | gtg | acg | gct | gac | aac | cac | cgc | tgg | aaa | tat | gtg | 339 |
| Phe | Leu | Leu | Asp | Phe | Val | Thr | Ala | Asp | Asn | His | Arg | Trp | Lys | Tyr | Val | |
| 95 | | | | | 100 | | | | | 105 | | | | | 110 | |
| aac | ggg | gag | tgg | gta | cct | ggg | ggc | aaa | cca | gag | cct | cag | gcg | ccc | agc | 387 |
| Asn | Gly | Glu | Trp | Val | Pro | Gly | Gly | Lys | Pro | Glu | Pro | Gln | Ala | Pro | Ser | |
| | | | | 115 | | | | | 120 | | | | | 125 | | |
| tgc | gtc | tac | atc | cac | cca | gac | tcg | ccc | aat | ttt | ggg | gcc | cac | tgg | atg | 435 |
| Cys | Val | Tyr | Ile | His | Pro | Asp | Ser | Pro | Asn | Phe | Gly | Ala | His | Trp | Met | |
| | | | 130 | | | | | 135 | | | | | 140 | | | |
| aag | gcg | cct | gtg | tct | ttc | agc | aaa | gtc | aaa | ctc | acc | aac | aag | ctc | aat | 483 |
| Lys | Ala | Pro | Val | Ser | Phe | Ser | Lys | Val | Lys | Leu | Thr | Asn | Lys | Leu | Asn | |
| | | 145 | | | | | 150 | | | | | 155 | | | | |
| gga | gga | gga | cag | atc | atg | tta | aac | tcc | ttg | cat | aag | tat | gaa | cct | cgg | 531 |
| Gly | Gly | Gly | Gln | Ile | Met | Leu | Asn | Ser | Leu | His | Lys | Tyr | Glu | Pro | Arg | |
| | 160 | | | | | 165 | | | | | 170 | | | | | |
| att | cac | atc | gtg | aga | gtt | ggg | ggc | ccg | caa | cgc | atg | atc | acc | agc | cac | 579 |
| Ile | His | Ile | Val | Arg | Val | Gly | Gly | Pro | Gln | Arg | Met | Ile | Thr | Ser | His | |
| 175 | | | | | 180 | | | | | 185 | | | | | 190 | |
| tgc | ttt | ccc | gag | acc | cag | ttc | ata | gct | gtg | act | gcc | tac | cag | aat | gag | 627 |
| Cys | Phe | Pro | Glu | Thr | Gln | Phe | Ile | Ala | Val | Thr | Ala | Tyr | Gln | Asn | Glu | |
| | | | | 195 | | | | | 200 | | | | | 205 | | |
| gag | att | aca | gcc | ctt | aaa | att | aaa | tac | aac | cca | ttt | gct | aaa | gcc | ttc | 675 |
| Glu | Ile | Thr | Ala | Leu | Lys | Ile | Lys | Tyr | Asn | Pro | Phe | Ala | Lys | Ala | Phe | |
| | | | 210 | | | | | 215 | | | | | 220 | | | |
| ctt | gat | gcc | aaa | gaa | aga | aac | gac | cac | aaa | gat | gta | atg | gag | gaa | ccg | 723 |
| Leu | Asp | Ala | Lys | Glu | Arg | Asn | Asp | His | Lys | Asp | Val | Met | Glu | Glu | Pro | |
| | | 225 | | | | | 230 | | | | | 235 | | | | |
| ggg | gac | tgc | cag | cag | ccg | ggg | tat | tcc | caa | tgg | ggg | tgg | ctt | gtt | cct | 771 |
| Gly | Asp | Cys | Gln | Gln | Pro | Gly | Tyr | Ser | Gln | Trp | Gly | Trp | Leu | Val | Pro | |
| | 240 | | | | | 245 | | | | | 250 | | | | | |
| ggt | gct | ggc | acc | ctc | tgc | ccg | cct | gcc | agc | tcc | cac | cct | cag | ttt | gga | 819 |
| Gly | Ala | Gly | Thr | Leu | Cys | Pro | Pro | Ala | Ser | Ser | His | Pro | Gln | Phe | Gly | |
| 255 | | | | | 260 | | | | | 265 | | | | | 270 | |
| ggc | tcg | ctc | tct | ctc | ccc | tcc | aca | cac | ggc | tgt | gag | agg | tac | cca | gct | 867 |
| Gly | Ser | Leu | Ser | Leu | Pro | Ser | Thr | His | Gly | Cys | Glu | Arg | Tyr | Pro | Ala | |
| | | | | 275 | | | | | 280 | | | | | 285 | | |
| cta | agg | aac | cac | cgg | tca | tcg | ccc | tac | ccc | agc | ccc | tat | gct | cat | cgg | 915 |
| Leu | Arg | Asn | His | Arg | Ser | Ser | Pro | Tyr | Pro | Ser | Pro | Tyr | Ala | His | Arg | |
| | | | 290 | | | | | 295 | | | | | 300 | | | |
| aac | agc | tct | cca | acc | tac | gcg | gac | aat | tca | tct | gct | tgt | ctg | tcc | atg | 963 |
| Asn | Ser | Ser | Pro | Thr | Tyr | Ala | Asp | Asn | Ser | Ser | Ala | Cys | Leu | Ser | Met | |
| | | 305 | | | | | 310 | | | | | 315 | | | | |
| ctg | cag | tcc | cat | gat | aac | tgg | tct | agc | ctc | gga | gtg | cct | ggc | cac | acc | 1011 |
| Leu | Gln | Ser | His | Asp | Asn | Trp | Ser | Ser | Leu | Gly | Val | Pro | Gly | His | Thr | |
| | 320 | | | | | 325 | | | | | 330 | | | | | |
| agc | atg | ctg | cct | gtg | agt | cat | aac | gcc | agc | cca | cct | act | ggc | tct | agc | 1059 |
| Ser | Met | Leu | Pro | Val | Ser | His | Asn | Ala | Ser | Pro | Pro | Thr | Gly | Ser | Ser | |
| 335 | | | | | 340 | | | | | 345 | | | | | 350 | |
| cag | tat | ccc | agt | ctc | tgg | tct | gtg | agc | aat | ggt | acc | atc | acc | cca | ggc | 1107 |
| Gln | Tyr | Pro | Ser | Leu | Trp | Ser | Val | Ser | Asn | Gly | Thr | Ile | Thr | Pro | Gly | |
| | | | | 355 | | | | | 360 | | | | | 365 | | |
| tcc | cag | aca | gct | ggg | gtg | tcc | aac | ggg | ctg | gga | gct | cag | ttc | ttt | cga | 1155 |
| Ser | Gln | Thr | Ala | Gly | Val | Ser | Asn | Gly | Leu | Gly | Ala | Gln | Phe | Phe | Arg | |
| | | | 370 | | | | | 375 | | | | | 380 | | | |
| ggc | tcc | cct | gca | cat | tac | aca | cca | ctg | aca | cac | acg | gtc | tca | gct | gcc | 1203 |

```
Gly Ser Pro Ala His Tyr Thr Pro Leu Thr His Thr Val Ser Ala Ala
            385                 390                 395 acg tcc tcg tct tct ggt tct ccg atg tat gaa ggg gct gct aca gtc    1251
Thr Ser Ser Ser Ser Gly Ser Pro Met Tyr Glu Gly Ala Ala Thr Val
400                 405                 410 aca gac att tct gac agc cag tat gac acg gcc caa agc ctc ctc ata    1299
Thr Asp Ile Ser Asp Ser Gln Tyr Asp Thr Ala Gln Ser Leu Leu Ile
415                 420                 425                 430 gcc tcg tgg aca cct gtg tca ccc cca tct atg cat cac cat cac cat    1347
Ala Ser Trp Thr Pro Val Ser Pro Pro Ser Met His His His His His
                435                 440                 445 cac tga gactagt                                                    1360
His
```

<210> SEQ ID NO 10
<211> LENGTH: 447
<212> TYPE: PRT
<213> ORGANISM: Artificial
<220> FEATURE:
<223> OTHER INFORMATION: Synthetic Construct

<400> SEQUENCE: 10

```
Met Ala Asp Glu Ala Pro Ser Ser Pro Gly Thr Glu Ser Ala Gly Lys
1               5                   10                  15

Ser Leu Gln Tyr Arg Val Asp His Leu Leu Ser Ala Val Glu Ser Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Thr Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

Tyr Ile His Pro Asp Ser Pro Asn Phe Gly Ala His Trp Met Lys Ala
130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Gly Pro Gln Arg Met Ile Thr Ser His Cys Phe
            180                 185                 190

Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
210                 215                 220

Ala Lys Glu Arg Asn Asp His Lys Asp Val Met Glu Glu Pro Gly Asp
225                 230                 235                 240

Cys Gln Gln Pro Gly Tyr Ser Gln Trp Gly Trp Leu Val Pro Gly Ala
                245                 250                 255

Gly Thr Leu Cys Pro Pro Ala Ser Ser His Pro Gln Phe Gly Gly Ser
            260                 265                 270
```

```
Leu Ser Leu Pro Ser Thr His Gly Cys Glu Arg Tyr Pro Ala Leu Arg
            275                 280                 285

Asn His Arg Ser Ser Pro Tyr Pro Ser Pro Tyr Ala His Arg Asn Ser
    290                 295                 300

Ser Pro Thr Tyr Ala Asp Asn Ser Ser Ala Cys Leu Ser Met Leu Gln
305                 310                 315                 320

Ser His Asp Asn Trp Ser Ser Leu Gly Val Pro Gly His Thr Ser Met
                325                 330                 335

Leu Pro Val Ser His Asn Ala Ser Pro Pro Thr Gly Ser Ser Gln Tyr
            340                 345                 350

Pro Ser Leu Trp Ser Val Ser Asn Gly Thr Ile Thr Pro Gly Ser Gln
            355                 360                 365

Thr Ala Gly Val Ser Asn Gly Leu Gly Ala Gln Phe Phe Arg Gly Ser
            370                 375                 380

Pro Ala His Tyr Thr Pro Leu Thr His Thr Val Ser Ala Ala Thr Ser
385                 390                 395                 400

Ser Ser Ser Gly Ser Pro Met Tyr Glu Gly Ala Ala Thr Val Thr Asp
                405                 410                 415

Ile Ser Asp Ser Gln Tyr Asp Thr Ala Gln Ser Leu Leu Ile Ala Ser
                420                 425                 430

Trp Thr Pro Val Ser Pro Pro Ser Met His His His His His His
            435                 440                 445

<210> SEQ ID NO 11
<211> LENGTH: 6
<212> TYPE: PRT
<213> ORGANISM: Artificial
<220> FEATURE:
<223> OTHER INFORMATION: Synthetic Peptide

<400> SEQUENCE: 11

Met Ala Asp Glu Ala Pro
1               5

<210> SEQ ID NO 12
<211> LENGTH: 9
<212> TYPE: PRT
<213> ORGANISM: Homo sapiens

<400> SEQUENCE: 12

Trp Leu Leu Pro Gly Thr Ser Thr Leu
1               5

<210> SEQ ID NO 13
<211> LENGTH: 9
<212> TYPE: PRT
<213> ORGANISM: Homo sapiens

<400> SEQUENCE: 13

Trp Leu Leu Pro Gly Thr Ser Thr Val
1               5

<210> SEQ ID NO 14
<211> LENGTH: 9
<212> TYPE: PRT
<213> ORGANISM: Homo sapiens

<400> SEQUENCE: 14

Ser Gln Tyr Pro Ser Leu Trp Ser Val
1               5
```

<210> SEQ ID NO 15
<211> LENGTH: 9
<212> TYPE: PRT
<213> ORGANISM: Homo sapiens

<400> SEQUENCE: 15

Arg Leu Ile Ala Ser Trp Thr Pro Val
1               5

<210> SEQ ID NO 16
<211> LENGTH: 10
<212> TYPE: PRT
<213> ORGANISM: Homo sapiens

<400> SEQUENCE: 16

Ala Met Tyr Ser Phe Leu Leu Asp Phe Val
1               5                   10

<210> SEQ ID NO 17
<211> LENGTH: 1305
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1305)

<400> SEQUENCE: 17

```
atg agc tcc cct ggc acc gag agc gcg gga aag agc ctg cag tac cga      48
Met Ser Ser Pro Gly Thr Glu Ser Ala Gly Lys Ser Leu Gln Tyr Arg
1               5                   10                  15 gtg gac cac ctg ctg agc gcc gtg gag aat gag ctg cag gcg ggc agc      96
Val Asp His Leu Leu Ser Ala Val Glu Asn Glu Leu Gln Ala Gly Ser
            20                  25                  30 gag aag ggc gac ccc aca gag cgc gaa ctg cgc gtg ggc ctg gag gag     144
Glu Lys Gly Asp Pro Thr Glu Arg Glu Leu Arg Val Gly Leu Glu Glu
        35                  40                  45 agc gag ctg tgg ctg cgc ttc aag gag ctc acc aat gag atg atc gtg     192
Ser Glu Leu Trp Leu Arg Phe Lys Glu Leu Thr Asn Glu Met Ile Val
    50                  55                  60 acc aag aac ggc agg agg atg ttt ccg gtg ctg aag gtg aac gtg tct     240
Thr Lys Asn Gly Arg Arg Met Phe Pro Val Leu Lys Val Asn Val Ser
65                  70                  75                  80 ggc ctg gac ccc aac gcc atg tac tcc ttc ctg ctg gac ttc gtg gcg     288
Gly Leu Asp Pro Asn Ala Met Tyr Ser Phe Leu Leu Asp Phe Val Ala
                85                  90                  95 gcg gac aac cac cgc tgg aag tac gtg aac ggg gaa tgg gtg ccg ggg     336
Ala Asp Asn His Arg Trp Lys Tyr Val Asn Gly Glu Trp Val Pro Gly
            100                 105                 110 ggc aag ccg gag ccg cag gcg ccc agc tgc gtc tac atc cac ccc gac     384
Gly Lys Pro Glu Pro Gln Ala Pro Ser Cys Val Tyr Ile His Pro Asp
        115                 120                 125 tcg ccc aac ttc ggg gcc cac tgg atg aag gct ccc gtc tcc ttc agc     432
Ser Pro Asn Phe Gly Ala His Trp Met Lys Ala Pro Val Ser Phe Ser
    130                 135                 140 aaa gtc aag ctc acc aac aag ctc aac gga ggg ggc cag atc atg ctg     480
Lys Val Lys Leu Thr Asn Lys Leu Asn Gly Gly Gly Gln Ile Met Leu
145                 150                 155                 160 aac tcc ttg cat aag tat gag cct cga atc cac ata gtg aga gtt ggg     528
Asn Ser Leu His Lys Tyr Glu Pro Arg Ile His Ile Val Arg Val Gly
                165                 170                 175
```

```
gat cca cag cgc atg atc acc agc cac tgc ttc cct gag acc cag ttc      576
Asp Pro Gln Arg Met Ile Thr Ser His Cys Phe Pro Glu Thr Gln Phe
            180                 185                 190 ata gcg gtg act gct tat cag aac gag gag atc aca gct ctt aaa att      624
Ile Ala Val Thr Ala Tyr Gln Asn Glu Glu Ile Thr Ala Leu Lys Ile
        195                 200                 205 aag tac aat cca ttt gca aaa gct ttc ctt gat gca aag gaa aga agt      672
Lys Tyr Asn Pro Phe Ala Lys Ala Phe Leu Asp Ala Lys Glu Arg Ser
    210                 215                 220 gat cac aaa gag atg atg gag gaa ccc gga gac agc cag caa cct ggg      720
Asp His Lys Glu Met Met Glu Glu Pro Gly Asp Ser Gln Gln Pro Gly
225                 230                 235                 240 tac tcc caa tgg ggg tgg ctt ctt cct gga acc agc acc gtg tgt cca      768
Tyr Ser Gln Trp Gly Trp Leu Leu Pro Gly Thr Ser Thr Val Cys Pro
                245                 250                 255 cct gca aat cct cat cct cag ttt gga ggt gcc ctc tcc ctc ccc tcc      816
Pro Ala Asn Pro His Pro Gln Phe Gly Gly Ala Leu Ser Leu Pro Ser
            260                 265                 270 acg cac agc tgt gac agg tac cca acc ctg agg agc cac cgg tcc tca      864
Thr His Ser Cys Asp Arg Tyr Pro Thr Leu Arg Ser His Arg Ser Ser
        275                 280                 285 ccc tac ccc agc ccc tat gct cat cgg aac aat tct cca acc tat tct      912
Pro Tyr Pro Ser Pro Tyr Ala His Arg Asn Asn Ser Pro Thr Tyr Ser
    290                 295                 300 gac aac tca cct gca tgt tta tcc atg ctg caa tcc cat gac aat tgg      960
Asp Asn Ser Pro Ala Cys Leu Ser Met Leu Gln Ser His Asp Asn Trp
305                 310                 315                 320 tcc agc ctt gga atg cct gcc cat ccc agc atg ctc ccc gtg agc cac     1008
Ser Ser Leu Gly Met Pro Ala His Pro Ser Met Leu Pro Val Ser His
                325                 330                 335 aat gcc agc cca cct acc agc tcc agt cag tac ccc agc ctg tgg tct     1056
Asn Ala Ser Pro Pro Thr Ser Ser Ser Gln Tyr Pro Ser Leu Trp Ser
            340                 345                 350 gtg agc aac ggc gcc gtc acc ccg ggc tcc cag gca gca gcc gtg acc     1104
Val Ser Asn Gly Ala Val Thr Pro Gly Ser Gln Ala Ala Ala Val Thr
        355                 360                 365 aac ggg ctg ggg gcc cag ttc ttc cgg ggc tcc ccc gcg cac tac aca     1152
Asn Gly Leu Gly Ala Gln Phe Phe Arg Gly Ser Pro Ala His Tyr Thr
    370                 375                 380 ccc ctc acc cat ccg gtc tcg gca ccc tct tcc tcg gga tcc cca ctg     1200
Pro Leu Thr His Pro Val Ser Ala Pro Ser Ser Ser Gly Ser Pro Leu
385                 390                 395                 400 tac gaa ggg gcg gcc gcg gcc aca aac atc gtg gac agc cag tac gac     1248
Tyr Glu Gly Ala Ala Ala Ala Thr Asn Ile Val Asp Ser Gln Tyr Asp
                405                 410                 415 gcc gca gcc caa ggc cgc ctc ata gcc tca tgg aca cct gtg tcg cca     1296
Ala Ala Ala Gln Gly Arg Leu Ile Ala Ser Trp Thr Pro Val Ser Pro
            420                 425                 430 cct tcc atg                                                         1305
Pro Ser Met
        435

<210> SEQ ID NO 18
<211> LENGTH: 435
<212> TYPE: PRT
<213> ORGANISM: Artificial
<220> FEATURE:
<223> OTHER INFORMATION: Synthetic Construct

<400> SEQUENCE: 18

Met Ser Ser Pro Gly Thr Glu Ser Ala Gly Lys Ser Leu Gln Tyr Arg
```

-continued

```
1               5                   10                  15
Val Asp His Leu Leu Ser Ala Val Glu Asn Glu Leu Gln Ala Gly Ser
                20                  25                  30
Glu Lys Gly Asp Pro Thr Glu Arg Glu Leu Arg Val Gly Leu Glu Glu
                35                  40                  45
Ser Glu Leu Trp Leu Arg Phe Lys Glu Leu Thr Asn Glu Met Ile Val
                50                  55                  60
Thr Lys Asn Gly Arg Arg Met Phe Pro Val Leu Lys Val Asn Val Ser
65                      70                  75                  80
Gly Leu Asp Pro Asn Ala Met Tyr Ser Phe Leu Leu Asp Phe Val Ala
                        85                  90                  95
Ala Asp Asn His Arg Trp Lys Tyr Val Asn Gly Glu Trp Val Pro Gly
                100                 105                 110
Gly Lys Pro Glu Pro Gln Ala Pro Ser Cys Val Tyr Ile His Pro Asp
                115                 120                 125
Ser Pro Asn Phe Gly Ala His Trp Met Lys Ala Pro Val Ser Phe Ser
                130                 135                 140
Lys Val Lys Leu Thr Asn Lys Leu Asn Gly Gly Gln Ile Met Leu
145                     150                 155                 160
Asn Ser Leu His Lys Tyr Glu Pro Arg Ile His Ile Val Arg Val Gly
                    165                 170                 175
Asp Pro Gln Arg Met Ile Thr Ser His Cys Phe Pro Glu Thr Gln Phe
                180                 185                 190
Ile Ala Val Thr Ala Tyr Gln Asn Glu Glu Ile Thr Ala Leu Lys Ile
            195                 200                 205
Lys Tyr Asn Pro Phe Ala Lys Ala Phe Leu Asp Ala Lys Glu Arg Ser
        210                 215                 220
Asp His Lys Glu Met Met Glu Glu Pro Gly Asp Ser Gln Gln Pro Gly
225                     230                 235                 240
Tyr Ser Gln Trp Gly Trp Leu Leu Pro Gly Thr Ser Thr Val Cys Pro
                    245                 250                 255
Pro Ala Asn Pro His Pro Gln Phe Gly Gly Ala Leu Ser Leu Pro Ser
                260                 265                 270
Thr His Ser Cys Asp Arg Tyr Pro Thr Leu Arg Ser His Arg Ser Ser
            275                 280                 285
Pro Tyr Pro Ser Pro Tyr Ala His Arg Asn Asn Ser Pro Thr Tyr Ser
        290                 295                 300
Asp Asn Ser Pro Ala Cys Leu Ser Met Leu Gln Ser His Asp Asn Trp
305                     310                 315                 320
Ser Ser Leu Gly Met Pro Ala His Pro Ser Met Leu Pro Val Ser His
                    325                 330                 335
Asn Ala Ser Pro Pro Thr Ser Ser Ser Gln Tyr Pro Ser Leu Trp Ser
                340                 345                 350
Val Ser Asn Gly Ala Val Thr Pro Gly Ser Gln Ala Ala Ala Val Thr
            355                 360                 365
Asn Gly Leu Gly Ala Gln Phe Phe Arg Gly Ser Pro Ala His Tyr Thr
        370                 375                 380
Pro Leu Thr His Pro Val Ser Ala Pro Ser Ser Ser Gly Ser Pro Leu
385                     390                 395                 400
Tyr Glu Gly Ala Ala Ala Ala Thr Asn Ile Val Asp Ser Gln Tyr Asp
                    405                 410                 415
Ala Ala Ala Gln Gly Arg Leu Ile Ala Ser Trp Thr Pro Val Ser Pro
                420                 425                 430
```

Pro Ser Met
        435

<210> SEQ ID NO 19
<211> LENGTH: 1370
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1350)

<400> SEQUENCE: 19

```
gaattccgc atg gcc gat gaa gct ccg agc tcc cct ggc acc gag agc gcg        51
          Met Ala Asp Glu Ala Pro Ser Ser Pro Gly Thr Glu Ser Ala
          1               5                   10 gga aag agc ctg cag tac cga gtg gac cac ctg ctg agc gcc gtg gag          99
Gly Lys Ser Leu Gln Tyr Arg Val Asp His Leu Leu Ser Ala Val Glu
15                  20                  25                  30 aat gag ctg cag gcg ggc agc gag aag ggc gac ccc aca gag cgc gaa         147
Asn Glu Leu Gln Ala Gly Ser Glu Lys Gly Asp Pro Thr Glu Arg Glu
                35                  40                  45 ctg cgc gtg ggc ctg gag gag agc gag ctg tgg ctg cgc ttc aag gag         195
Leu Arg Val Gly Leu Glu Glu Ser Glu Leu Trp Leu Arg Phe Lys Glu
            50                  55                  60 ctc acc aat gag atg atc gtg acc aag aac ggc agg agg atg ttt ccg         243
Leu Thr Asn Glu Met Ile Val Thr Lys Asn Gly Arg Arg Met Phe Pro
        65                  70                  75 gtg ctg aag gtg aac gtg tct ggc ctg gac ccc aac gcc atg tac tcc         291
Val Leu Lys Val Asn Val Ser Gly Leu Asp Pro Asn Ala Met Tyr Ser
    80                  85                  90 ttc ctg ctg gac ttc gtg gcg gcg gac aac cac cgc tgg aag tac gtg         339
Phe Leu Leu Asp Phe Val Ala Ala Asp Asn His Arg Trp Lys Tyr Val
95                  100                 105                 110 aac ggg gaa tgg gtg ccg ggg ggc aag ccg gag ccg cag gcg ccc agc         387
Asn Gly Glu Trp Val Pro Gly Gly Lys Pro Glu Pro Gln Ala Pro Ser
                115                 120                 125 tgc gtc tac atc cac ccc gac tcg ccc aac ttc ggg gcc cac tgg atg         435
Cys Val Tyr Ile His Pro Asp Ser Pro Asn Phe Gly Ala His Trp Met
            130                 135                 140 aag gct ccc gtc tcc ttc agc aaa gtc aag ctc acc aac aag ctc aac         483
Lys Ala Pro Val Ser Phe Ser Lys Val Lys Leu Thr Asn Lys Leu Asn
        145                 150                 155 gga ggg ggc cag atc atg ctg aac tcc ttg cat aag tat gag cct cga         531
Gly Gly Gly Gln Ile Met Leu Asn Ser Leu His Lys Tyr Glu Pro Arg
    160                 165                 170 atc cac ata gtg aga gtt ggg gat cca cag cgc atg atc acc agc cac         579
Ile His Ile Val Arg Val Gly Asp Pro Gln Arg Met Ile Thr Ser His
175                 180                 185                 190 tgc ttc cct gag acc cag ttc ata gcg gtg act gct tat cag aac gag         627
Cys Phe Pro Glu Thr Gln Phe Ile Ala Val Thr Ala Tyr Gln Asn Glu
                195                 200                 205 gag atc aca gct ctt aaa att aag tac aat cca ttt gca aaa gct ttc         675
Glu Ile Thr Ala Leu Lys Ile Lys Tyr Asn Pro Phe Ala Lys Ala Phe
            210                 215                 220 ctt gat gca aag gaa aga agt gat cac aaa gag atg atg gag gaa ccc         723
Leu Asp Ala Lys Glu Arg Ser Asp His Lys Glu Met Met Glu Glu Pro
        225                 230                 235 gga gac agc cag caa cct ggg tac tcc caa tgg ggg tgg ctt ctt cct         771
Gly Asp Ser Gln Gln Pro Gly Tyr Ser Gln Trp Gly Trp Leu Leu Pro
```

```
gga  acc  agc  acc  gtg  tgt  cca  cct  gca  aat  cct  cat  cct  cag  ttt  gga    819
Gly  Thr  Ser  Thr  Val  Cys  Pro  Pro  Ala  Asn  Pro  His  Pro  Gln  Phe  Gly
255                 260                 265                 270 ggt  gcc  ctc  tcc  ctc  ccc  tcc  acg  cac  agc  tgt  gac  agg  tac  cca  acc    867
Gly  Ala  Leu  Ser  Leu  Pro  Ser  Thr  His  Ser  Cys  Asp  Arg  Tyr  Pro  Thr
                 275                 280                 285 ctg  agg  agc  cac  cgg  tcc  tca  ccc  tac  ccc  agc  ccc  tat  gct  cat  cgg    915
Leu  Arg  Ser  His  Arg  Ser  Ser  Pro  Tyr  Pro  Ser  Pro  Tyr  Ala  His  Arg
                 290                 295                 300 aac  aat  tct  cca  acc  tat  tct  gac  aac  tca  cct  gca  tgt  tta  tcc  atg    963
Asn  Asn  Ser  Pro  Thr  Tyr  Ser  Asp  Asn  Ser  Pro  Ala  Cys  Leu  Ser  Met
                 305                 310                 315 ctg  caa  tcc  cat  gac  aat  tgg  tcc  agc  ctt  gga  atg  cct  gcc  cat  ccc   1011
Leu  Gln  Ser  His  Asp  Asn  Trp  Ser  Ser  Leu  Gly  Met  Pro  Ala  His  Pro
320                 325                 330 agc  atg  ctc  ccc  gtg  agc  cac  aat  gcc  agc  cca  cct  acc  agc  tcc  agt   1059
Ser  Met  Leu  Pro  Val  Ser  His  Asn  Ala  Ser  Pro  Pro  Thr  Ser  Ser  Ser
335                 340                 345                 350 cag  tac  ccc  agc  ctg  tgg  tct  gtg  agc  aac  ggc  gcc  gtc  acc  ccg  ggc   1107
Gln  Tyr  Pro  Ser  Leu  Trp  Ser  Val  Ser  Asn  Gly  Ala  Val  Thr  Pro  Gly
                 355                 360                 365 tcc  cag  gca  gca  gcc  gtg  acc  aac  ggg  ctg  ggg  gcc  cag  ttc  ttc  cgg   1155
Ser  Gln  Ala  Ala  Ala  Val  Thr  Asn  Gly  Leu  Gly  Ala  Gln  Phe  Phe  Arg
                 370                 375                 380 ggc  tcc  ccc  gcg  cac  tac  aca  ccc  ctc  acc  cat  ccg  gtc  tcg  gca  ccc   1203
Gly  Ser  Pro  Ala  His  Tyr  Thr  Pro  Leu  Thr  His  Pro  Val  Ser  Ala  Pro
                 385                 390                 395 tct  tcc  tcg  gga  tcc  cca  ctg  tac  gaa  ggg  gcg  gcc  gcg  gcc  aca  aac   1251
Ser  Ser  Ser  Gly  Ser  Pro  Leu  Tyr  Glu  Gly  Ala  Ala  Ala  Ala  Thr  Asn
                 400                 405                 410 atc  gtg  gac  agc  cag  tac  gac  gcc  gca  gcc  caa  ggc  cgc  ctc  ata  gcc   1299
Ile  Val  Asp  Ser  Gln  Tyr  Asp  Ala  Ala  Ala  Gln  Gly  Arg  Leu  Ile  Ala
415                 420                 425                 430 tca  tgg  aca  cct  gtg  tcg  cca  cct  tcc  atg  cat  cac  cat  cac  cat  cac   1347
Ser  Trp  Thr  Pro  Val  Ser  Pro  Pro  Ser  Met  His  His  His  His  His  His
                 435                 440                 445 tga  gactagtccc  gggcggccgc                                                       1370
```

<210> SEQ ID NO 20
<211> LENGTH: 446
<212> TYPE: PRT
<213> ORGANISM: Artificial
<220> FEATURE:
<223> OTHER INFORMATION: Synthetic Construct

<400> SEQUENCE: 20

Met Ala Asp Glu Ala Pro Ser Ser Pro Gly Thr Glu Ser Ala Gly Lys
1               5                   10                  15

Ser Leu Gln Tyr Arg Val Asp His Leu Leu Ser Ala Val Glu Asn Glu
                20                  25                  30

Leu Gln Ala Gly Ser Glu Lys Gly Asp Pro Thr Glu Arg Glu Leu Arg
            35                  40                  45

Val Gly Leu Glu Glu Ser Glu Leu Trp Leu Arg Phe Lys Glu Leu Thr
        50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

```
Leu Asp Phe Val Ala Ala Asp Asn His Arg Trp Lys Tyr Val Asn Gly
            100                 105                 110

Glu Trp Val Pro Gly Gly Lys Pro Glu Pro Gln Ala Pro Ser Cys Val
            115                 120                 125

Tyr Ile His Pro Asp Ser Pro Asn Phe Gly Ala His Trp Met Lys Ala
            130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Asp Pro Gln Arg Met Ile Thr Ser His Cys Phe
            180                 185                 190

Pro Glu Thr Gln Phe Ile Ala Val Thr Ala Tyr Gln Asn Glu Glu Ile
            195                 200                 205

Thr Ala Leu Lys Ile Lys Tyr Asn Pro Phe Ala Lys Ala Phe Leu Asp
210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Val Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
            275                 280                 285

Ser His Arg Ser Ser Pro Tyr Pro Ser Pro Tyr Ala His Arg Asn Asn
    290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
            355                 360                 365

Ala Ala Ala Val Thr Asn Gly Leu Gly Ala Gln Phe Phe Arg Gly Ser
370                 375                 380

Pro Ala His Tyr Thr Pro Leu Thr His Pro Val Ser Ala Pro Ser Ser
385                 390                 395                 400

Ser Gly Ser Pro Leu Tyr Glu Gly Ala Ala Ala Ala Thr Asn Ile Val
                405                 410                 415

Asp Ser Gln Tyr Asp Ala Ala Ala Gln Gly Arg Leu Ile Ala Ser Trp
            420                 425                 430

Thr Pro Val Ser Pro Pro Ser Met His His His His His His
            435                 440                 445
```